US012344592B2

(12) United States Patent
Kamboj et al.

(10) Patent No.: US 12,344,592 B2
(45) Date of Patent: Jul. 1, 2025

(54) METHODS, PROCESSES AND INTERMEDIATES FOR PREPARING CHROMAN COMPOUNDS

(71) Applicant: Lupin Limited, Maharastra (IN)

(72) Inventors: Rajender Kumar Kamboj, Pune Maharashtra (IN); Kamlesh Jyotindra Padiya, Pune Maharashtra (IN); Kamalakannan Prabakaran, Pune Maharashtra (IN); Kumar Ram Naik, Pune Maharashtra (IN); Bhavani Shankar Rajesh, Pune Maharashtra (IN); Ganpati Powar Rajendra, Pune Maharashtra (IN); Subhash Ingawale Sachin, Pune Maharashtra (IN); Dattatray Karche Amit, Pune Maharashtra (IN); Shankar Dange Santoshkumar, Pune Maharashtra (IN); Barve Sitaram Rambhau, Pune Maharashtra (IN)

(73) Assignee: LUPIN LIMITED, Maharastra (IN)

( * ) Notice: Subject to any disclaimer, the term of this patent is extended or adjusted under 35 U.S.C. 154(b) by 433 days.

(21) Appl. No.: 17/792,298

(22) PCT Filed: Jan. 17, 2021

(86) PCT No.: PCT/IN2021/050045

§ 371 (c)(1),
(2) Date: Jul. 12, 2022

(87) PCT Pub. No.: WO2021/144814

PCT Pub. Date: Jul. 22, 2021

(65) Prior Publication Data

US 2023/0140054 A1 May 4, 2023

(30) Foreign Application Priority Data

Jan. 17, 2020 (IN) ............................ 202021002110

(51) Int. Cl.
*C07D 311/58* (2006.01)

(52) U.S. Cl.
CPC ................................. *C07D 311/58* (2013.01)

(58) Field of Classification Search
CPC .................................................... C07D 311/58
See application file for complete search history.

(56) References Cited

U.S. PATENT DOCUMENTS

| | | | | |
|---|---|---|---|---|
| 5,171,865 | A | 12/1992 | Kurono et al. | |
| 9,163,001 | B2 * | 10/2015 | Shukla | A61P 19/00 |
| 9,598,391 | B2 * | 3/2017 | Shukla | A61P 19/08 |
| 9,987,249 | B2 * | 6/2018 | Shukla | A61P 35/00 |
| 2003/0199497 | A1 | 10/2003 | Ruat et al. | |
| 2011/0028452 | A1 | 2/2011 | Didiuk et al. | |

FOREIGN PATENT DOCUMENTS

| | | | |
|---|---|---|---|
| WO | 2002/012181 | A1 | 2/2002 |
| WO | 2004/069793 | A2 | 8/2004 |
| WO | 2004/106280 | A1 | 12/2004 |
| WO | 2006/123725 | A2 | 11/2006 |
| WO | 2008/059854 | A1 | 5/2008 |
| WO | 2009/065406 | A1 | 5/2009 |
| WO | 2010/038895 | A1 | 4/2010 |
| WO | 2010/042642 | A1 | 4/2010 |
| WO | 2010/136037 | A1 | 12/2010 |
| WO | 2010/150837 | A1 | 12/2010 |
| WO | 2012/069402 | A1 | 5/2012 |
| WO | 2012/069419 | A1 | 5/2012 |
| WO | 2012/069421 | A1 | 5/2012 |
| WO | 2012/120476 | A1 | 9/2012 |
| WO | 2012/127385 | A1 | 9/2012 |
| WO | 2012/127388 | A1 | 9/2012 |
| WO | 2013/124828 | A1 | 8/2013 |

OTHER PUBLICATIONS

PCT International Search Report for PCT Application No. PCT/IN2021/050045 mailed Mar. 16, 2021 (3 pages).
PCT Written Opinion for PCT Application No. PCT/IN2021/050045 mailed Mar. 16, 2021 (6 pages).
Kessler et al., "N1-Benzoyl-N2-[1-(1-naphthyl)ethyl]-trans-1,2-diaminocyclohexanes: Development of 4-Chlorophenylcarboxamide (Calhex 231) as a New Calcium Sensing Receptor Ligand Demonstrating Potent Calcilytic Activity," J. Med. Chem., 2006, 49:5119-5128.

* cited by examiner

*Primary Examiner* — Golam M Shameem

(74) *Attorney, Agent, or Firm* — DUANE MORRIS LLP; Gregory M. Lefkowitz; Brandon A. Chan

(57) ABSTRACT

This disclosure describes an economical and scalable method and process to synthesize the Calcium sensing receptor (CaSR) modulating agent 2-methyl-5-((2R,4S)-2-((((R)-1-(naphthalen-1-yl)ethyl)amino)methyl)chroman-4-yl)benzoic acid, its intermediates and pharmaceutically acceptable salts therefor. Uses of said intermediates for synthesis of compounds which may be intermediates to the synthesis of 2-methyl-5-((2R,4S)-2-((((R)-1-(naphthalen-1-yl)ethyl)amino)methyl)chroman-4-yl)benzoic acid are also described herein.

15 Claims, No Drawings

METHODS, PROCESSES AND INTERMEDIATES FOR PREPARING CHROMAN COMPOUNDS

CROSS-REFERENCE TO RELATED APPLICATIONS

This application is a National Stage Application of PCT/IN2021/050045, filed Jan. 17, 2021, which claims benefit in and to Indian Provisional Patent Application No. 202021002110, filed Jan. 17, 2020, the disclosures of which are incorporated herein by reference in their entireties. To the extent appropriate, a claim of priority is made to the above disclosed applications.

FIELD

The disclosure relates to the synthesis of substituted chroman compounds and novel intermediates, and the use of novel intermediates. In particular, the disclosure relates to enantioselective synthesis of the Calcium sensing receptor (CaSR) modulating agent 2-methyl-5-((2R,4S)-2-((((R)-1-(naphthalen-1-yl)ethyl)amino)methyl)chroman-4-yl)benzoic acid, its intermediates and pharmaceutically acceptable salts thereof.

INCORPORATION BY REFERENCE

All U.S. patents, U.S. patent application publications, foreign patents, foreign and PCT published applications, articles and other documents, references and publications noted herein, and all those listed as References Cited in any patent or patents that issue herefrom, are hereby incorporated by reference in their entirety. The information incorporated is as much a part of this application as if all the text and other content was repeated in this application, and will be treated as part of the text and content of this application as filed.

BACKGROUND

The following includes information that may be useful in understanding the invention. It is not an admission that any of the information, publications or documents specifically or implicitly referenced herein is prior art, or essential, to the described or claimed invention. All publications and patents mentioned herein are hereby incorporated by reference in their entirety.

Calcium-sensing receptor is a class C G-protein-coupled receptor (GPCR). It plays a major role in the maintenance of a physiological serum ionized calcium ($Ca^{2+}$) concentration by regulating the circulating levels of parathyroid hormone. Extracellular $Ca^{2+}$ ($Ca^{2+}o$) is the primary physiological ligand for CaSR.

Small molecules that are positive allosteric modulators called calcimimetics, modulate and improve the receptors sensitivity to the already existing milieu of extracellular ionic calcium and reduces PTH secretion. This has been explored as potential therapy for hyperparathyroidism and diseases associated with decreased CaSR signaling. Cinacalcet was the first CaSR modulating agent to be approved by the U.S. Food and Drug Administration (FDA).

PCT International Patent Application Publication Nos. WO 2012/127388, WO 2012/120476, WO 2012/127385, WO 2012/069421, WO 2012/069419, WO 2012/069402, US 2011/0028452, WO 2010/150837, WO 2010/136037, WO 2010/042642, WO 2010/038895, WO 2009/065406, WO 2008/059854, WO 2006/123725, WO 2004/106280, WO 2004/069793, WO 2002/012181 and US 2003/0199497 refer to compounds related to calcium sensing receptors (CaSR) for the treatment of various diseases mediated by CaSR. Kessler et al., "N1-Benzoyl-N2-[1-(1-naphthyl)ethyl]-trans-1,2-diaminocyclohexanes: Development of 4-Chlorophenylcarboxamide (Calhex 231) as a New Calcium Sensing Receptor Ligand Demonstrating Potent Calcilytic Activity," J. Med. Chem. (2006), 49, 5119-5128 also discloses compounds related CaSR.

WO2013/124828 discloses a series of substituted chroman compounds for CaSR modulation. One specific compound disclosed therein is 2-methyl-5-((2R,4S)-2-((((R)-1-(naphthalen-1-yl)ethyl)amino)methyl)chroman-4-yl) benzoic acid. The application also describes a general method of synthesis of these substituted chroman compounds. The process disclosed involves chiral resolution of racemic chroman-2-carboxylic acid used as the starting material to get the desired (R) chroman-2-carboxlic acid in subsequent steps. However, carrying out the chiral resolution of the intermediate is difficult, costly, and not suitable for an industrial scale. Further, carrying out the chiral resolution of the intermediate also affects the overall yield of the manufacturing method.

In view of the above, there is a need for a more efficient method that is less complicated, more cost effective and industrially advantageous for the preparation of 2-methyl-5-((2R,4S)-2-((((R)-1-(naphthalen-1-yl)ethyl)amino) methyl)chroman-4-yl)benzoic acid and its salts.

SUMMARY

The invention described and claimed herein has many attributes and aspects including, but not limited to, those set forth or described or referenced in this Summary. It is not intended to be all-inclusive and the invention described and claimed herein are not limited to or by the features or embodiments identified in this Summary, which is included for purposes of illustration only and not restriction.

This disclosure provides for facile, cost-effective and industrially advantageous methods and processes for the synthesis of 2-methyl-5-((2R,4S)-2-((((R)-1-(naphthalen-1-yl)ethyl)amino)methyl)chroman-4-yl)benzoic acid and its salts. Particularly, the methods and processes described herein involve an enantioselective method comprising steps wherein the stereochemistry of intermediates or final compounds is controlled. In some aspects, this disclosure provides with novel intermediates Compound 3, Compound 4, Compound 5, Compound 6, Compound 7", Compound 7, and Compound 16 (each described in detail herein) that are useful as precursors in the synthesis of Compound A (described in detail herein). In some aspects, this disclosure provides for a method and process for synthesizing Compound 7 from a route involving Compound 3.

The methods and processes disclosed herein also involve novel intermediates and/or their salts, which are useful for the facile synthesis of Compound A and its salts.

In some aspects, this disclosure provides for the compound (R)—N-(1-(naphthalen-1-yl)ethyl)-4-oxo-4H-chromene-2-carboxamide (Compound 3) and/or its salts, Compound 3

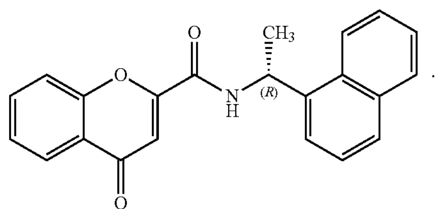

In some aspects, this disclosure provides for the compound (R)—N—((R)-1-(naphthalen-1-yl)ethyl)-4-oxochromane-2-carboxamide (Compound 4) and/or its salts, Compound 4

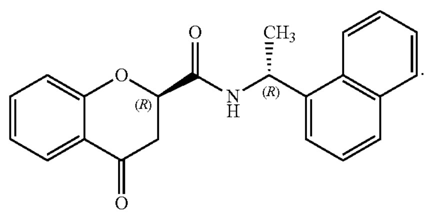

In some aspects, this disclosure provides for the compound (R)—N—((R)-1-(naphthalen-1-yl)ethyl)spiro[chromane-4,2'-[1,3]dioxolane]-2-carboxamide (Compound 5) and/or its salts, Compound 5

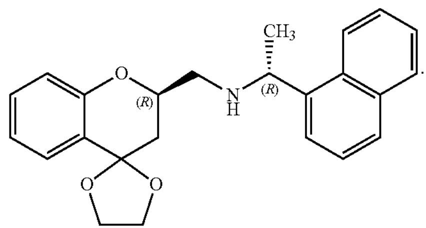

In some aspects, this disclosure provides for the compound (R)-1-(naphthalen-1-yl)-N—(((R)-spiro[chromane-4,2'-[1,3]dioxolan]-2-yl)methyl)ethan-1-amine (Compound 6) and/or its salts, Compound 6

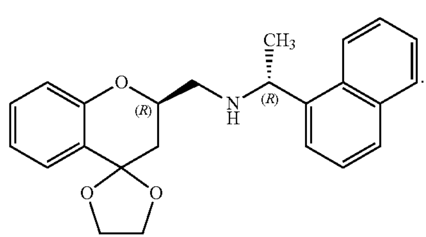

In some aspects, this disclosure provides for the compound (R)-2-((((R)-1-(naphthalen-1-yl)ethyl)amino)methyl)chroman-4-one (Compound 7) and its salts, and (R)-2-((((R)-1-(naphthalen-1-yl)ethyl) amino)methyl)chroman-4-one (Compound 7"), Compound 7

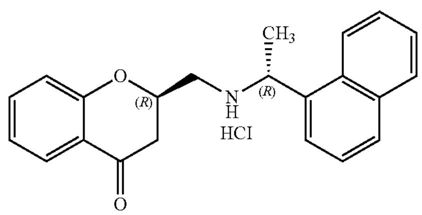

Compound 7''

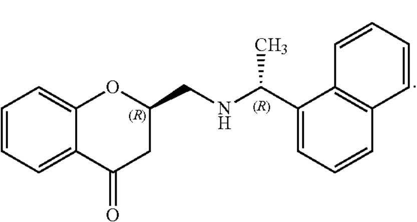

In some aspects, this disclosure provides for the (R)-2-(((1-(naphthalen-1-yl)ethyl)amino)methyl)-4H-chromen-4-one (Compound 16) and its salts, Compound 16

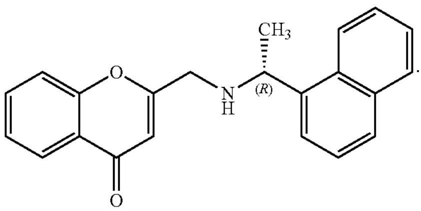

In some aspects, this disclosure provides for a method and process for the synthesis of 2-methyl-5-((2R,4S)-2-((((R)-1-(naphthalen-1-yl)ethyl)amino)methyl) chroman-4-yl)benzoic acid hydrochloride (Compound A), Compound-A

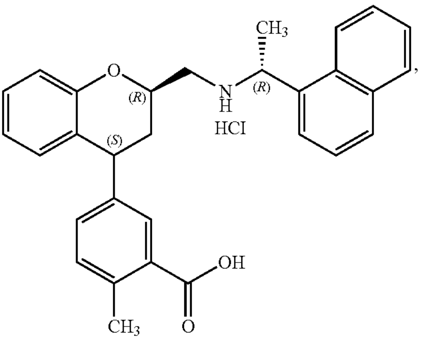

as depicted in Scheme-1:
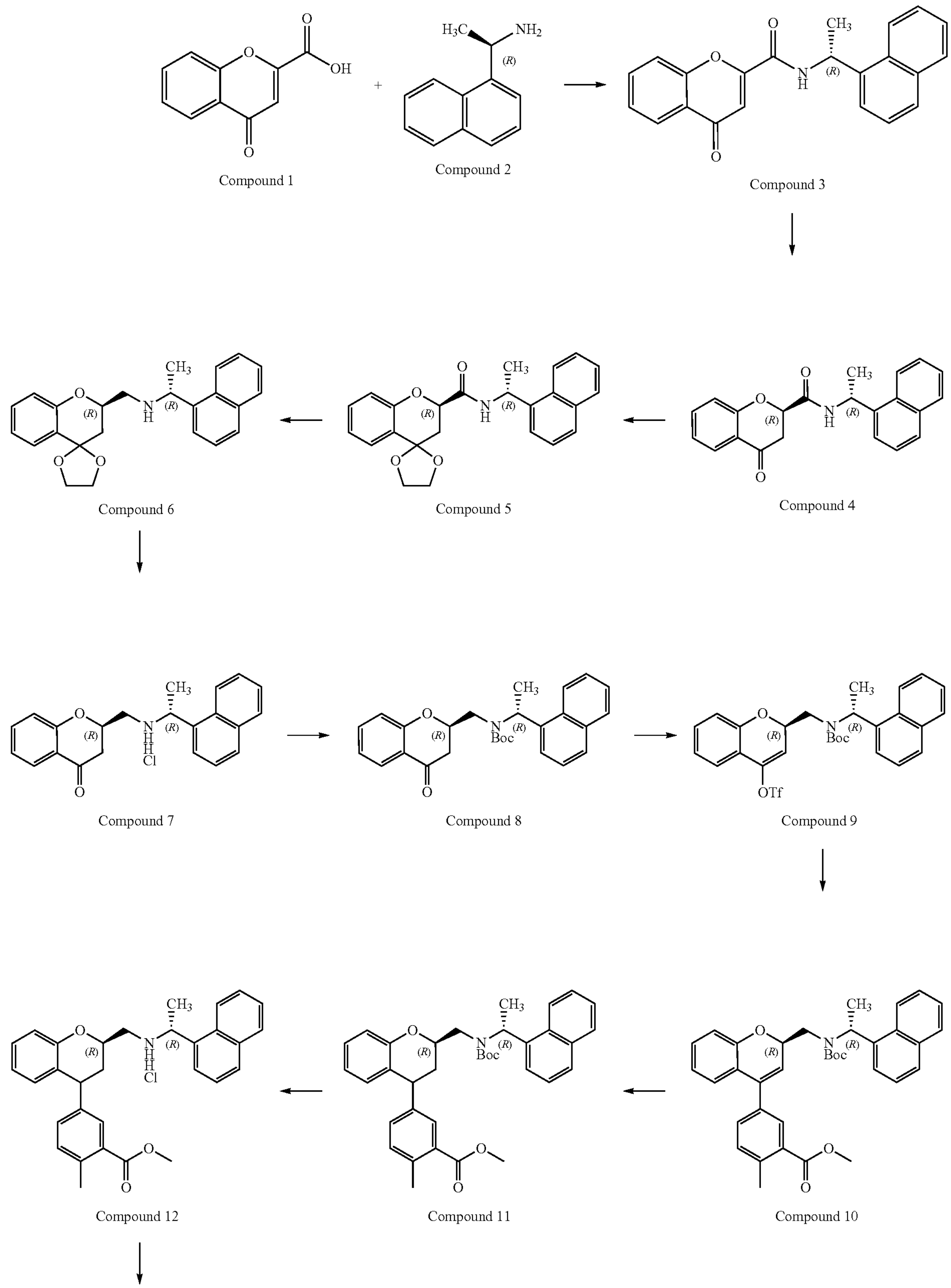

-continued

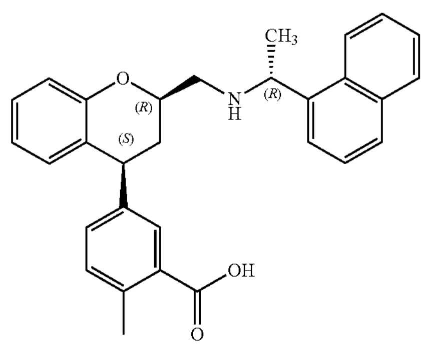

Compound A″

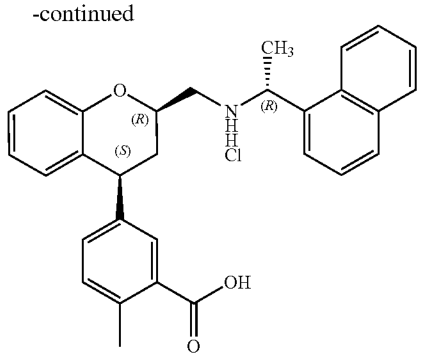

Compound A

, which comprises:

a) reacting 4-oxo-4H-chromene-2-carboxylic acid (Compound 1) with (R)-1-(naphthalen-1-yl)ethan-1-amine (Compound 2) in the presence of one or more coupling catalysts to obtain (R)—N-(1-(naphthalen-1-yl)ethyl)-4-oxo-4H-chromene-2-carboxamide (Compound 3), wherein the one or more coupling catalysts is propylphosphonic anhydride (T3P), 1-Ethyl-3-(3-dimethylaminopropyl)carbodiimide (EDCI), 1-Ethyl-3-(3-dimethylaminopropyl)carbodiimide hydrochloride (EDCI-HCl), N,N'-Dicyclohexylcarbodiimide (DCC), N,N'-Diisopropylcarbodiimide (DIC), 1-[Bis(dimethylamino)methylene]-1H-1,2,3-triazolo[4,5-b]pyridinium 3-oxide hexafluorophosphate (HATU), 2-(1H-benzotriazol-1-yl)-1,1,3,3-tetramethyluronium hexafluorophosphate (HBTU), or a combination thereof;

b) enantioselectively reducing the double bond of Compound 3 by asymmetric hydrogenation to obtain the optically active (R)—N—((R)-1-(naphthalen-1-yl)ethyl)-4-oxochromane-2-carboxamide (Compound 4) using one or more optically active diphosphine ligands, wherein the one or more optically active diphosphine ligands is (R)-(+)-4,4'-Bis(diphenylphosphino)-3,3'-bi(1,2-methylenedioxybenzene) [(R)-SEGPHOS®], 4,4'-Bis(diphenylphosphino)-3,3'-bi(1,2-methylenedioxybenzene) [SEGPHOS®], (R)-(+)-4,4'-Bis[di(3,5-xylyl)phosphino]-3,3'-bi(1,2-methylenedioxybenzene) [(R)-DM-SEGPHOS®], (R)-(−)-4,4'-Bis[di(3,5-di-tert-butyl-4-methoxyphenyl)phosphino]-3,3'-bi(1,2-methylenedioxybenzene) [((R)-DTBM-SEGPHOS®)], (R)-(+)-2,2'-Bis(diphenylphosphino)-1,1'-binaphthalene [(R)-BINAP], 2-Dicyclohexylphosphino-2',6'-dimethoxybiphenyl [s-Phos], 5-Bis(diphenylphosphino)-9,9-dimethylxanthene [Xantphos], (2R,3R)-(+)-Bis(diphenylphosphino)butane [R-Chiraphos], 4,4,4',4',6,6'-Hexamethyl-2,2'-spirobichroman-8,8'-diylbis(diphenylphosphane) [SPANphos], Bis(diphenylphosphinoethyl)phenylphosphine [Triphos], (2R,2'R,5R,5'R)-2,2',5,5'-Tetramethyl-1,1'-(o-phenylene)diphospholane [R,R-Me-DuPhos], or a combination thereof;

c) reacting Compound 4 with glycol (such as, but not limited to, ethylene glycol or propylene glycol) in the presence of one or more catalysts in the presence of one or more nonpolar solvents to obtain (R)—N—((R)-1-(naphthalen-1-yl)ethyl)spiro[chromane-4,2'-[1,3]dioxolane]-2-carboxamide (Compound 5), wherein the one or more catalysts is p-toluenesulfonic acid (PTSA), methanesulfonic acid (MSA), trifluoroacetic acid (TFA), tosylic acid (TsOH), pyridinium p-toluenesulfonate (PPTS), orthophosphoric acid, or a combination thereof, and wherein the one or more nonpolar solvents includes, but not limited to, toluene (methylbenzene), xylene, dioxane, benzene, dichloromethane (CH2Cl2), carbon tetrachloride (CCl4), trichloromethane (CHCl3), methyl tert-butyl ether (MTBE), or a combination thereof;

d) reducing the amide group of Compound 5 using a reducing agent to obtain (R)-1-(naphthalen-1-yl)-N—(((R)-spiro[chromane-4,2'-[1,3]dioxolan]-2-yl)methyl)ethan-1-amine (Compound 6), wherein the reducing agent is Vitride, borane-dimethyl sulphide complex, (Zn(OAc)2)/DEMS, or a combination thereof;

e) treating Compound 6 with aqueous acidic media to obtain (R)-2-((((R)-1-(naphthalen-1-yl)ethyl)amino)methyl)chroman-4-one hydrochloride (Compound 7);

f) reacting Compound 7 with Boc anhydride (Di-tert-butyl dicarbonate) in the presence of one or more basic catalysts to obtain tert-butyl ((R)-1-(naphthalen-1-yl)ethyl)(((R)-4-oxochroman-2-yl)methyl) carbamate (Compound 8), wherein the one or more basic catalyst is tripotassium phosphate, triethyl amine, pyridine, DMAP, DBU, DBN, sodium carbonate, sodium-bicarbonate, sodium carbonate, potassium bi-carbonate, potassium carbonate, or combination thereof;

g) reacting Compound 8 with one or more triflating agents to give (R)-2-(((tert-butoxycarbonyl)((R)-1-(naphthalen-1-yl)ethyl)amino)methyl)-2H-chromen-4-yl trifluoromethanesulfonate (Compound 9), wherein the one or more triflating agents is N-phenyl-bis(trifluoromethanesulfonimide), trifluoromethanesulfonic anhydride; N-(4-tert-Butylphenyl)bis(trifluoromethanesulfonimide), Bis(trifluoromethanesulfonyl)aniline, Comin's reagent, N-(5-Chloro-2-pyridyl)bis(trifluoromethanesulfonimide); trifluoromethanesulfonyl chloride, 4-nitrophenyl trifluoromethanesulfonate, 1-(trifluoromethanesulfonyl)imidazole)), or a combination thereof;

h) coupling Compound 9 with methyl 2-methyl-5-(4,4,5,5-tetramethyl-1,3,2-dioxaborolan-2-yl)benzoate in the presence of one or more palladium catalysts to give methyl-5-((R)-2-(((tert-butoxycarbonyl)((R)-1-(naphthalen-1-yl)ethyl)amino)methyl)-2H-chromen-4-yl)-2-methylbenzoate (Compound 10), wherein the one or more palladium catalysts is palladium-tetrakis(triphenylphosphine), palladium(II)bis(triphenylphosphine) dichloride, palladium(0) bis(dibenzylideneacetone), palladium(II)bis(triphenylphosphine) diacetate, [1,1'-bis(diphenylphosphino)ferrocene]dichloropalladium (II), or a combination thereof;

i) converting methyl-5-((R)-2-(((tert-butoxycarbonyl)((R)-1-(naphthalen-1-yl)ethyl)amino)methyl)-2H- chromen-4-yl)-2-methylbenzoate (Compound 10) to methyl 5-((2R)-2-(((tert-butoxycarbonyl)((R)-1-(naphthalen-1-yl)ethyl)amino)methyl) chroman-4-yl)-2-methylbenzoate (Compound 11), wherein the conversion is carried out through hydrogenation using palladium charcoal catalyst in methanolic ammonia under optimum hydrogen pressure not more than about 2.0 Kg/cm$^2$, or through treatment with ammonium formate in the presence of palladium charcoal catalyst optionally in the presence of one or more polar solvents, wherein the one or more polar solvents includes, but not limited to, methanol, ethanol, propanol, ethyl acetate, tetrahydrofuran, dioxane, or a combination thereof;

j) converting Compound 11 to methyl 2-methyl-5-((2R)-2-((((R)-1-(naphthalen-1-yl)ethyl)amino) methyl) chroman-4-yl)benzoate hydrochloride (Compound 12) through Boc-deprotection reaction using aqueous hydrochloric acid, trifluoroacetic acid or trimethyl silyl iodide in the presence of one or more polar solvents, wherein the one or more polar solvents includes, but not limited to, methanol, dichloromethane, ethanol, propanol, ethyl acetate, tetrahydrofuran, dioxane, or a combination thereof;

k) hydrolyzing the ester group of Compound 12 using one or more hydroxide bases (wherein the one or more hydroxide bases is sodium hydroxide, lithium hydroxide, potassium hydroxide, cesium hydroxide, lithium chloride, or a combination thereof), followed by aqueous reaction with the resultant carboxylate salt into the carboxylic acid, and isolation of the pure diastereoisomer by using recrystallization technique with a solvent mixture of one or more protic polar solvents and one or more aprotic polar solvents to give 2-methyl-5-((2R, 4S)-2-((((R)-1-(naphthalen-1-yl)ethyl)amino)methyl) chroman-4-yl)benzoic acid (Compound-A"), wherein the one or more protic polar solvents includes, but not limited to, ethanol, methanol, isopropanol, or a combination thereof, and the one or more aprotic polar solvents includes, but not limited to, dichloromethane, dimethylformamide, tetrahydrofuran, or a combination thereof; and l) converting Compound-A" to its hydrochloride salt, 2-methyl-5-((2R,4S)-2-((((R)-1-(naphthalen-1-yl) ethyl)amino)methyl) chroman-4-yl)benzoic acid hydrochloride (Compound A) using hydrochloric acid in one or more protic polar solvents, wherein the one or more protic polar solvents includes, but not limited to, ethanol, methanol, isopropanol, or a combination thereof.

In some aspects, this disclosure provides for a method and process for the synthesis of 2-methyl-5-((2R,4S)-2-((((R)-1-(naphthalen-1-yl)ethyl)amino)methyl) chroman-4-yl)benzoic acid hydrochloride (Compound A),

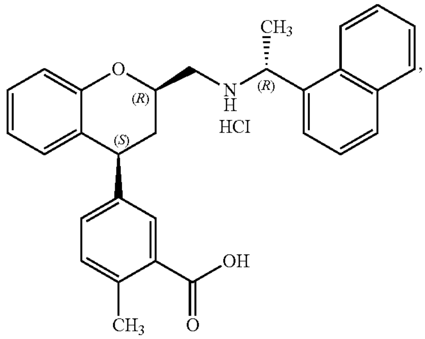

as depicted in Scheme 2:

SCHEME 2

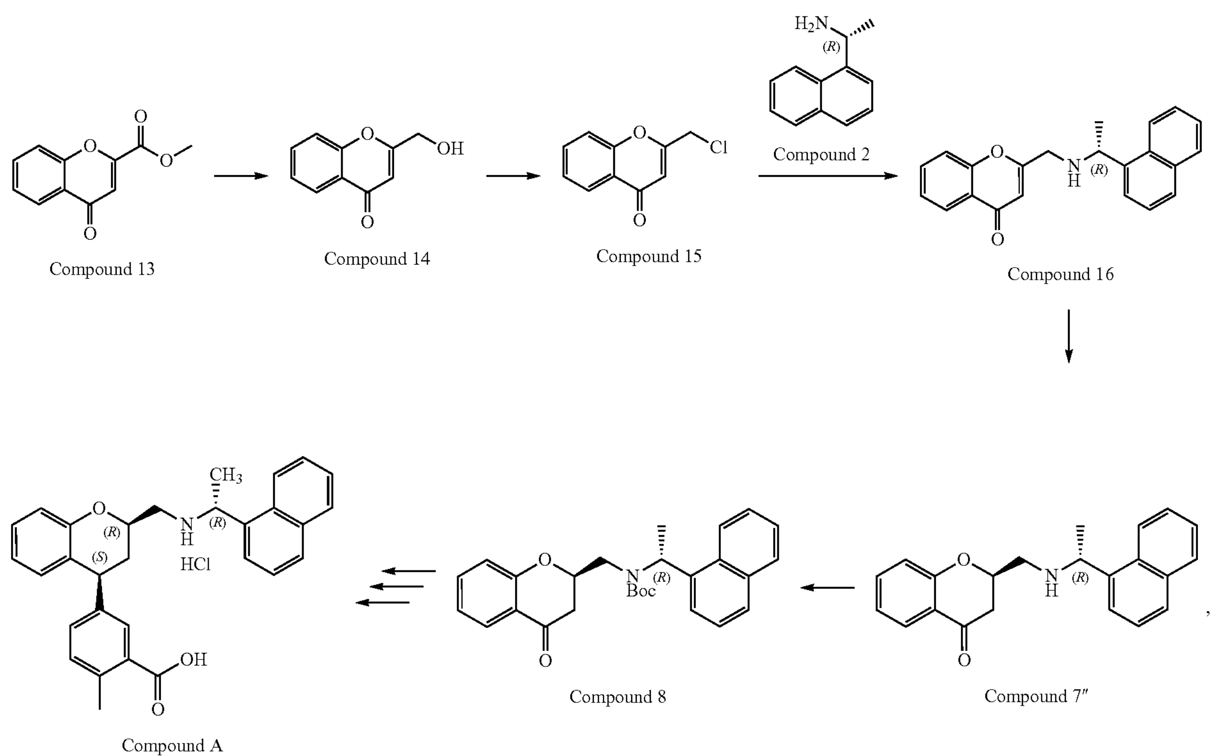

which comprises:

a) converting methyl 4-oxo-4H-chromene-2-carboxylate (Compound 13) to 2-(hydroxymethyl)-4H-chromen-4-one (Compound 14) by reacting Compound 14 with one or more reducing agents, wherein the one or more reducing agents is sodium borohydride (NaBH4), lithium borohydride (LiBH4), lithium aluminum hydride (LiAlH4), NaH, sodium cyanoborohydride, diisobutyl aluminum hydride, metal hydrides, tributyl tin, borane complexes (e.g., BH3-THF), or a combination thereof;

b) converting 2-(hydroxymethyl)-4H-chromen-4-one (Compound 14) to 2-(chloromethyl)-4H-chromen-4-one (Compound 15) by reacting Compound 14 with one or more chlorinating agents, wherein the one or more chlorinating agents is thionyl chloride, a sulfonyl chloride (such as, but not limited to, mesyl chloride, toluenesulfonyl chloride or trichloromethanesulfonic chloride), or a combination thereof;

c) coupling 2-(chloromethyl)-4H-chromen-4-one (Compound 15) with (R)-1-(naphthalen-2-yl)ethan-1-amine (Compound 2) to obtain (R)-2-(((1-(naphthalen-1-yl) ethyl)amino)methyl)-4H-chromen-4-one (Compound 16) in the presence of potassium carbonate, potassium iodide or combination thereof;

d) enantioselectively reducing the double bond of (R)-2-(((1-(naphthalen-1-yl)ethyl)amino)methyl)-4H-chromen-4-one (Compound 16) via asymmetric hydrogenation to obtain the optically active (R)-2-((((R)-1-(naphthalen-1-yl)ethyl) amino)methyl)chroman-4-one (Compound 7"), using one or more optically active diphosphine ligands, wherein the one or more optically active diphosphine ligands is (R)-(+)-4,4'-Bis(diphenylphosphino)-3,3'-bi(1,2-methylenedioxybenzene) [(R)-SEGPHOS® ], 4,4'-Bis(diphenylphosphino)-3,3'-bi(1,2-methylenedioxybenzene) [SEGPHOS®], (R)-(+)-4,4'-Bis[di(3,5-xylyl)phosphino]-3,3'-bi(1,2-methylenedioxybenzene) [(R)-DM-SEGPHOS®], (R)-(−)-4,4'-Bis[di(3,5-di-tert-butyl-4-methoxyphenyl) phosphino]-3,3'-bi(1,2-methylenedioxybenzene) [((R)-DTBM-SEGPHOS®)], (R)-(+)-2,2'-Bis (diphenylphosphino)-1,1'-binaphthalene [(R)-BINAP], 2-Dicyclohexylphosphino-2',6'-dimethoxybiphenyl [s-Phos], 5-Bis(diphenylphosphino)-9,9-dimethylxanthene [Xantphos], (2R,3R)-(+)-Bis(diphenylphosphino)butane [R-Chiraphos], 4,4,4',4',6,6'-Hexamethyl-2,2'-spirobichroman-8,8'-diylbis (diphenylphosphane) [SPANphos], Bis (diphenylphosphinoethyl)phenylphosphine [Triphos], (2R,2'R,5R,5'R)-2,2',5,5'-Tetramethyl-1,1'-(o-phenylene)diphospholane [R,R-Me-DuPhos], or a combination thereof;

e) treating Compound 7" with Boc anhydride (Di-tert-butyl dicarbonate) in the presence of one or more basic catalysts to obtain Compound 8, wherein the one or more basic catalysts is tripotassium phosphate, triethyl amine, pyridine, DMAP, DBU, DBN, sodium carbonate, sodium-bi-carbonate, sodium carbonate, potassium bi-carbonate, potassium carbonate, or combination thereof; and f) converting Compound 8 to Compound A as described in Scheme-1.

In some aspects, this disclosure provides for a method and process for the synthesis of 2-methyl-5-((2R,4S)-2-((((R)-1-(naphthalen-1-yl)ethyl)amino)methyl) chroman-4-yl)benzoic acid hydrochloride (Compound A),

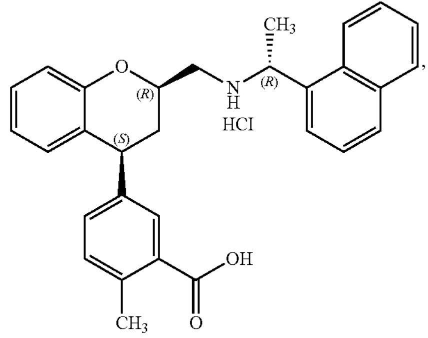

as depicted in Scheme-3:

SCHEME-3

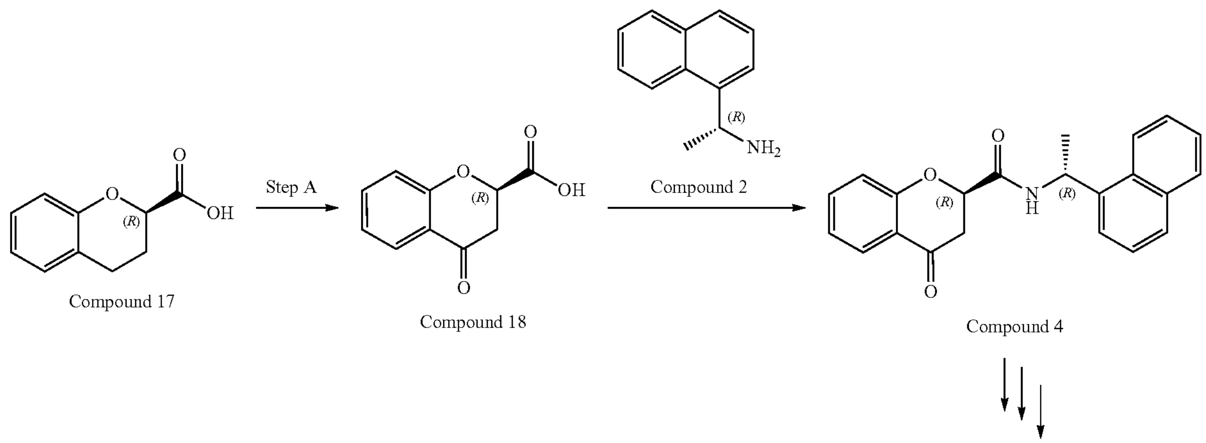

-continued

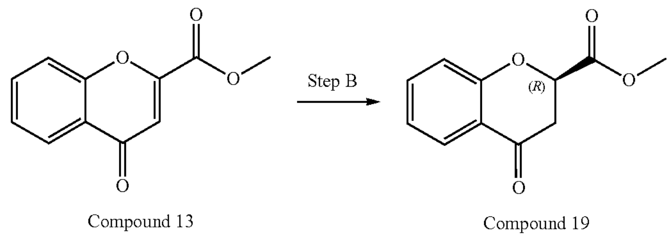

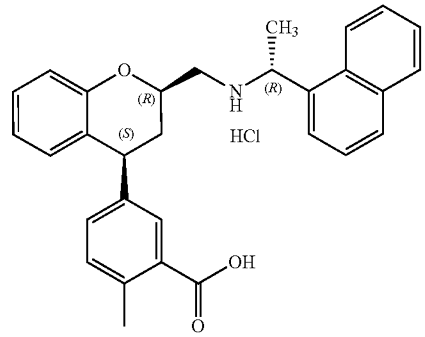

which comprises:

Step A:

a) converting (R)-chromane-2-carboxylic acid (Compound 17) to (R)-4-oxochromane-2-carboxylic acid (Compound 18) by treating Compound 17 with one or more oxidizing agents (such as, but not limited to, KMnO4, MnO2, tert-butyl hydroperoxide-Chromium (VI)oxide, potassium peroxomonosulfate, sodium bromate, FeCl3, TBAB-Copper dichloride, AIBN-Oxygen, NaClO2-N-Hydroxyphthalimide, or a combination thereof) in the presence of magnesium sulphate in one or more polar solvents (such as, but not limited to, tetrahydrofuran, dichloromethane (DCM), tedtrahydrofuran (THF), 2-methyltetrahydrofuran (2-Me-THF), toluene (methylbenzene), ethyl acetate, dimethylformamide (DMF), water, acetone or a combination thereof);

Step B:

a) converting methyl 4-oxo-4H-chromene-2-carboxylate (Compound 13) to methyl (R)-4-oxochromane-2-carboxylate (Compound 19) via asymmetric hydrogenation using one or more optically active diphosphine ligands (such as, but not limited to, (R)-(+)-4,4'-Bis (diphenylphosphino)-3,3'-bi(1,2-methylenedioxybenzene) [(R)-SEGPHOS® ], 4,4'-Bis(diphenylphosphino)-3,3'-bi(1,2-methylenedioxybenzene) [SEGPHOS®], (R)-(+)-4,4'-Bis[di(3,5-xylyl)phosphino]-3,3'-bi(1,2-methylenedioxybenzene) [(R)-DM-SEGPHOS®], (R)-(−)-4,4'-Bis[di(3,5-di-tert-butyl-4-methoxyphenyl)phosphino]-3,3'-bi(1,2-methylenedioxybenzene) [((R)-DTBM-SEGPHOS®)], (R)-(+)-2,2'-Bis(diphenylphosphino)-1,1'-binaphthalene [(R)-BINAP], 2-Dicyclohexylphosphino-2',6'-dimethoxybiphenyl [s-Phos], 5-Bis(diphenylphosphino)-9,9-dimethylxanthene [Xantphos], (2R,3R)-(+)-Bis (diphenylphosphino)butane [R-Chiraphos], 4,4,4',4',6,6'-Hexamethyl-2,2'-spirobichroman-8,8'-diylbis (diphenylphosphane) [SPANphos], Bis (diphenylphosphinoethyl)phenylphosphine [Triphos], (2R,2'R,5R,5'R)-2,2',5,5'-Tetramethyl-1,1'-(o-phenylene)diphospholane [R,R-Me-DuPhos], or a combination thereof);

b) hydrolyzing methyl (R)-4-oxochromane-2-carboxylate (Compound 19) to give (R)-4-oxochromane-2-carboxylic acid (Compound 18) using base hydrolysis in one or more polar solvents (such as, but not limited to, water, tetrahydrofuran, dichloromethane (DCM), 2-methyltetrahydrofuran (2-Me-THF), toluene (methylbenzene), ethyl acetate, dimethylformamide (DMF), or a combination thereof) using one or more bases (such as, but not limited to, sodium hydroxide, potassium hydroxide, cesium hydroxide, or combination thereof);

c) coupling (R)-4-oxochromane-2-carboxylic acid (Compound 18) with (R)-1-(naphthalen-1-yl)ethan-1-amine (Compound 2) in the presence of one or more coupling catalysts (such as, but not limited to, propylphosphonic anhydride (T3P) 1-Ethyl-3-(3-dimethylaminopropyl) carbodiimide (EDCI), 1-Ethyl-3-(3-dimethylaminopropyl)carbodiimide hydrochloride (EDCI-HCl), N,N'-Dicyclohexylcarbodiimide (DCC), N,N'-Diisopropylcarbodiimide (DIC), 1-[Bis (dimethylamino)methylene]-1H-1,2,3-triazolo[4,5-b] pyridinium 3-oxide hexafluorophosphate (HATU), 2-(1H-benzotriazol-1-yl)-1,1,3,3-tetramethyluronium hexafluorophosphate (HBTU), or a combination thereof) to obtain (R)—N-(1-(naphthalen-1-yl)ethyl)-4-oxo-4H-chromene-2-carboxamide (Compound 4); and d) converting (R)—N-(1-(naphthalen-1-yl)ethyl)-4-oxo-4H-chromene-2-carboxamide (Compound 4) to Compound A using method described in Scheme-1.

In some aspects, the disclosure provides a method or process for the synthesis of 2-methyl-5-((2R,4S)-2-((((R)-1-(naphthalen-1-yl)ethyl)amino)methyl) chroman-4-yl)benzoic acid hydrochloride (Compound A), Compound-A

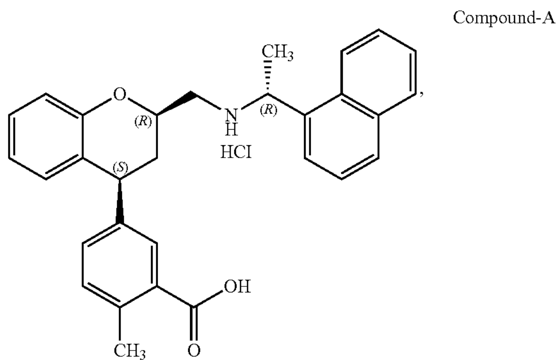

as depicted in Scheme-4:

SCHEME-4

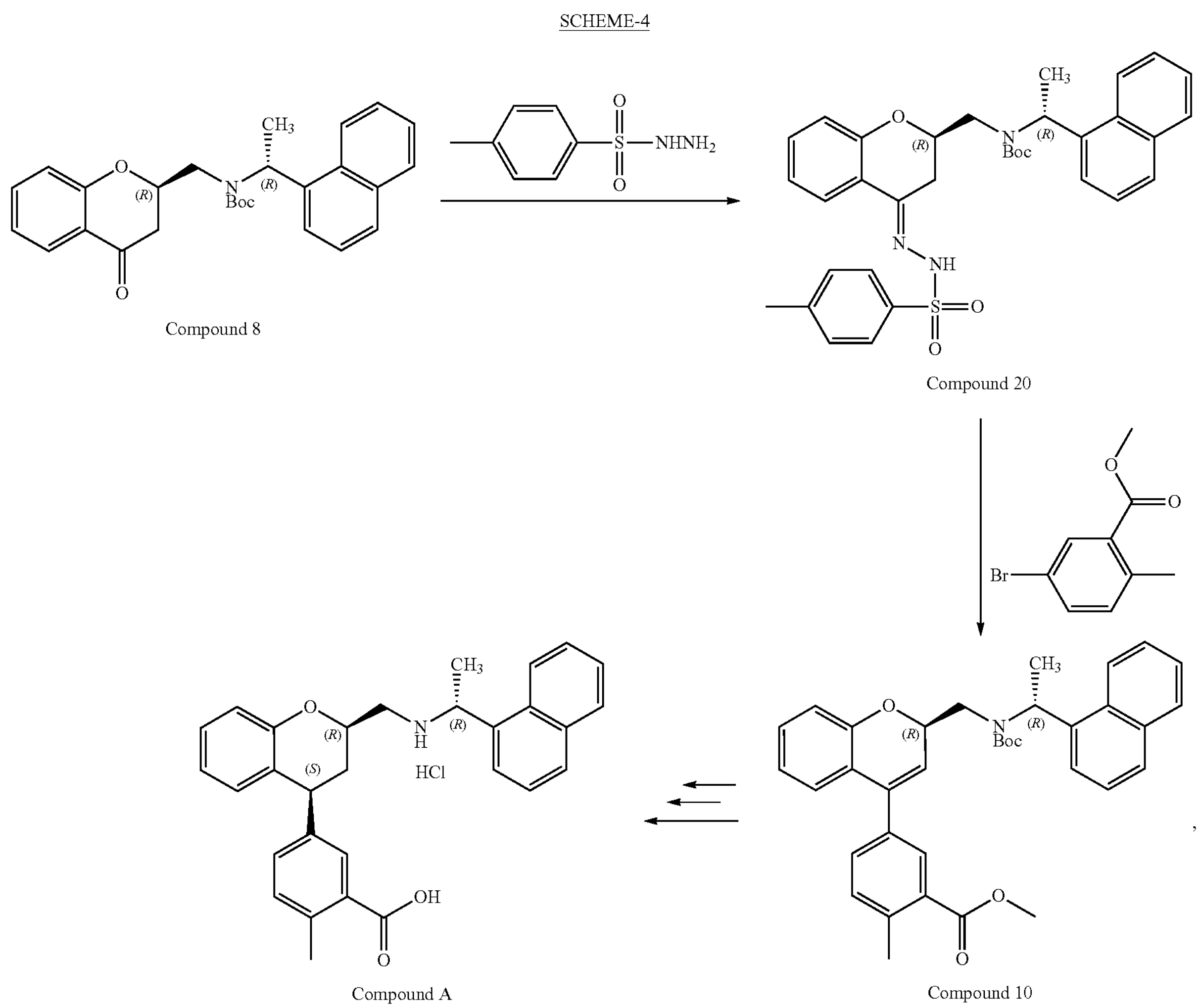

which comprises:

a) reacting (tert-butyl (1-(naphthalen-1-yl)ethyl)((4-oxochroman-2-yl)methyl)carbamate (Compound 8) with one or more sulfonohydrazides (such as, but not limited to, 4-methylbenzenesulfonohydrazide 4-ethylbenzenesulfonohydrazide, thiophene-2-sulfonohydrazide, naphthalene-2-sulfonohydrazide, or a combination thereof) to give tert-butyl (E)-(1-(naphthalen-1-yl)ethyl)((4-(2-tosylhydrazineylidene)chroman-2-yl)methyl)carbamate (Compound 20);

b) coupling tert-butyl (E)-(1-(naphthalen-1-yl)ethyl)((4-(2-tosylhydrazineylidene)chroman-2-yl)methyl)carbamate (Compound 20) with methyl 5-bromo-2-methylbenzoate in the presence of one or more triphosphine ligands (such as, but not limited to, dicyclohexyl-[2-[2,4,6-tri(propan-2-yl)phenyl]phenyl]phosphane, azodicarboxylic acid diethyl ester-triphenylphosphine, dicyclohexyl-[2-[2,4,6-tri(propan-2-yl)phenyl]phenyl]phosphane) or a combination thereof) to obtain methyl 5-((R)-2-(((tert-butoxycarbonyl)((R)-1-(naphthalen-1-yl)ethyl)amino)methyl)-2H-chromen-4-yl)-2-methylbenzoate (Compound 10); and c) converting Compound 10 to Compound A as described in Scheme-1.

DETAILED DESCRIPTION OF THE INVENTION

The invention is not limited to particular compositions, methods, uses, compounds, processes, or methodologies described, as these may vary. The terminology used in this Detailed Description section is for the purpose of describing particular versions or embodiments only, and is not intended to limit the scope of the invention. Unless defined otherwise, all technical and scientific terms used herein have the same meanings as commonly understood by one of ordinary skill in the art. Any methods and materials similar or equivalent to those described herein can be used in the practice or testing of embodiments of the invention, the preferred methods, devices, and materials described herein.

Definitions

For purposes of interpreting the specification, the following definitions will apply and whenever appropriate, terms used in the singular will also include the plural and vice versa.

As used herein, the singular forms “a,” “an” and “the” include plural referents unless the context clearly dictates otherwise. As used herein, the term "about" is intended to qualify the numerical values that it modifies, denoting such a value as variable within a margin of error. When no particular margin of error (such as, for example, standard deviation to a mean value) is recited, the term "about" means plus or minus 10% of the numerical value of the number with which it is being used. For example, "about 50%" means in the range of 45% to 55%. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The term "alkyl" as used herein is a branched or unbranched hydrocarbon group such as methyl, ethyl, n-propyl, isopropyl, n-butyl, isobutyl, t-butyl, pentyl, hexyl, heptyl, octyl, nonyl, decyl, dodecyl, and the like. The alkyl group can also be substituted or unsubstituted. Unless stated otherwise, the term "alkyl" contemplates both substituted and unsubstituted alkyl groups. The alkyl group can be substituted with one or more groups including, but not limited to, alkoxy, alkenyl, alkynyl, cycloalkyl, heterocycloalkyl, aryl, heteroaryl, acyl, amino, alkylamino, aminoalkyl, carboxy, carboxyalkyl, alkoxycarbonyl, alkoxyalkyl, halo, hydroxy, nitro, silyl, alkylthio, alkylsulfonyl, thiol, and the like.

The term "alkenyl" as used herein is a linear monovalent hydrocarbon radical of two to six carbon atoms or a branched monovalent hydrocarbon radical of three to six carbon atoms containing one or two double bonds, e.g., ethenyl, propenyl (including all isomeric forms), 1-methylpropenyl, butenyl (including all isomeric forms), pentenyl (including all isomeric forms), and the like.

The term "alkynyl" as used herein is a linear monovalent hydrocarbon radical of two to six carbon atoms or a branched monovalent hydrocarbon radical of three to six carbon atoms containing one or two triple bonds, e.g., ethynyl, propynyl (including all isomeric forms), 1-methylpropynyl, butynyl (including all isomeric forms), pentynyl (including all isomeric forms), and the like.

The term "cycloalkyl" as used herein is a monovalent saturated monocyclic ring containing three to eight ring carbon atoms, e.g., cyclopropyl, cyclobutyl, cyclopentyl, cyclohexyl, and the like.

The term "heterocyclylalkyl" as used herein is a -(alkylene)-R radical, wherein R is heterocyclyl as defined herein, e.g., pyrrolidinylmethyl, tetrahydrofuranylethyl, pyridinylmethylpiperidinylmethyl, and the like.

The term "aryl" as used herein is a monocyclic or fused bicyclic ring assembly containing 6 to 10 ring carbon atoms wherein each ring is aromatic, e.g., phenyl or naphthyl.

The term "aromatic" as used herein is a moiety wherein the constituent atoms make up an unsaturated ring system, all atoms in the ring system are $sp^2$ hybridized and the total number of pi electrons is equal to 4n+2.

The term "heteroaryl" as used herein is a group or part of a group denotes an aromatic monocyclic or bicyclic moiety of 5 to 10 ring atoms in which one or more, preferably one, two, or three, of the ring atom(s) is (are) selected from nitrogen, oxygen or sulfur, the remaining ring atoms being carbon. Representative heteroaryl rings include, but not limited to, pyrrolyl, furanyl, thienyl, oxazolyl, isoxazolyl, thiazolyl, imidazolyl, triazolyl, tetrazolyl, pyridinyl, pyrimidinyl, pyrazinyl, pyridazinyl, indolyl, benzofuranyl, benzothiophenyl, benzimidazolyl, quinolinyl, isoquinolinyl, quinazolinyl, quinoxalinyl, pyrazolyl, and the like.

The term "acyl" as used herein is a —COR radical where "R" is hydrogen, alkyl, haloalkyl, cycloalkyl, aryl, aralkyl, heteroaryl, heteroaralkyl, or heterocyclyl as defined herein, e.g., formyl, acetyl, trifluoroacetyl, benzoyl, piperazin-1-ylcarbonyl, and the like. When R is alkyl it is referred to in this application as alkylcarbonyl. When R is aryl it is referred to in this application as arylcarbonyl. When R is heteroaryl it is referred to in this application as heteroarylcarbonyl. When R is heterocyclyl it is referred to in this application as heterocyclylcarbonyl.

The term "alkylamino" as used herein is a radical —NHR, wherein "R" is alkyl as defined herein, e.g., methylamino, ethylamino, n-, iso-propylamino, n-, iso-, tert-butylamino, and the like.

The term "alkylthio" as used herein is a —SR radical, wherein "R" is alkyl as defined herein, e.g., methylthio, ethylthio, propylthio, or butylthio, and the like.

The term "alkylsulfonyl" as used herein is a —SO2R radical, wherein "R" is alkyl as defined herein, e.g., methylsulfonyl, ethylsulfonyl, and the like.

The term "alkoxyalkyl" as used herein is a linear monovalent hydrocarbon radical of one to six carbon atoms or a branched monovalent hydrocarbon radical of three to six carbons substituted with at least one alkoxy group, preferably one or two alkoxy groups, as defined herein, e.g., 2-methoxy-ethyl, 1-, 2-, or 3-methoxypropyl, 2-ethoxyethyl, and the like.

The term "alkoxycarbonyl" as used herein is a —C(O)OR radical, wherein "R" is an alkyl group as defined herein, e.g., methoxycarbonyl, ethoxycarbonyl, and the like.

The term "amino" as used herein is an —$NH_2$ radical.

The term "aminoalkyl" as used herein is a linear monovalent hydrocarbon radical of one to six carbon atoms or a branched monovalent hydrocarbon radical of three to six carbons substituted with at least one, preferably one or two, —NRR' where "R" is hydrogen, alkyl, acyl, hydroxyalkyl, alkoxyalkyl, aryl, aralkyl, heteroaryl, heteroaralkyl or heterocyclylalkyl and R' is hydrogen, alkyl, hydroxyalkyl, alkoxyalkyl, aryl, aralkyl, heteroaryl, heteroaralkyl, heterocyclylalkyl, cycloalkyl, cycloalkylalkyl, aminocarbonyl, or aminosulfonyl as defined herein, e.g., aminomethyl, methylaminoethyl, dimethylaminoethyl, 1,3-diaminopropyl, acetylaminopropyl, and the like.

The term "carboxy" as used herein is a —C(O)OH radical.

The term "carboxyalkyl" as used herein is a ton alkyl radical, as defined herein, substituted with at least one, preferably one or two, —C(O)OH group(s), e.g., carboxymethyl, carboxyethyl, 1-, 2-, or 3-carboxypropyl, and the like.

The term "halo" as used herein is fluoro, chloro, bromo or iodo.

The term "hydroxy" as used herein is an —OH radical.

Unless otherwise stated, the term "oxo" as used herein is a C(═O) group. Such an oxo group may be a part of either a cycle or a chain in the compounds disclosed in this application.

The term "silyl" as used herein is a silicon radical wherein the silicon is substituted with one to three of hydrogen, halo, alkyl, amino, aryl, or a combination thereof.

The term "pharmaceutically acceptable" as used herein is that which is useful in preparing a pharmaceutical composition that is generally safe, non-toxic and neither biologically nor otherwise undesirable and includes that which is acceptable for veterinary use as well as human pharmaceutical use.

The term "pharmaceutically acceptable salts" as used herein is salts of compounds of this disclosure that are pharmaceutically acceptable, as defined herein, and that possess the desired pharmacological activity. Such salts include acid addition salts formed with inorganic acids, such as hydrochloric acid, hydrobromic acid, sulfuric acid, nitric acid, phosphoric acid, and the like; or with organic acids, such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methylsulfonic acid, ethanesulfonic acid, 1,2-ethanedisulfonic acid, 2-hydroxy-ethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Pharmaceutically acceptable salts also include base addition salts that may be formed when acidic protons present are capable of reacting with inorganic or organic bases. Acceptable inorganic bases include, but not limited to, sodium hydroxide, sodium carbonate, potassium hydroxide, aluminum hydroxide, calcium hydroxide, and the like. Acceptable organic bases include ethanolamine, diethanolamine, triethanolamine, tromethamine, N-methylglucamine, and the like.

The term "isomers" as used herein is compounds of having identical molecular formulae but differ in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are non-superimposable mirror images are termed "enantiomers" or sometimes "optical isomers." A carbon atom bonded to four nonidentical substituents is termed a "chiral center." A compound with one chiral center that has two enantiomeric forms of opposite chirality is termed a "racemic mixture." A compound that has more than one chiral center has 2n−1 enantiomeric pairs, wherein "n" is the number of chiral centers. Compounds with more than one chiral center may exist as either an individual diastereomer or as a mixture of diastereomers, termed a "diastereomeric mixture." When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well-known in the art (see, e.g., "March's Advanced Organic Chemistry, ed. Michael B. Smith, 8th ed., John Wiley & Sons, Inc. (2020)).

As used herein, the term "nonpolar aprotic solvent" or "aprotic nonpolar solvent" refers a liquid which can dissolve non-polar organic compounds and which has does not comprise an acidic proton. Nonpolar aprotic solvents can include, but not be limited to, toluene (methylbenzene), xylene, dioxane, benzene, dichloromethane (CH2Cl2), carbon tetrachloride (CCl4), trichloromethane (CHCl3), methyl tert-butyl ether (MTBE), or a combination thereof.

As used herein, the term "protic polar solvent" or "polar protic solvent" refers to a liquid which can dissolve polar organic compounds, comprises a strong dipole moment, and further comprises a proton bound to an oxygen atom. Protic polar solvents can include, but not be limited to, ethanol, methanol, isopropanol, or a combination thereof.

As used herein, the term "aprotic polar solvent" refers to a liquid which can dissolve polar organic compounds and comprises a strong dipolar moment but does not comprise a proton bound to an oxygen atom. Aprotic polar solvents can include, but not be limited to, dichloromethane, dimethylformamide, tetrahydrofuran, dioxane, or a combination thereof.

As used herein, the term "nonpolar solvent" refers to an organic liquid which can dissolve organic compounds and does not comprise a strong dipole moment. Nonpolar solvents can include, but not be limited to, toluene (methylbenzene), xylene, dioxane, benzene, dichloromethane (CH2Cl2), carbon tetrachloride (CCl4), trichloromethane (CHCl3), methyl tert-butyl ether (MTBE), or a combination thereof.

As used herein, the term "polar solvent" or "organic polar solvent" refers to a liquid which can dissolve compounds, including organic compounds, and comprises a strong dipole moment. Polar solvents can include, but not be limited to, methanol, dichloromethane, ethanol, propanol, ethyl acetate, tetrahydrofuran, dioxane, water, 2-methyltetrahydrofuran (2-Me-THF), toluene (methylbenzene), ethyl acetate, dimethylformamide (DMF), or a combination thereof.

Organic Synthesis

The compounds described herein may be prepared by synthetic organic chemistry processes or methods. Further, in the schemes described herein, where specific bases, acids, reagents, solvents, coupling agents, etc., are mentioned, it is understood that other bases, acids, reagents, solvents, coupling agents etc., unless otherwise specified, may also be used and are therefore included within the scope of the invention. Variations in reaction conditions, for example, temperature and/or duration of the reaction, are also within the scope of the invention. All the isomers of the compounds described in these schemes, unless otherwise specified, are also encompassed within the scope of this invention.

The methods and processes provided herein are as depicted in Schemes 1 to 4. In certain embodiments, when a temperature is indicated in a reaction, the temperature may be varied from about plus or minus 0.1° C., 0.5° C., 1° C., 5° C., or 10° C. Depending upon which solvent is employed in a particular reaction, the optimum temperature may vary. In conducting a reaction provided herein, neither the rate, nor the order, of addition of the reactants is critical unless otherwise indicated. Unless otherwise indicated, reactions are conducted at ambient atmospheric pressure. Unless otherwise indicated, the exact amount of reactants is not critical. In some embodiments, the amount of a reactant may be varied by about 10 mole percent or about 10% by weight. Unless otherwise indicated, the solvents used in the processes provided herein may be selected from those commercially available or otherwise known to those skilled in the art. Appropriate solvents for a given reaction are within the knowledge of the skilled person and include mixtures of solvents. The products obtained by any of the processes provided herein may be recovered by evaporation or extraction, and may be purified by standard procedures, such as distillation or recrystallization.

The inventors have developed alternate synthetic routes to prepare Compound A that involves using novel intermediate that is beyond those described in U.S. Pat. No. 9,598,391 and PCT International Patent Application Publication No. WO2013/124828.

In one aspect, the invention provides for a method or process for the synthesis of 2-methyl-5-((2R,4S)-2-((((R)-1-(naphthalen-1-yl)ethyl)amino)methyl) chroman-4-yl)benzoic acid hydrochloride (Compound A) starting from 4-oxo-4H-chromene-2-carboxylic acid (Compound 1) following the steps comprising:

a) reacting 4-oxo-4H-chromene-2-carboxylic acid (Compound 1) with (R)-1-(naphthalen-1-yl)ethan-1-amine (Compound 2) in the presence of one or more coupling catalysts (such as, but not limited to, propylphosphonic anhydride (T3P), 1-Ethyl-3-(3-dimethylaminopropyl) carbodiimide (EDCI), 1-Ethyl-3-(3-dimethylaminopropyl)carbodiimide hydrochloride (EDCI-HCl), N,N'-Dicyclohexylcarbodiimide (DCC), N,N'-Diisopropylcarbodiimide (DIC), 1-[Bis (dimethylamino)methylene]-1H-1,2,3-triazolo[4,5-b] pyridinium 3-oxide hexafluorophosphate (HATU), 2-(1H-benzotriazol-1-yl)-1,1,3,3-tetramethyluronium hexafluorophosphate (HBTU), or a combination thereof) to obtain (R)—N-(1-(naphthalen-1-yl)ethyl)-4-oxo-4H-chromene-2-carboxamide (Compound 3);

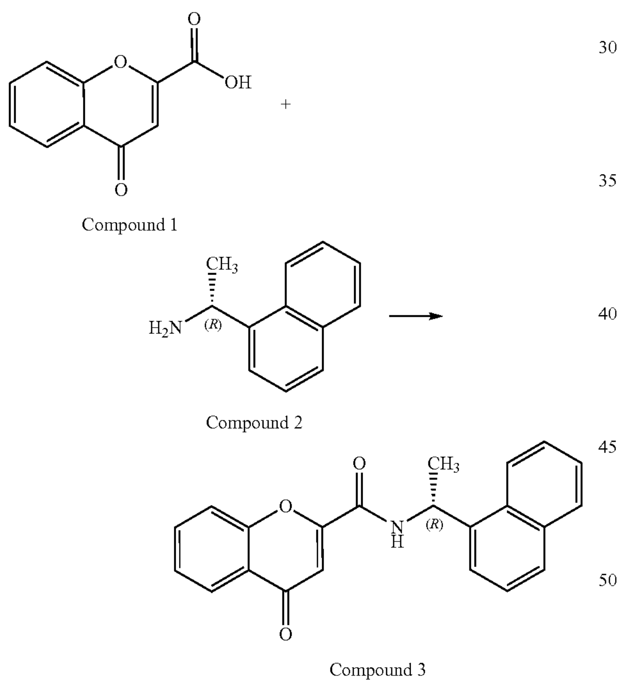

the acid-amine coupling of Compound 1 with Compound 2 to obtain Compound 3 is performed in the presence of propylphosphonic anhydride (T3P). In some aspects, the reaction can be conducted with an acid-amine coupling reagent (such as, but not limited to, propylphosphonic anhydride) with a suitable base (such as, but not limited to, triethyl amine, diisopropylethyl amine, pyridine, 4-dimethylaminopyridine (DMAP), 1,8-Diazabicyclo(5.4.0)undec-7-ene (DBU), 1,5-Diazabicyclo(4.3.0)non-5-ene (DBN), 2,6-di-tert-butyl pyridine) in one or more suitable solvents (such as, but not limited to, a polar aprotic solvent, a polar protic solvent, a non-polar aprotic solvent, tetrahydrofuran, dichloromethane (DCM), tetrahydrofuran (THF), 2-methyltetrahydrofuran (2-Me-THF), toluene (methylbenzene), ethyl acetate, dimethylformamide (DMF), acetonitrile (ACN), 1,4-dioxane, one or more Ethers (such as, but not limited to, dimethyl ether, diethyl ether, tertbutyl methyl ether, diisopropyl ether, di-n-propylether, methyl ethyl ether, or a combination thereof), water, or a combination thereof). In some aspects, the acid-amine coupling of Compound 1 with Compound 2 can be performed using one or more amide-formation coupling catalysts (such as, but not limited to, 1-Ethyl-3-(3-dimethylaminopropyl)carbodiimide (EDCI), 1-Ethyl-3-(3-dimethylaminopropyl) carbodiimide hydrochloride (EDCI-HCl), N,N'-Dicyclohexylcarbodiimide (DCC), N,N'-Diisopropylcarbodiimide (DIC), 1-[Bis (dimethylamino)methylene]-1H-1,2,3-triazolo[4,5-b] pyridinium 3-oxide hexafluorophosphate (HATU), 2-(1H-benzotriazol-1-yl)-1,1,3,3-tetramethyluronium hexafluorophosphate (HBTU), or a combination thereof). In some aspects, the one or more amide-formation coupling catalysts can further comprise one or more acid activators. In some aspects, the one or more acid activators includes, but not limited to, hydroxybenzotriazole (HOBT), 1-Hydroxy-7-azabenzotriazole (HOAt), N-Hydroxysuccinimide (HOSu), 2-Hydroxy-1,2,3-benzotriazin-4(3H)-one (HODhbt), HODhat, N-Hydroxybicyclo[2.2.1] hept-5-ene-2,3-dicarboxylic acid imide (HONB), HODHad, HOCt, HOEt, pyridinium p-toluenesulfonate (PPTS), p-toluenesulfonic acid (TsOH), (7-Azabenzotriazol-1-yloxy) tripyrrolidinophosphonium hexafluorophosphate (PyAOP), (benzotriazol-1-yl-oxytripyrrolidinophosphonium hexafluorophosphate) (PyBOP), AOP, benzotriazol-1-yloxytris(dimethylamino)phosphonium hexafluorophosphate (BOP), Bis(2-oxo-1,3-oxazolidin-3-yl)phosphinic chloride (BOP-Cl), tetramethylfluoroformamidinium hexafluorophosphate (TFFH), BROP, PyBrop, N-ethoxycarbonyl-2-ethoxy-1,2-dihydroquinoline (EEDQ), 1-isobutoxycarbonyl-2-isobutoxy-1,2-dihydroquinoline (IIDQ), CIP, Diphenylphosphoryl azide (DPPA), (1-Cyano-2-ethoxy-2-oxoethylidenaminooxy)dimethylamino-morpholino-carbenium hexafluorophosphate (COMU®), [Ethyl cyano(hydroxyimino)acetato-O2]tri-1-pyrrolidinylphosphonium hexafluorophosphate (PyOxim), 1,1'-Carbonyldiimidazole (CDI), 4-Dimethylaminopyridine (DMAP), PTSA-Cl, Thionyl chloride, Oxalyl chloride, Diethyl chlorophosphate, O,O-Diethyl hydrogen phosphorodithioate, Cyanuric chloride, Cyanuric fluoride, diphenylphosphoryl azide (DPPA), Catecholborane (HBcat), or a combination thereof (the abbreviations used in this application refer to their commonly understood meanings in the field of synthetic organic chemistry);

b) enantioselectively reducing of the double bond of Compound 3 by asymmetric hydrogenation to obtain the optically active (R)—N—((R)-1-(naphthalen-1-yl) ethyl)-4-oxochromane-2-carboxamide (Compound 4) using one or more optically active diphosphine ligands (such as, but not limited to, (R)-(+)-4,4'-Bis(diphenylphosphino)-3,3'-bi(1,2-methylenedioxybenzene) [(R)-SEGPHOS® ], 4,4'-Bis(diphenylphosphino)-3,3'-bi(1,2-methylenedioxybenzene) [SEGPHOS®], (R)-(+)-4,4'-Bis[di(3,5-xylyl)phosphino]-3,3'-bi(1,2-methylenedioxybenzene) [(R)-DM-SEGPHOS®], (R)-(−)-

4,4'-Bis[di(3,5-di-tert-butyl-4-methoxyphenyl)phosphino]-3,3'-bi(1,2-methylenedioxybenzene) [((R)-DTBM-SEGPHOS®)], (R)-(+)-2,2'-Bis(diphenylphosphino)-1,1'-binaphthalene [(R)-BINAP], 2-Dicyclohexylphosphino-2',6'-dimethoxybiphenyl [s-Phos], 5-Bis(diphenylphosphino)-9,9-dimethylxanthene [Xantphos], (2R,3R)-(+)-Bis(diphenylphosphino)butane [R-Chiraphos], 4,4,4',4',6,6'-Hexamethyl-2,2'-spirobichroman-8,8'-diylbis(diphenylphosphane) [SPANphos], Bis(diphenylphosphinoethyl)phenylphosphine [Triphos], (2R,2'R,5R,5'R)-2,2',5,5'-Tetramethyl-1,1'-(o-phenylene)diphospholane [R,R-Me-DuPhos], or a combination thereof);

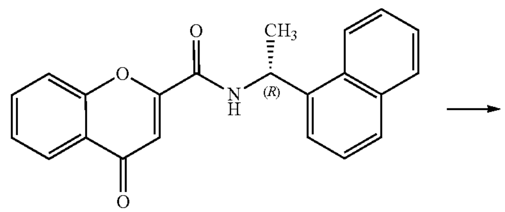

Compound 3

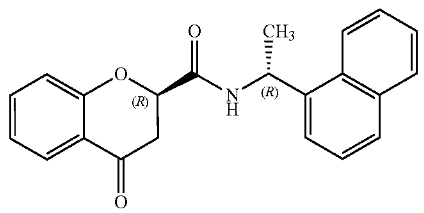

Compound 4 the asymmetric hydrogenation to provide an enantioselective reduction of the double bond of Compound 3 to obtain the optically active Compound 4 can be performed using one or more optically active diphosphine ligands. In some aspects, the one or more optically active diphosphine ligands includes, but not limited to, (R)-(+)-4,4'-Bis(diphenylphosphino)-3,3'-bi(1,2-methylenedioxybenzene) [(R)-SEGPHOS® ], 4,4'-Bis(diphenylphosphino)-3,3'-bi(1,2-methylenedioxybenzene) [SEGPHOS®], (R)-(+)-4,4'-Bis[di(3,5-xylyl)phosphino]-3,3'-bi(1,2-methylenedioxybenzene) [(R)-DM-SEGPHOS®], (R)-(−)-4,4'-Bis[di(3,5-di-tert-butyl-4-methoxyphenyl)phosphino]-3,3'-bi(1,2-methylenedioxybenzene) [((R)-DTBM-SEGPHOS®)], (R)-(+)-2,2',6,6'-Tetramethoxy-4,4'-bis(diphenylphosphino)-3,3'-bipyridine [((R)—P-PHOS™], (R)-(4,4',6,6'-tetramethoxy-[1,1'-biphenyl]-2,2'-diyl)bis(bis(3,5-dimethylphenyl)phosphane) [(R)-GARPHOS™], (R)-(4,4',6,6'-Tetramethoxybiphenyl-2,2'-diyl) bis{bis[3,5-bis(trifluoromethyl)phenyl]phosphine}[(R)-BTFM-GARPHOS™], (R)-[2-[2-bis(3,5-ditert-butyl-4-methoxyphenyl)phosphanyl-4,6-dimethoxyphenyl]-3,5-dimethoxyphenyl]-bis(3,5-ditert-butyl-4-methoxyphenyl)phosphane [(R)-DTBM-GARPHOS™], (R)-(+)-(1,1'-Binaphthalene-2,2'-diyl)bis(diphenylphosphine) [(R)-BIPHEP], (R)-(+)-2,2'-Bis(diphenylphosphino)-1,1'-binaphthalene [(R)-BINAP], 2-Dicyclohexylphosphino-2',6'-dimethoxybiphenyl [s-Phos], 5-Bis(diphenylphosphino)-9,9-dimethylxanthene [Xantphos], (2R,3R)-(+)-Bis(diphenylphosphino)butane [R-Chiraphos], 4,4,4',4',6,6'-Hexamethyl-2,2'-spirobichroman-8,8'-diylbis(diphenylphosphane) [SPANphos], Bis(diphenylphosphinoethyl)phenylphosphine [Triphos], (2R,2'R,5R,5'R)-2,2',5,5'-Tetramethyl-1,1'-(o-phenylene)diphospholane [R,R-Me-DuPhos], or a combination thereof. In some aspects, the one or more optically active diphosphine ligands is any phosphine ligand listed in Downing, J. H. & Smith, M. B., "Phosphorus Ligands," *Comprehensive Coordination Chemistry II*, Section 1.12, pgs. 253-296 (2003), or a combination thereof. In some aspects, the one or more optically active diphosphine ligands is reacted in the presence of one or more metal complexes. In some aspects, the one or more metal complexes includes, but not limited to, Copper(II) acetate ($Cu(OAc)_2$), Palladium(II) acetate ($Pd(OAc)_2$), Zinc acetate ($Zn(OAc)_2$), ruthenium, rhodium metal complexes, or a combination thereof. In some aspects, the one or more metal complexes further comprises one or more phosphine ligands. In some aspects, the one or more phosphine ligands includes, but not limited to, triphenyl phosphine (PPh3), tris(2-carboxyethyl)phosphine) (TCEP), APhos, benzyldiphenylphosphine, or a combination thereof. In some aspects, the one or more phosphine ligands is present with one or more reducing agents. In some aspects, the one or more reducing agents includes, but not limited to, diethoxymethylsilane (DEMS), simple alkylsilanes (which includes, but is not limited, triethylsilane ($Et_3SiH$), $Et_2SiH_2$)), alkylsiloxanes (which includes, but not limited to, polymethylhydrosiloxane (PMHS), DEMS, or tetramethyldisiloxane (TMDS)), phenylsilanes (which includes, but not limited to, phenylsilane ($PhSiH_3$) or diphenylsilane)), halosilanes (which includes, but not limited to, trichlorosilane), hydrosilanes (which includes, but not limited to, tris(trimethylsilyl)silane), or a combination thereof. In some aspects, the asymmetric hydrogenation can be performed in one or more solvents (such as, but not limited to, one or more polar aprotic solvent that includes, but not limited to, tetrahydrofuran (THF), Ethers, methyl-tert-butylether (MTBE), 2-methyltetrahydrofuran (2-Me-THF), acetonitrile, toluene (methylbenzene), dimethyl sulfoxide (DMSO), dimethylformamide (DMF), N-Methyl-2-Pyrrolidone (NMP), dichloromethane, or a combination thereof).

c) reacting Compound 4 with one or more glycols (such as, but not limited to, ethylene glycol propylene glycol, or a combination thereof) in the presence of one or more catalysts (such as, but not limited to, p-toluenesulfonic acid (PTSA), methanesulfonic acid (MSA), trifluoroacetic acid (TFA), tosylic acid (TsOH), pyridinium p-toluenesulfonate (PPTS), orthophosphoric acid, or a combination thereof) in the presence of one or more nonpolar solvents (such as, but not limited to, toluene (methylbenzene), xylene, dioxane, benzene, dichloromethane (CH2Cl2), carbon tetrachloride (CCl4), trichloromethane (CHCl3), methyl tert-butyl ether (MTBE), or a combination thereof), to obtain (R)—N—((R)-1-(naphthalen-1-yl)ethyl)spiro[chromane-4,2'-[1,3]dioxolane]-2-carboxamide (Compound 5),

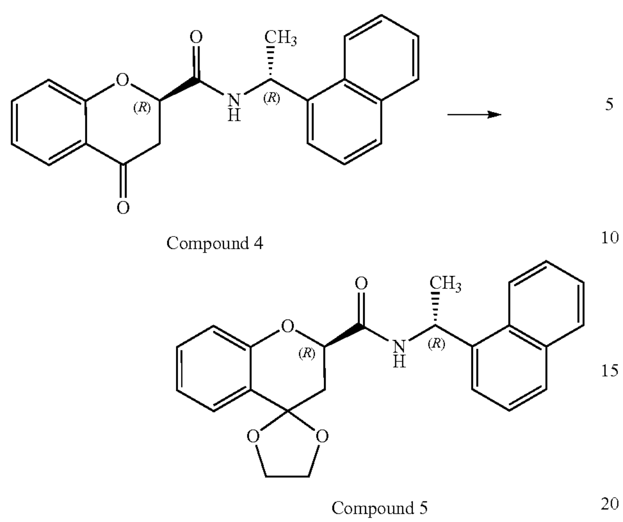

Compound 4

Compound 5 the protection of Compound 4 with one or more glycols (such as, but not limited to, ethylene glycol, propylene glycol, or a combination thereof) to give Compound 5 is performed using one or more glycols (such as, but not limited to, ethylene glycol, propylene glycol, butylene glycol, or a combination thereof) in the presence of one or more catalysts (such as, but not limited to, p-toluenesulfonic acid (PTSA), methanesulfonic acid (MSA), trifluoroacetic acid (TFA), tosylic acid (TsOH), pyridinium p-toluenesulfonate (PPTS), orthophosphoric acid, hydrochloric acid (HCl), sulfuric acid (H2SO4), Solid acid (which can include or exclude Zeolite or resin-bound TsOH), or a combination thereof). In some aspects, the protection of Compound 4 is performed in one or more nonpolar solvents (such as, but not limited to, xylene, dioxane, benzene, dichloromethane (CH2Cl2), carbon tetrachloride (CCl4), trichloromethane (CHCl3), methyl tert-butyl ether (MTBE), toluene (methylbenzene), or a combination thereof). The inventors have recognized that the synthetic schemes they invented and which are described herein involve glycol, preferably ethylene glycol, which is a very low-cost aldehyde protecting group which can be easily added and removed using methods. In combination with an acid-amine coupling step that can also be performed using low-cost catalysts, the synthetic schemes described herein are an economic method to obtain intermediates for synthesizing Compound A. In some aspects, variations on the synthetic scheme provided herein for the protection of the carbonyl group of Compound 4 can be performed using any carbonyl protecting group known in the art, such as, but not limited to, ketals (such as, but not limited to, acetal, thioketals (such as, but not limited to, thioacetal), or a combination thereof). Additional protecting groups may be used in accordance with standard practice, including their addition and removal, for examples, see P. G. M. Wuts, Greene's Protective Groups in Organic Chemistry, 5th ed., John Wiley & Sons, Inc. (2014). In some aspects, Compound 4 can be protected using, for example, 2-mercaptoethanol, 1,2-ethanedithiol, 1,3-propanedithiol, trimethyl orthoformate, triethyl orthoformate, or a combination thereof;

d) reducing the amide group of Compound 5 using one or more reducing agents (such as, but not limited to, Vitride, borane-dimethyl sulphide complex, (Zn(OAc) 2)/DEMS, or a combination thereof) to obtain (R)-1-(naphthalen-1-yl)-N—(((R)-spiro[chromane-4,2'-[1,3]dioxolan]-2-yl)methyl)ethan-1-amine (Compound 6),

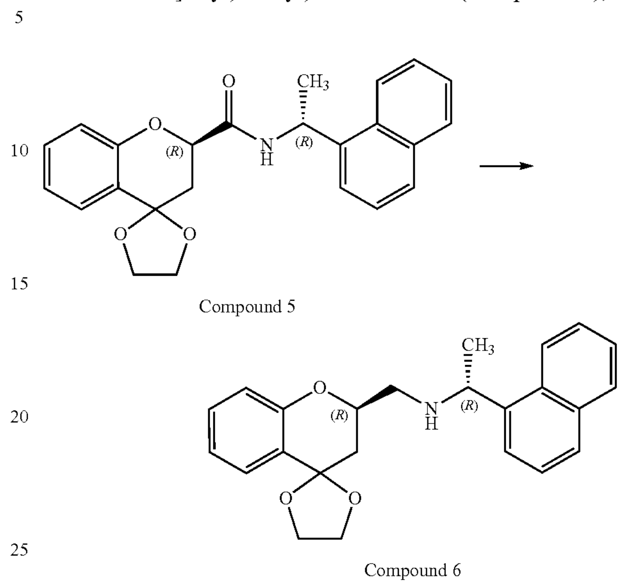

Compound 5

Compound 6 the reduction of Compound 5 to Compound 6 is performed using Vitride™ in toluene and Methyl-THF. In some aspects, reduction of Compound 5 to Compound 6 is performed using borane dimethyl sulfide complex or with $(Zn(OAc)_2)$/DEMS in the presence of one or more solvents such as, but not limited to, THF, methyl THF, toluene, ethanol, methanol, isopropyl alcohol, tert-butyl alcohol, dioxane, or a combination thereof;

e) treating Compound 6 with aqueous acidic media to obtain (R)-2-((((R)-1-(naphthalen-1-yl)ethyl)amino)methyl)chroman-4-one hydrochloride (Compound 7),

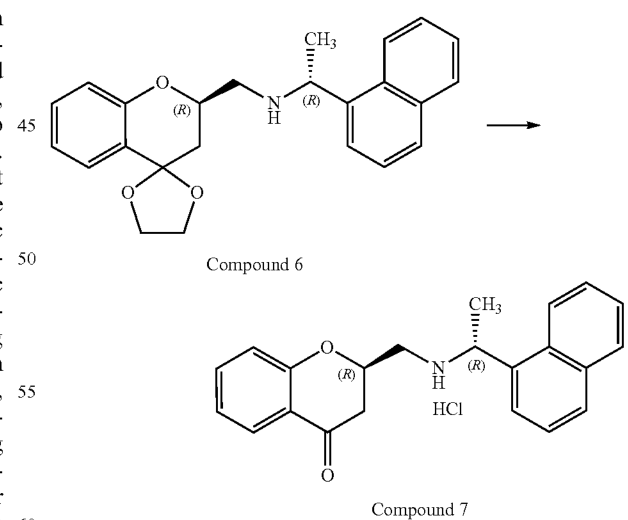

Compound 6

Compound 7 the Compound 6 is deprotected to Compound 7 using aqueous acidic media with one or more polar aprotics or one or more protic solvents. In some aspects, the aqueous acidic media with polar aprotic solvent is aqueous 6N HCl in acetone. In some aspects, the one or more polar aprotic solvents includes, but not limited to, dioxane. In some aspects, the one or more polar protic solvents includes, but not limited to, isopropanol, ethanol, methanol, or a combination thereof.

f) reacting Compound 7 with Boc anhydride (Di-tert-butyl dicarbonate) in the presence of one or more basic catalysts (such as, but not limited to, tripotassium phosphate, triethyl amine, pyridine, DMAP, DBU, DBN, sodium carbonate, sodium-bi-carbonate, sodium carbonate, potassium bi-carbonate, potassium carbonate, or a combination thereof), to obtain tert-butyl ((R)-1-(naphthalen-1-yl)ethyl)(((R)-4-oxochroman-2-yl)methyl) carbamate (Compound 8), Compound 7

Compound 8 the free amino group of Compound 7 is protected using Boc anhydride (Di-tert-butyl dicarbonate) to obtain Compound 8 in the presence of one or more basic catalysts. In some aspects, the amino group of Compound 7 (Compound 7" free base) can also be protected with Boc without base, in the presence of one or more solvents (such as, but not limited to, water, ethanol, methanol, isopropyl alcohol, tert-butyl alcohol, dioxane, THF, or a combination thereof). In some aspects, the one or more basic catalysts includes, but not limited to, triethyl amine, pyridine, DMAP, DBU, DBN, tripotassium phosphate, sodium carbonate, sodium-bi-carbonate, sodium carbonate, potassium bi-carbonate, potassium carbonate, or a combination thereof. In some aspects, the one or more solvents includes, but not limited to, DCM (also referred to herein as $CH_2Cl_2$), water, THF, dioxane, acetonitrile, DMF, toluene, or a combination thereof. In some aspects, the free amino group of Compound 7 can be protected using the one or more amine protecting groups (such as, but not limited to, benzyl, p-methoxybenzyl, carboxybenzoyl (cbz), or a combination thereof), in accordance with standard practice, for examples, see P. G. M. Wuts, Greene's Protective Groups in Organic Chemistry, $5^{th}$ ed., John Wiley & Sons, Inc. (2014).

g) reacting Compound-8 with one or more triflating agents (such as, but not limited to, N-phenyl-bis(trifluoromethanesulfonimide), trifluoromethanesulfonic anhydride, N-(4-tert-Butylphenyl)bis(trifluoromethanesulfonimide), Bis(trifluoromethanesulfonyl)aniline, Comin's reagent, N-(5-Chloro-2-pyridyl)bis(trifluoromethanesulfonimide), trifluoromethanesulfonyl chloride, 4-nitrophenyl trifluoromethanesulfonate, 1-(trifluoromethanesulfonyl)imidazole), or a combination thereof) to give (R)-2-(((tert-butoxycarbonyl)((R)-1-(naphthalen-1-yl)ethyl)amino)methyl)-2H-chromen-4-yl trifluoromethanesulfonate (Compound 9), Compound 8

Compound 9

;

h) coupling Compound 9 with methyl 2-methyl-5-(4,4,5,5-tetramethyl-1,3,2-dioxaborolan-2-yl)benzoate in the presence of one or more palladium catalysts (such as, but not limited to, palladium-tetrakis(triphenylphosphine); palladium(II)bis(triphenylphosphine) dichloride; palladium(0) bis(dibenzylideneacetone); palladium(II)bis(triphenylphosphine) diacetate; [1,1'-bis(diphenylphosphino)ferrocene]dichloropalladium(II)); or a combination thereof) to give methyl-5-((R)-2-(((tert-butoxycarbonyl)((R)-1-(naphthalen-1-yl)ethyl)amino)methyl)-2H-chromen-4-yl)-2-methylbenzoate (Compound 10),

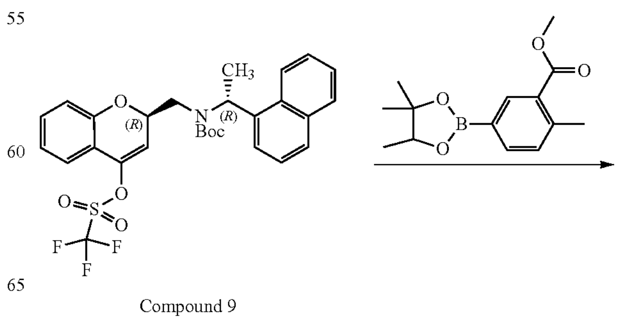

Compound 9

-continued

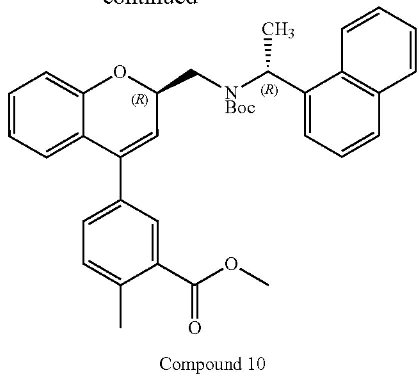

;

Compound 10 i) converting methyl-5-((R)-2-(((tert-butoxycarbonyl)((R)-1-(naphthalen-1-yl)ethyl)amino)methyl)-2H-chromen-4-yl)-2-methylbenzoate (Compound-10) to methyl 5-((2R)-2-(((tert-butoxycarbonyl)((R)-1-(naphthalen-1-yl)ethyl)amino)methyl) chroman-4-yl)-2-methylbenzoate (Compound-11), wherein the conversion is carried out through hydrogenation using palladium charcoal catalyst in methanolic ammonia under optimum hydrogen pressure not more than about 2.0 Kg/cm$^2$, or through treatment with ammonium formate in the presence of palladium charcoal catalyst optionally in the presence of one or more polar solvents, wherein the one or more polar solvents includes, but not limited to, methanol, ethanol, propanol, ethyl acetate, tetrahydrofuran, dioxane, or a combination thereof;

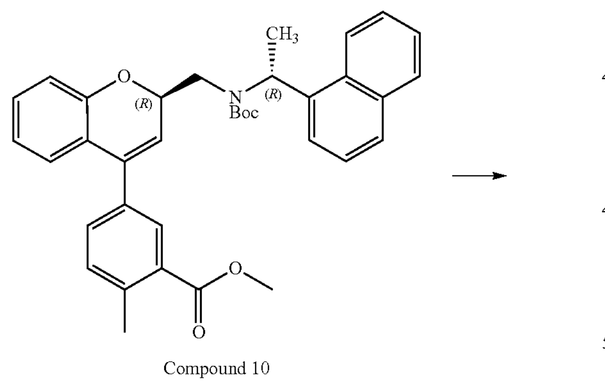

Compound 10

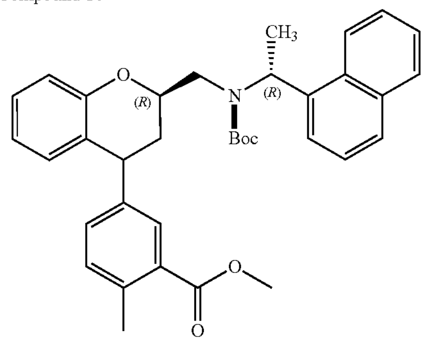

Compound 11 this hydrogenation of Compound 10 to give Compound 11, is carried-out by in a hydrogenation reactor using ammonia in methanolic solution and 5% Pd/C (50% wet and 10% w/w loading), 10% Pd/C or 2% Pd/C under heating at about 28° C. to about 34° C. in methanol or ethylacetate-methanol solvent system. This transfer hydrogenation can be performed with Pd—C catalyst using formate (10 eq) as a hydrogen source, for example, ammonium formate or sodium formate in an aqueous or organic solvent. The reduction of the double bond in Compound 10 to give Compound 11 when carried-out by in a hydrogenation reactor using ammonia in methanolic solution the optimum hydrogen pressure is not more than about 10.0 Kg/cm$^2$, specifically not more than about 5.0 Kg/cm$^2$, more specifically not more than about 2.0 Kg/cm$^2$, wherein optimum hydrogen pressure is between about 0.1 Kg/cm$^2$ to about 2.0 Kg/cm$^2$, preferably optimum hydrogen pressure is between about 1.0 Kg/cm$^2$ to about 2.0 Kg/cm$^2$. The reduction of the double bond in Compound 10 to give Compound 11 is carried out at a temperature between about 10° C. and about 50° C., more preferably at about 30° C. to about 33° C. The reaction can be conducted in one or more suitable solvents (such as, but limited to, halogenated hydrocarbons, $C_6$ to $C_{14}$ aromatic hydrocarbons, $C_1$ to $C_5$ alcohols, $C_2$ to $C_7$ esters, $C_4$ to $C_7$ ethers, $C_1$ to $C_5$ carboxylic acids, water, or a combination thereof). In some aspects, the one or more reaction solvents includes, but not limited to, water, methanol, isopropyl alcohol, dichloromethane, toluene, ethyl acetate, diethyl ether, or a combination thereof.

j) converting Compound 11 to methyl 2-methyl-5-((2R)-2-((((R)-1-(naphthalen-1-yl)ethyl)amino) methyl) chroman-4-yl)benzoate hydrochloride (Compound 12) through Boc-deprotection reaction using aqueous hydrochloric acid, trifluoroacetic acid or trimethyl silyl iodide in the presence of one or more polar solvents, wherein the one or more polar solvents includes, but not limited to, methanol, dichloromethane, ethanol, propanol, ethyl acetate, tetrahydrofuran, dioxane, or a combination thereof,

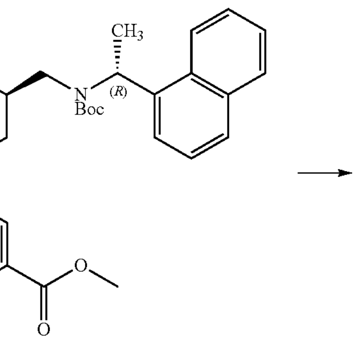

Compound 11

-continued

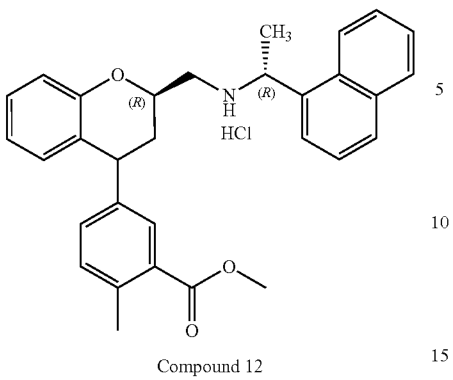

Compound 12

-continued

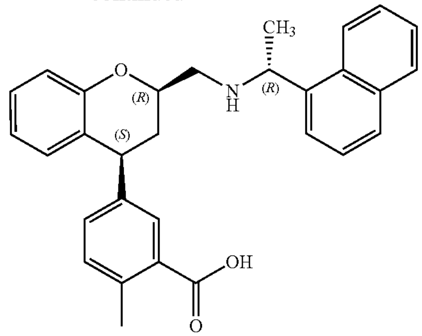

Compound A″ the Boc-deprotection reaction of Compound 11 to give Compound 12 is carried-out by using hydrochloric acid under reflux at about 63° C. in methanol. In some aspects, the concentration of hydrochloric acid is 6 N aqueous HCl. In some aspects, Boc-deprotection can occur using $AlCl_3$, trifluoroacetic acid in dichloromethane, or sequential treatment of trimethyl silyl iodide then methanol. In some aspects, the Boc deprotection can be performed in the presence of one or more cation scavengers. The one or more cation scavengers includes, but not limited to, anisole, thioanisole, or a combination thereof.

k) hydrolyzing the ester group of Compound 12 using one or more hydroxide bases (such as sodium hydroxide, lithium hydroxide, potassium hydroxide, cesium hydroxide, lithium chloride, or a combination thereof) followed by aqueous reaction with the resultant carboxylate salt into the carboxylic acid, and isolation of the pure diastereoisomer by using recrystallization technique with a solvent mixture of one or more protic polar solvents and one or more aprotic polar solvents to give 2-methyl-5-((2R,4S)-2-((((R)-1-(naphthalen-1-yl) ethyl)amino)methyl) chroman-4-yl)benzoic acid (Compound-A"), wherein the one or more protic polar solvents includes, but not limited to, ethanol, methanol, isopropanol, or a combination thereof, and the one or more aprotic polar solvents includes, but not limited to, dichloromethane, dimethylformamide, tetrahydrofuran, or a combination thereof;

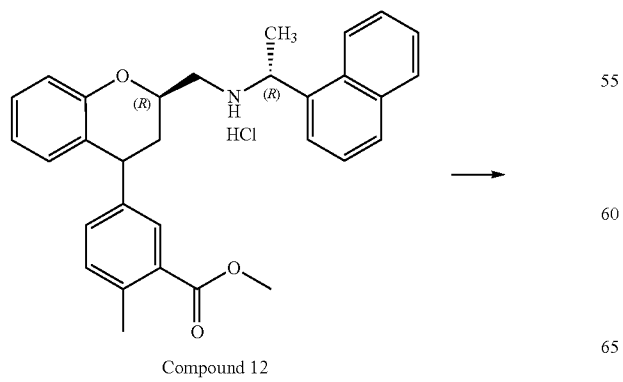

Compound 12 hydrolysis of Compound 12 is carried out by using sodium hydroxide under heating at about 55° C. in a methanol-tetrahydrofuran solvent system. In some aspects, hydrolysis can occur using one or more hydroxide bases (e.g., lithium hydroxide, potassium hydroxide, cesium hydroxide, or a combination thereof), or lithium chloride followed by aqueous reaction with the resultant lithium carboxylate salt into the carboxylic acid. In some aspects, isolation of diastereomerically pure Compound-A" from the crude hydrolysis product of Compound 12 is carried-out by a recrystallization technique using a solvent mixture of one or more protic polar solvents and one or more aprotic polar solvents. In some aspects, the one or more protic polar solvents includes, but not limited to, ethanol, methanol, isopropanol, or a combination thereof. In some aspects, the one or more aprotic polar solvents includes, but not limited to, dichloromethane, dimethylformamide, tetrahydrofuran, or a combination thereof. In some aspects, the recrystallization method involves heating the reaction mixture in a solvent, for example, above 55° C. in a mixture of a solvent-nonsolvent, and allowing the solution to slowly cool to room temperature or below whereby seed crystals of the desired compound (e.g., Compound A") preferentially crystallize while an undesired compound (e.g., Compound 12) essentially remains in solution. Capture of the isolated substantially pure product (e.g., Compound A"), optionally followed by wash with a pre-cooled solution of the solvent-nonsolvent solution, results in substantially purified Compound 12 free of substantially free of impurities. In some aspects, isolation of diastereomerically pure Compound-A" from the crude hydrolysis product of Compound 12 is carried-out by a recrystallization technique using an ethanol:dichloromethane solvent mixture. In some aspects, the (v/v) ratio of ethanol to dichloromethane can range from 1:5 to 5:1; and l) converting Compound-A" to its hydrochloride salt, 2-methyl-5-((2R,4S)-2-((((R)-1-(naphthalen-1-yl) ethyl)amino)methyl) chroman-4-yl)benzoic acid hydrochloride (Compound A) using hydrochloric acid in one or more protic polar solvents (such as, but not limited to, ethanol, methanol, isopropanol, or a combination thereof).

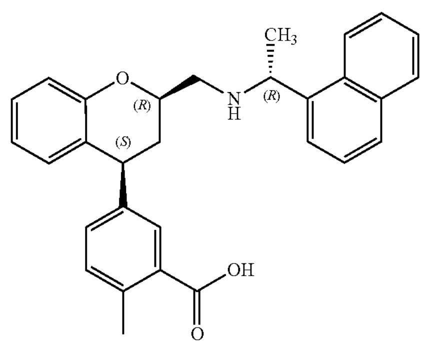

Compound A″

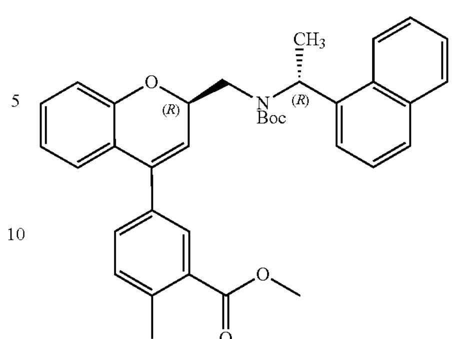

Compound 10

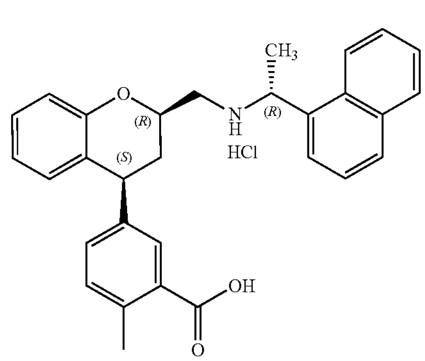

Compound A

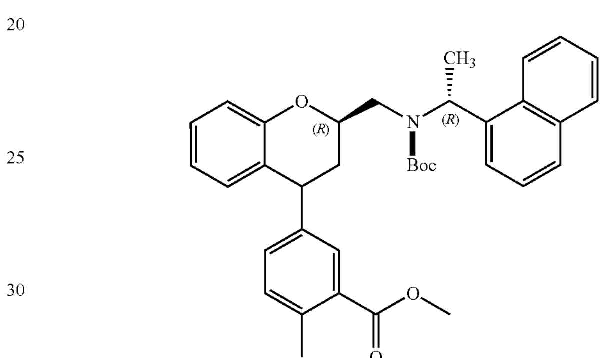

Compound 11 converting Compound-A" to Compound-A is carried out by using acid neutralization with hydrochloric acid. In some aspects, the hydrochloric acid is 2 N aqueous HCl.

In another aspect, a method or process for the manufacture of 2-methyl-5-((2R,4S)-2-((((R)-1-(naphthalen-1-yl) ethyl)amino)methyl) chroman-4-yl)benzoic acid (Compound A") from methyl-5-((R)-2-(((tert-butoxycarbonyl) ((R)-1-(naphthalen-1-yl)ethyl)amino)methyl)-2H-chromen-4-yl)-2-methylbenzoate (Compound 10), wherein the method or process involving the steps of, a) converting methyl-5-((R)-2-(((tert-butoxycarbonyl) ((R)-1-(naphthalen-1-yl)ethyl)amino)methyl)-2H-chromen-4-yl)-2-methylbenzoate (Compound 10) to methyl 5-((2R)-2-(((tert-butoxycarbonyl)((R)-1-(naphthalen-1-yl)ethyl)amino)methyl) chroman-4-yl)-2-methylbenzoate (Compound 11), wherein the conversion is carried out through hydrogenation using palladium charcoal catalyst in methanolic ammonia under optimum hydrogen pressure not more than about 2.0 Kg/cm$^2$, or through treatment with ammonium formate in the presence of palladium charcoal catalyst optionally in the presence of one or more polar solvents, wherein the one or more polar solvents includes, but not limited to, methanol, ethanol, propanol, ethyl acetate, tetrahydrofuran, dioxane, or a combination thereof;

b) converting Compound 11 to methyl 2-methyl-5-((2R)-2-((((R)-1-(naphthalen-1-yl)ethyl)amino) methyl) chroman-4-yl)benzoate hydrochloride (Compound 12) through Boc-deprotection reaction using aqueous hydrochloric acid, trifluoroacetic acid or trimethyl silyl iodide in the presence of one or more polar solvents, wherein the one or more polar solvents includes, but not limited to, methanol, dichloromethane, ethanol, propanol, ethyl acetate, tetrahydrofuran, dioxane, or a combination thereof;

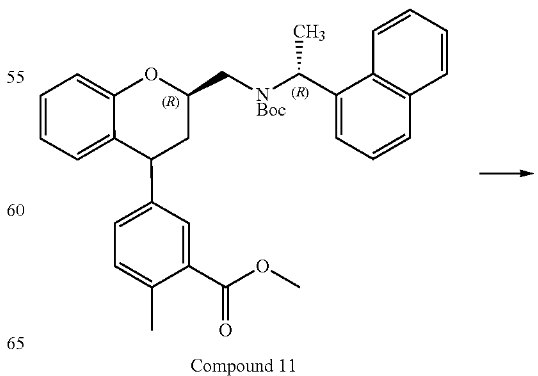

Compound 11

-continued

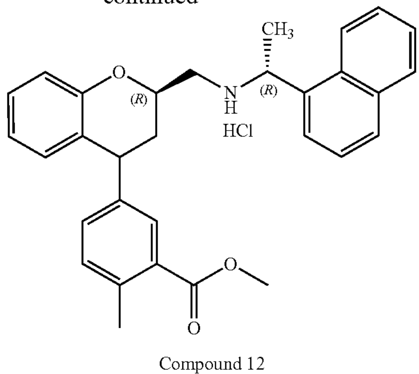

;

Compound 12 and c) hydrolyzing the ester group of Compound 12 using one or more hydroxide bases (such as, but not limited to, sodium hydroxide, lithium hydroxide, potassium hydroxide, cesium hydroxide, lithium chloride, or a combination thereof) followed by aqueous reaction with the resultant carboxylate salt into the carboxylic acid, and isolation of the pure diastereoisomer by using recrystallization technique with a solvent mixture of one or more protic polar solvents and one or more aprotic polar solvents to give 2-methyl-5-((2R,4S)-2-((((R)-1-(naphthalen-1-yl)ethyl)amino)methyl) chroman-4-yl)benzoic acid (Compound A"), wherein the one or more protic polar solvents includes, but not limited to, ethanol, methanol, isopropanol, or a combination thereof, and the one or more aprotic polar solvents includes dichloromethane, dimethylformamide, tetrahydrofuran, or a combination thereof;

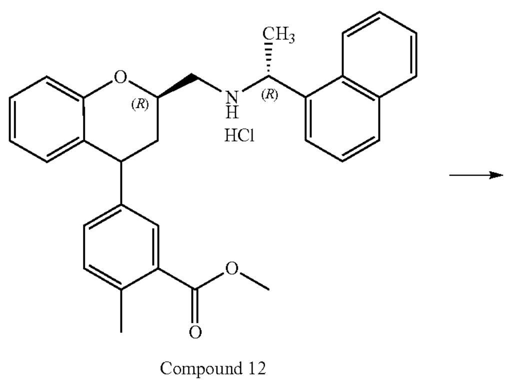

Compound 12

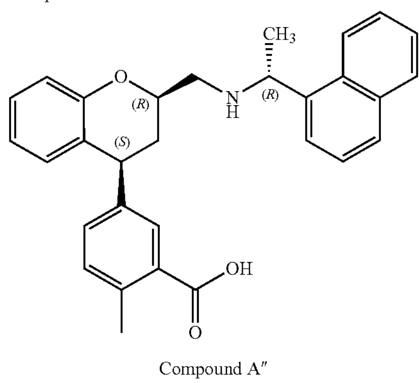

.

Compound A″

In another aspect, the invention provides for a method or process for the manufacture of 2-methyl-5-((2R,4S)-2-((((R)-1-(naphthalen-1-yl)ethyl)amino)methyl) chroman-4-yl)benzoic acid (Compound A"), wherein methyl-5-((R)-2-(((tert-butoxycarbonyl)((R)-1-(naphthalen-1-yl)ethyl) amino)methyl)-2H-chromen-4-yl)-2-methylbenzoate (Compound 10) is manufactured from (R)-2-(((tert-butoxycarbonyl)((R)-1-(naphthalen-1-yl)ethyl)amino)methyl)-2H-chromen-4-yl trifluoromethanesulfonate (Compound 9), by reaction of Compound 9 with methyl 2-methyl-5-(4,4,5,5-tetramethyl-1,3,2-dioxaborolan-2-yl)benzoate in the presence of one or more palladium catalysts (such as, but not limited to, palladium-tetrakis(triphenylphosphine), palladium(II)bis(triphenylphosphine) dichloride; palladium(0) bis (dibenzylideneacetone), palladium(II)bis(triphenylphosphine) diacetate, [1,1'-bis(diphenylphosphino)ferrocene] dichloropalladium(II)), or a combination thereof,

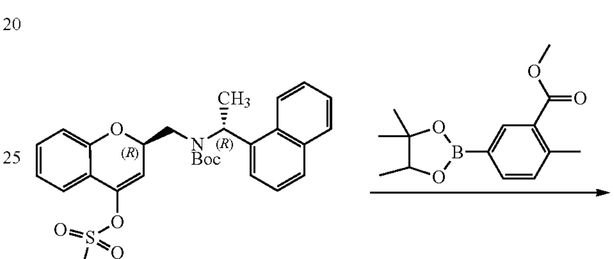

Compound 9

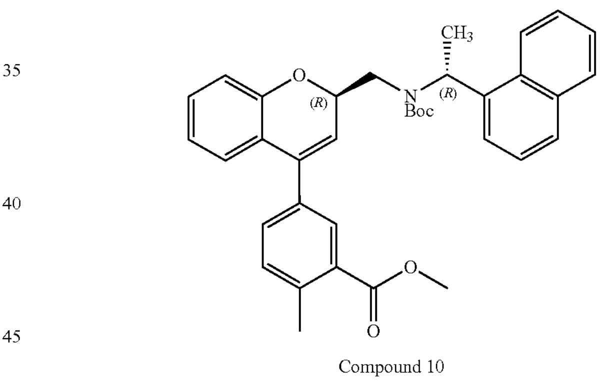

.

Compound 10

In another aspect, the invention provides for a method or process for the manufacture of 2-methyl-5-((2R,4S)-2-((((R)-1-(naphthalen-1-yl)ethyl)amino)methyl) chroman-4-yl)benzoic acid (Compound A"), wherein (R)-2-(((tert-butoxycarbonyl)((R)-1-(naphthalen-1-yl)ethyl)amino) methyl)-2H-chromen-4-yl trifluoromethanesulfonate (Compound 9) is manufactured from tert-butyl ((R)-1-(naphthalen-1-yl)ethyl)(((R)-4-oxochroman-2-yl)methyl) carbamate (Compound 8), by reaction of Compound 8 with one or more triflating agents (such as, but not limited to, N-phenyl-bis(trifluoromethanesulfonimide); trifluoromethanesulfonic anhydride; N-(4-tert-Butylphenyl)bis(trifluoromethanesulfonimide); Bis(trifluoromethanesulfonyl)aniline; Comin's reagent; N-(5-Chloro-2-pyridyl)bis (trifluoromethanesulfonimide); trifluoromethanesulfonyl chloride; 4-nitrophenyl trifluoromethanesulfonate; 1-(trifluoromethanesulfonyl)imidazole), or a combination thereof),

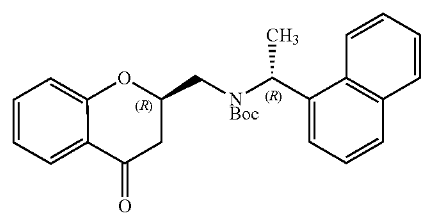

Compound 8

Compound 9

In another aspect, the invention provides for a method or process for the manufacture of 2-methyl-5-((2R,4S)-2-((((R)-1-(naphthalen-1-yl)ethyl)amino)methyl) chroman-4-yl)benzoic acid (Compound A"), wherein tert-butyl ((R)-1-(naphthalen-1-yl)ethyl)(((R)-4-oxochroman-2-yl)methyl) carbamate (Compound 8) is manufactured from (R)-2-((((R)-1-(naphthalen-1-yl)ethyl)amino)methyl) chroman-4-one hydrochloride (Compound 7), by reacting Compound 7 with Boc anhydride (Di-tert-butyl dicarbonate) and tripotassium phosphate, Compound 7

Compound 8

In some aspects, the invention provides for a method or process for the manufacture of 2-methyl-5-((2R,4S)-2-((((R)-1-(naphthalen-1-yl)ethyl)amino)methyl) chroman-4-yl)benzoic acid (Compound A"), wherein (R)-2-((((R)-1-(naphthalen-1-yl)ethyl)amino)methyl) chroman-4-one hydrochloride (Compound 7) is manufactured from (R)-1-(naphthalen-1-yl)-N—(((R)-spiro[chromane-4,2'-[1,3]dioxolan]-2-yl)methyl)ethan-1-amine (Compound 6), by treatment of Compound 6 with aqueous hydrochloric acid,

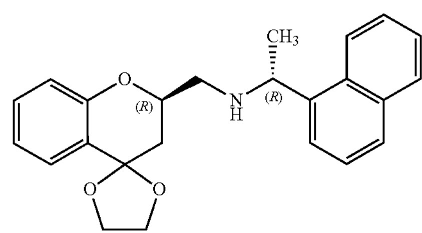

Compound 6

Compound 7

In another aspect, the invention provides for a method or process for the manufacture of 2-methyl-5-((2R,4S)-2-((((R)-1-(naphthalen-1-yl)ethyl)amino)methyl) chroman-4-yl)benzoic acid (Compound A"), wherein (R)-1-(naphthalen-1-yl)-N—(((R)-spiro[chromane-4,2'-[1,3]dioxolan]-2-yl)methyl)ethan-1-amine (Compound 6) is manufactured from (R)—N—((R)-1-(naphthalen-1-yl)ethyl)spiro[chromane-4,2'-[1,3]dioxolane]-2-carboxamide (Compound 5), by reducing the amide group of Compound 5 using one or more reducing agents (such as, but not limited to, Vitride, borane-dimethyl sulphide complex, (Zn(OAc)2)/DEMS, or a combination thereof);

Compound 5

Compound 6

In another aspect, the invention provides for a method or process for the manufacture of 2-methyl-5-((2R,4S)-2-((((R)-1-(naphthalen-1-yl)ethyl)amino)methyl) chroman-4-yl)benzoic acid (Compound A"), wherein (R)—N—((R)-1-(naphthalen-1-yl)ethyl)spiro[chromane-4,2'-[1,3] dioxolane]-2-carboxamide (Compound 5) is manufactured from (R)—N—((R)-1-(naphthalen-1-yl) ethyl)-4-oxochromane-2-carboxamide (Compound 4), by reacting Compound 4 with one or more glycols (such as, but not limited to, ethylene glycol or propylene glycol) in the presence of a catalyst selected from p-toluenesulfonic acid (PTSA), methanesulfonic acid (MSA), trifluoroacetic acid (TFA), tosylic acid (TsOH), pyridinium p-toluenesulfonate (PPTS), orthophosphoric acid, or a combination thereof in the presence of one or more nonpolar solvents (such as, but not limited to, toluene (methylbenzene), xylene, dioxane, benzene, dichloromethane (CH2Cl2), carbon tetrachloride (CCl4), trichloromethane (CHCl3), methyl tert-butyl ether (MTBE), or a combination thereof);

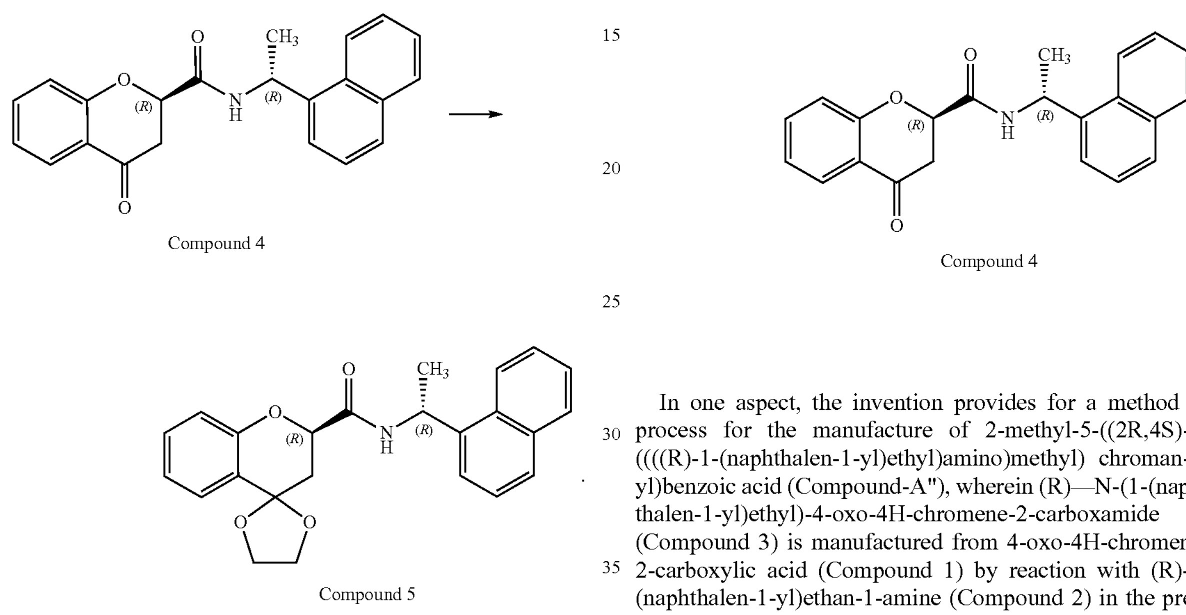

In one aspect, the invention provides for a method or process for the manufacture of 2-methyl-5-((2R,4S)-2-((((R)-1-(naphthalen-1-yl)ethyl)amino)methyl) chroman-4-yl)benzoic acid (Compound-A"), wherein (R)—N—((R)-1-(naphthalen-1-yl) ethyl)-4-oxochromane-2-carboxamide (Compound 4) is manufactured from (R)—N-(1-(naphthalen-1-yl)ethyl)-4-oxo-4H-chromene-2-carboxamide (Compound 3), by enantioselective reduction of the double bond of Compound 3 via asymmetric hydrogenation using one or more optically active diphosphine ligands (such as (R)-(+)-4,4'-Bis(diphenylphosphino)-3,3'-bi(1,2-methylenedioxybenzene) [(R)-SEGPHOS® ], 4,4'-Bis(diphenylphosphino)-3,3'-bi(1,2-methylenedioxybenzene) [SEGPHOS®], (R)-(+)-4,4'-Bis[di(3,5-xylyl)phosphino]-3,3'-bi(1,2-methylenedioxybenzene) [(R)-DM-SEGPHOS®], (R)-(−)-4,4'-Bis[di(3,5-di-tert-butyl-4-methoxyphenyl)phosphino]-3,3'-bi(1,2-methylenedioxybenzene) [((R)-DTBM-SEGPHOS®)], (R)-(+)-2,2'-Bis(diphenylphosphino)-1,1'-binaphthalene [(R)-BINAP], 2-Dicyclohexylphosphino-2',6'-dimethoxybiphenyl [s-Phos], 5-Bis(diphenylphosphino)-9,9-dimethylxanthene [Xantphos], (2R,3R)-(+)-Bis (diphenylphosphino)butane [R-Chiraphos], 4,4,4',4',6,6'-Hexamethyl-2,2'-spirobichroman-8,8'-diylbis (diphenylphosphane) [SPANphos], Bis (diphenylphosphinoethyl)phenylphosphine [Triphos], (2R,2'R,5R,5'R)-2,2',5,5'-Tetramethyl-1,1'-(o-phenylene) diphospholane [R,R-Me-DuPhos], or a combination thereof);

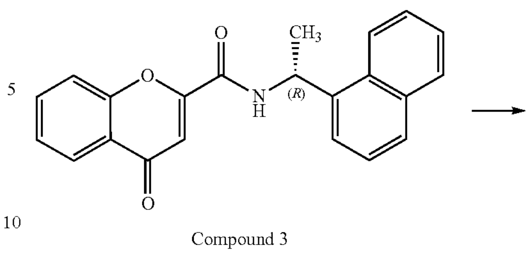

Compound 3

Compound 4

In one aspect, the invention provides for a method or process for the manufacture of 2-methyl-5-((2R,4S)-2-((((R)-1-(naphthalen-1-yl)ethyl)amino)methyl) chroman-4-yl)benzoic acid (Compound-A"), wherein (R)—N-(1-(naphthalen-1-yl)ethyl)-4-oxo-4H-chromene-2-carboxamide (Compound 3) is manufactured from 4-oxo-4H-chromene-2-carboxylic acid (Compound 1) by reaction with (R)-1-(naphthalen-1-yl)ethan-1-amine (Compound 2) in the presence of one or more coupling catalysts (such as, but not limited to, propylphosphonic anhydride (T3P) 1-Ethyl-3-(3-dimethylaminopropyl)carbodiimide (EDCI), 1-Ethyl-3-(3-dimethylaminopropyl)carbodiimide hydrochloride (EDCI-HCl), N,N'-Dicyclohexylcarbodiimide (DCC), N,N'-Diisopropylcarbodiimide (DIC), 1-[Bis(dimethylamino) methylene]-1H-1,2,3-triazolo[4,5-b]pyridinium 3-oxide hexafluorophosphate (HATU), 2-(1H-benzotriazol-1-yl)-1,1,3,3-tetramethyluronium hexafluorophosphate (HBTU), or a combination thereof);

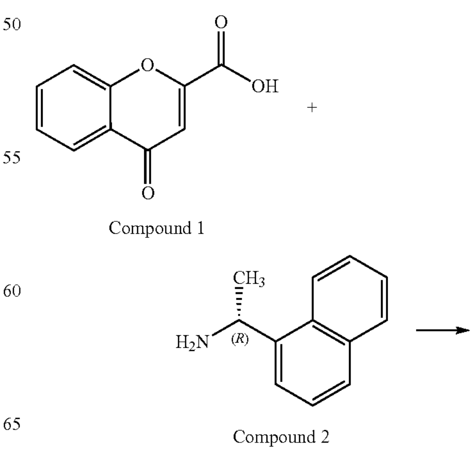

Compound 1

Compound 2

-continued

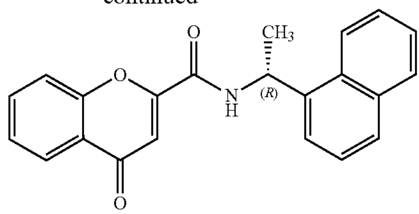

Compound 3

In one aspect, the invention provides for a method or process for the converting 2-methyl-5-((2R,4S)-2-((((R)-1-(naphthalen-1-yl)ethyl)amino)methyl) chroman-4-yl)benzoic acid (Compound-A") to 2-methyl-5-((2R,4S)-2-((((R)-1-(naphthalen-1-yl)ethyl)amino)methyl) chroman-4-yl) benzoic acid hydrochloride (Compound A) using hydrochloric acid in one or more protic polar solvents (such as, but not limited to, ethanol, methanol, isopropanol, or a combination thereof),

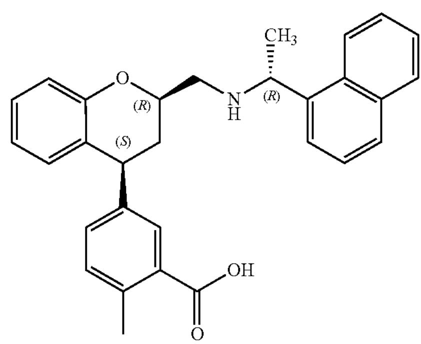

Compound A″

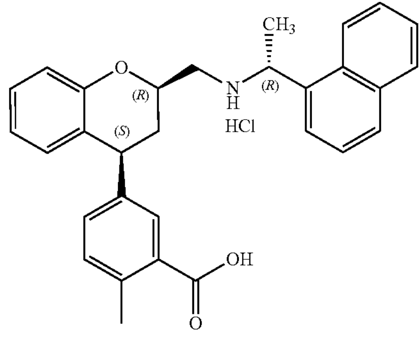

Compound A

In one aspect, the invention provides for a method or process for the manufacture of 2-methyl-5-((2R,4S)-2-((((R)-1-(naphthalen-1-yl)ethyl)amino)methyl) chroman-4-yl)benzoic acid hydrochloride (Compound A) from methyl 4-oxo-4H-chromene-2-carboxylate (Compound 13), wherein the method involving the steps of a) converting methyl 4-oxo-4H-chromene-2-carboxylate (Compound 13) to 2-(hydroxymethyl)-4H-chromen-4-one (Compound 14) by reacting Compound 13 with one or more reducing agents (such as, but not limited to, sodium borohydride (NaBH4), lithium borohydride (LiBH4), lithium aluminum hydride (LiAlH4), sodium cyanoborohydride, NaH, diisobutyl aluminum hydride, metal hydrides, tributyl tin, borane complexes (e.g., BH3-THF), or a combination thereof),

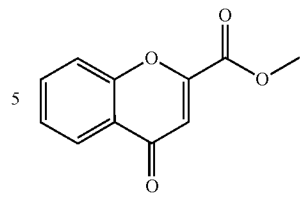

Compound 13

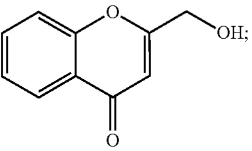

Compound 14 b) converting 2-(hydroxymethyl)-4H-chromen-4-one (Compound 14) to 2-(chloromethyl)-4H-chromen-4-one (Compound 15) by reacting Compound 14 with one or more chlorinating agents (such as, but not limited to, thionyl chloride, sulfonyl chlorides (such as, but not limited to, mesyl chloride, toluenesulfonyl chloride, trichloromethanesulfonic chloride, or a combination thereof), or a combination thereof,

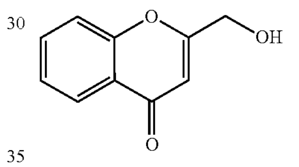

Compound 14

Compound 15 c) coupling 2-(chloromethyl)-4H-chromen-4-one (Compound 15) with (R)-1-(naphthalen-2-yl)ethan-1-amine (Compound 2) to obtain (R)-2-(((1-(naphthalen-1-yl)ethyl)amino)methyl)-4H-chromen-4-one (Compound 16) in the presence of one or more bases (such as, but not limited to, potassium carbonate, potassium iodide, or combination thereof,

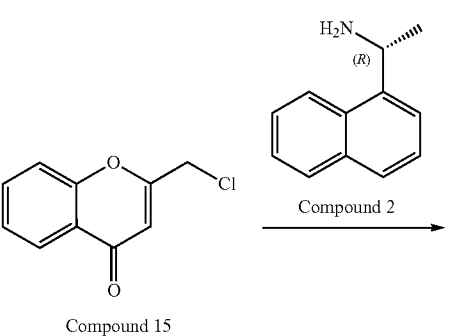

Compound 2

Compound 15

-continued

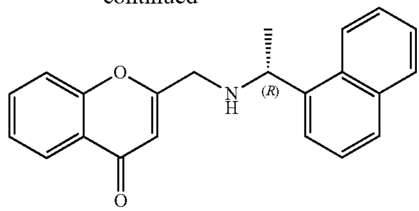

;

Compound 16 d) enantioselectively reducing the double bond of (R)-2-(((1-(naphthalen-1-yl)ethyl)amino)methyl)-4H-chromen-4-one (Compound 16) via asymmetric hydrogenation to obtain the optically active (R)-2-((((R)-1-(naphthalen-1-yl)ethyl) amino)methyl)chroman-4-one (Compound 7"), using one more optically active diphosphine ligand (such as, but not limited to, (R)-(+)-4,4'-Bis(diphenylphosphino)-3,3'-bi(1,2-methylenedioxybenzene) [(R)-SEGPHOS® ], 4,4'-Bis(diphenylphosphino)-3,3'-bi(1,2-methylenedioxybenzene) [SEGPHOS®], (R)-(+)-4,4'-Bis[di(3,5-xylyl)phosphino]-3,3'-bi(1,2-methylenedioxybenzene) [(R)-DM-SEGPHOS®], (R)-(−)-4,4'-Bis[di(3,5-di-tert-butyl-4-methoxyphenyl)phosphino]-3,3'-bi(1,2-methylenedioxybenzene) [((R)-DTBM-SEGPHOS®)], (R)-(+)-2,2'-Bis(diphenylphosphino)-1,1'-binaphthalene [(R)-BINAP], 2-Dicyclohexylphosphino-2',6'-dimethoxybiphenyl [s-Phos], 5-Bis(diphenylphosphino)-9,9-dimethylxanthene [Xantphos], (2R,3R)-(+)-Bis(diphenylphosphino)butane [R-Chiraphos], 4,4,4',4',6,6'-Hexamethyl-2,2'-spirobichroman-8,8'-diylbis(diphenylphosphane) [SPANphos], Bis(diphenylphosphinoethyl)phenylphosphine [Triphos], (2R,2'R,5R,5'R)-2,2',5,5'-Tetramethyl-1,1'-(o-phenylene)diphospholane [R,R-Me-DuPhos], or a combination thereof),

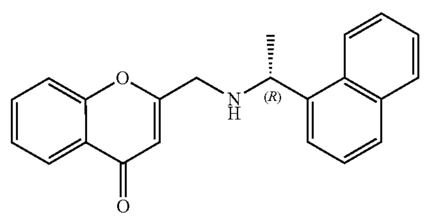

Compound 16

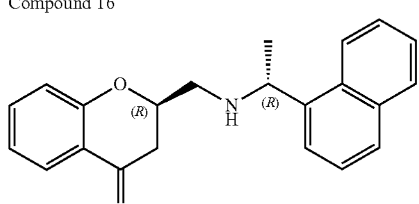

;

Compound 7″ e) treating Compound 7" with Boc anhydride (Di-tert-butyl dicarbonate) in the presence of one or more basic catalyst (such as, but not limited to, tripotassium phosphate, triethyl amine, pyridine, DMAP, DBU, DBN, sodium carbonate, sodium-bi-carbonate, sodium carbonate, potassium bi-carbonate, potassium carbonate, or combination thereof), to obtain Compound 8, Compound 7″

;

Compound 8 f) reacting Compound 8 with one or more triflating agents (such as, but not limited to, N-phenyl-bis(trifluoromethanesulfonimide); trifluoromethanesulfonic anhydride; N-(4-tert-Butylphenyl)bis(trifluoromethanesulfonimide); Bis(trifluoromethanesulfonyl)aniline; Comin's reagent; N-(5-Chloro-2-pyridyl)bis(trifluoromethanesulfonimide); trifluoromethanesulfonyl chloride; 4-nitrophenyl trifluoromethanesulfonate; 1-(trifluoromethanesulfonyl)imidazole); or a combination thereof) to give (R)-2-(((tert-butoxycarbonyl)((R)-1-(naphthalen-1-yl)ethyl)amino)methyl)-2H-chromen-4-yl trifluoromethanesulfonate (Compound 9), Compound 8

;

Compound 9 g) coupling Compound 9 with methyl 2-methyl-5-(4,4,5,5-tetramethyl-1,3,2-dioxaborolan-2-yl)benzoate in the presence of one or more palladium catalysts (such as, but not limited to, palladium-tetrakis(triphenylphosphine); palladium(II)bis(triphenylphosphine) dichloride; palladium(0) bis(dibenzylideneacetone); palladium(II)bis(triphenylphosphine) diacetate; [1,1'-bis(diphenylphosphino)ferrocene]dichloropalladium(II), or a combination thereof) to give methyl-5-((R)-2-(((tert-butoxycarbonyl)((R)-1-(naphthalen-1-yl)ethyl)amino)methyl)-2H-chromen-4-yl)-2-methylbenzoate (Compound 1),

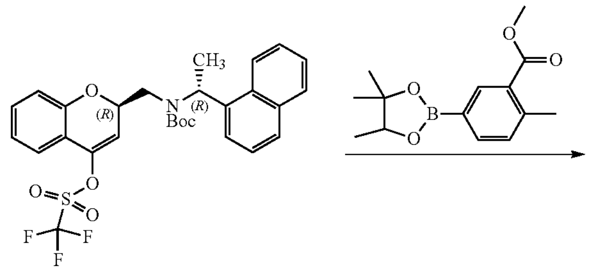

Compound 9

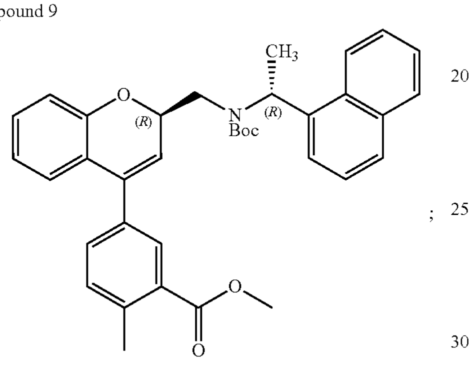

Compound 10 h) converting methyl-5-((R)-2-(((tert-butoxycarbonyl)((R)-1-(naphthalen-1-yl)ethyl)amino)methyl)-2H-chromen-4-yl)-2-methylbenzoate (Compound 10) to methyl 5-((2R)-2-(((tert-butoxycarbonyl)((R)-1-(naphthalen-1-yl)ethyl)amino)methyl) chroman-4-yl)-2-methylbenzoate (Compound 11), wherein the conversion is carried out through hydrogenation using palladium charcoal catalyst in methanolic ammonia under optimum hydrogen pressure not more than about 2.0 about $Kg/cm^2$, or through treatment with ammonium formate in the presence of palladium charcoal catalyst optionally in the presence of one or more polar solvents, wherein the one or more polar solvents includes, but not limited to, methanol, ethanol, propanol, ethyl acetate, tetrahydrofuran, dioxane, or a combination thereof,

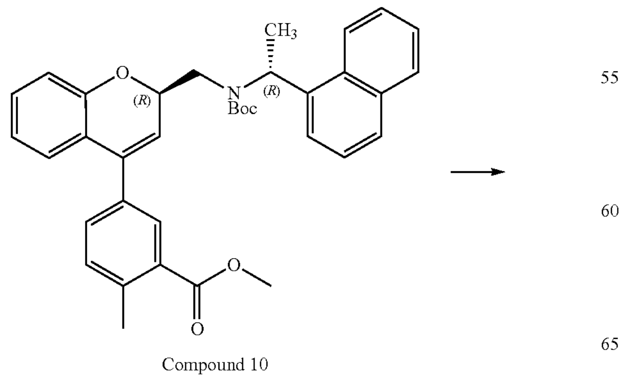

Compound 10

-continued

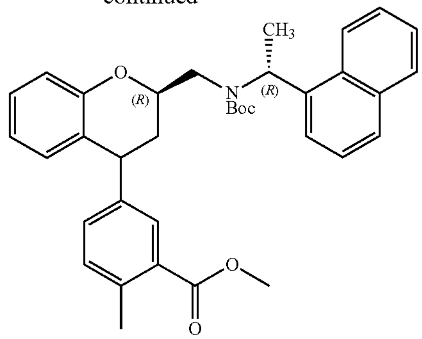

Compound 11 i) converting Compound 11 to methyl 2-methyl-5-((2R)-2-((((R)-1-(naphthalen-1-yl)ethyl)amino) methyl) chroman-4-yl)benzoate hydrochloride (Compound 12) through Boc-deprotection reaction using aqueous hydrochloric acid, trifluoroacetic acid or trimethyl silyl iodide in the presence of one or more polar solvents, wherein the one or more polar solvents includes, but not limited to, methanol, dichloromethane, ethanol, propanol, ethyl acetate, tetrahydrofuran, dioxane, or a combination thereof,

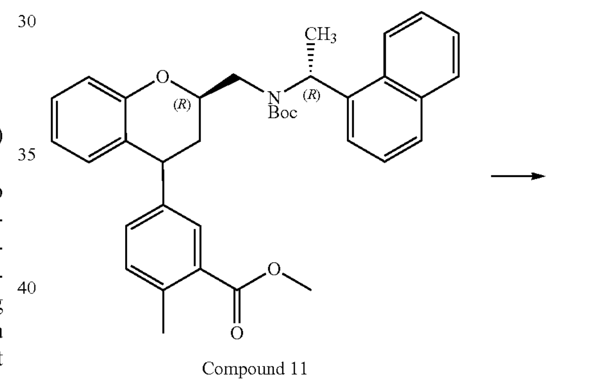

Compound 11

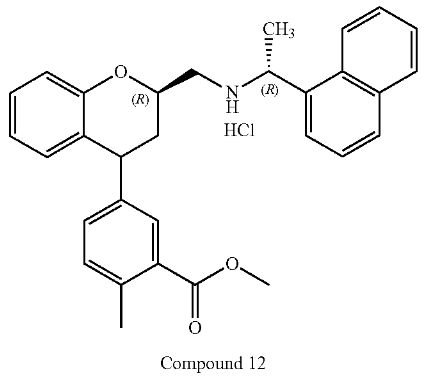

Compound 12 j) hydrolyzing the ester group of Compound 12 using one or more hydroxide bases (such as, but not limited to, sodium hydroxide, lithium hydroxide, potassium hydroxide, cesium hydroxide, lithium chloride, or a combination thereof) followed by aqueous reaction with the resultant carboxylate salt into the carboxylic acid, and isolation of the pure diastereoisomer by using recrystallization technique with a solvent mixture of one or more protic polar solvents and one or more aprotic polar solvents to give 2-methyl-5-((2R,4S)-2-((((R)-1-(naphthalen-1-yl)ethyl)amino)methyl) chroman-4-yl)benzoic acid (Compound A") wherein the one or more protic polar solvents includes, but not limited to, ethanol, methanol, isopropanol, or a combination thereof, and the one or more aprotic polar solvents includes, but not limited to, dichloromethane, dimethylformamide, tetrahydrofuran, or a combination thereof,

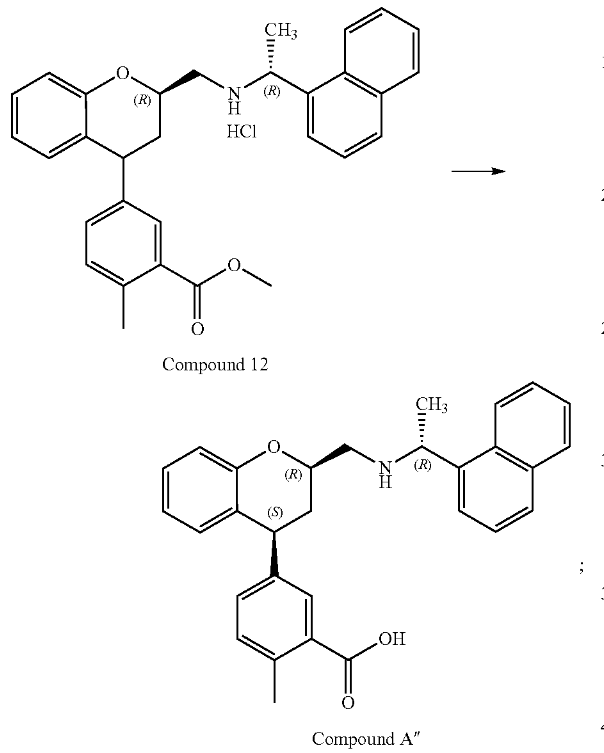

Compound 12

Compound A″ and k) converting Compound A" to its hydrochloride salt, 2-methyl-5-((2R,4S)-2-((((R)-1-(naphthalen-1-yl) ethyl)amino)methyl) chroman-4-yl)benzoic acid hydrochloride (Compound A) using hydrochloric acid in a protic polar solvent can include or exclude: ethanol, methanol, isopropanol, or a combination thereof,

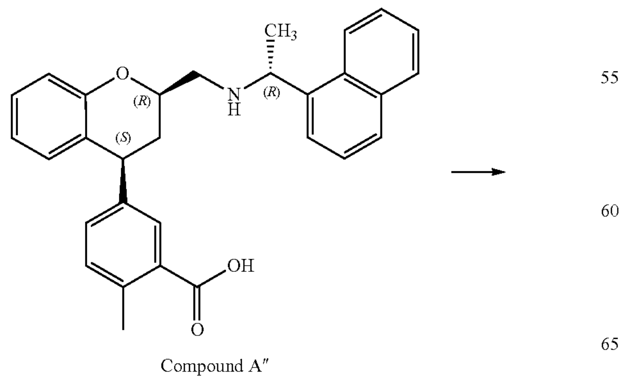

Compound A″

-continued

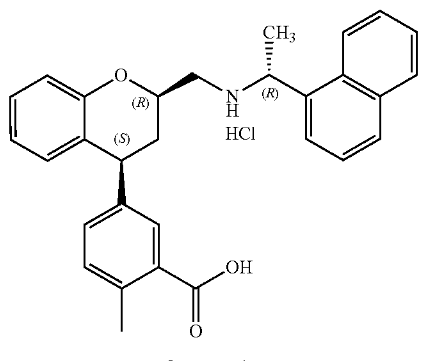

Compound A

In one aspect, the invention provides a method or process for the manufacture of 2-methyl-5-((2R,4S)-2-((((R)-1-(naphthalen-1-yl)ethyl)amino)methyl) chroman-4-yl)benzoic acid (Compound A"), wherein tert-butyl ((R)-1-(naphthalen-1-yl)ethyl)(((R)-4-oxochroman-2-yl)methyl) carbamate (Compound 8) is manufactured from (R)-2-(((1-(naphthalen-1-yl)ethyl)amino)methyl)-4H-chromen-4-one (Compound 16) by following the steps involving a) enantioselectively reducing the double bond of Compound 16 via asymmetric hydrogenation to obtain the optically active (R)-2-((((R)-1-(naphthalen-1-yl)ethyl) amino)methyl)chroman-4-one (Compound 7") using one or more optically active diphosphine ligands (such as, but not limited to, (R)-(+)-4,4'-Bis(diphenylphosphino)-3,3'-bi(1,2-methylenedioxybenzene) [(R)-SEGPHOS® ], 4,4'-Bis(diphenylphosphino)-3,3'-bi(1,2-methylenedioxybenzene) [SEGPHOS®], (R)-(+)-4,4'-Bis[di(3,5-xylyl)phosphino]-3,3'-bi(1,2-methylenedioxybenzene) [(R)-DM-SEGPHOS®], (R)-(−)-4,4'-Bis[di(3,5-di-tert-butyl-4-methoxyphenyl) phosphino]-3,3'-bi(1,2-methylenedioxybenzene) [((R)-DTBM-SEGPHOS®)], (R)-(+)-2,2'-Bis (diphenylphosphino)-1,1'-binaphthalene [(R)-BINAP], 2-Dicyclohexylphosphino-2',6'-dimethoxybiphenyl [s-Phos], 5-Bis(diphenylphosphino)-9,9-dimethylxanthene [Xantphos], (2R,3R)-(+)-Bis(diphenylphosphino)butane [R-Chiraphos], 4,4,4',4',6,6'-Hexamethyl-2,2'-spirobichroman-8,8'-diylbis (diphenylphosphane) [SPANphos], Bis (diphenylphosphinoethyl)phenylphosphine [Triphos], (2R,2'R,5R,5'R)-2,2',5,5'-Tetramethyl-1,1'-(o-phenylene)diphospholane [R,R-Me-DuPhos], or a combination thereof), Compound 16

-continued

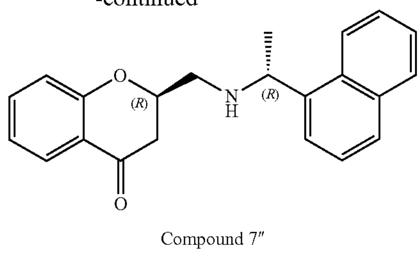

Compound 7″ and b) treating Compound 7" with Boc anhydride (Di-tert-butyl dicarbonate) in the presence of one or more basic catalysts (such as, but not limited to, tripotassium phosphate, triethyl amine, pyridine, DMAP, DBU, DBN, sodium carbonate, sodium-bi-carbonate, sodium carbonate, potassium bi-carbonate, potassium carbonate, or a combination thereof), to obtain Compound 8,

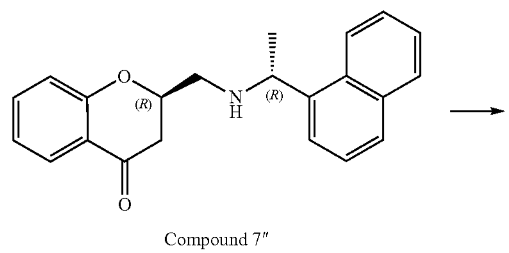

Compound 7″

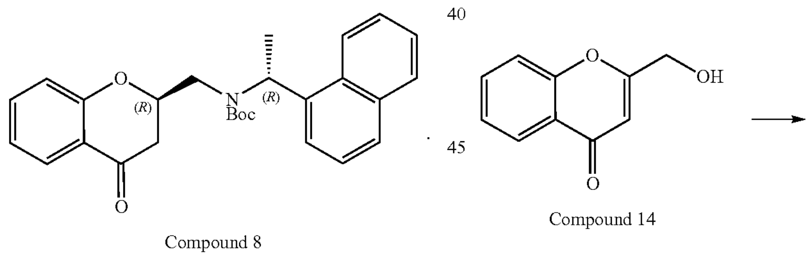

Compound 8

In one aspect, the invention provides a method or process for the manufacture of 2-methyl-5-((2R,4S)-2-((((R)-1-(naphthalen-1-yl)ethyl)amino)methyl) chroman-4-yl)benzoic acid (Compound A"), wherein (R)-2-(((1-(naphthalen-1-yl)ethyl)amino)methyl)-4H-chromen-4-one (Compound 16) is manufactured from 2-(chloromethyl)-4H-chromen-4-one (Compound 15) by coupling Compound 15 with (R)-1-(naphthalen-2-yl)ethan-1-amine (Compound 2) to obtain (R)-2-(((1-(naphthalen-1-yl)ethyl)amino)methyl)-4H-chromen-4-one (Compound 16) in the presence of one or more bases (such as, but not limited to, potassium carbonate, cesium carbonate, potassium iodide, or a combination thereof),

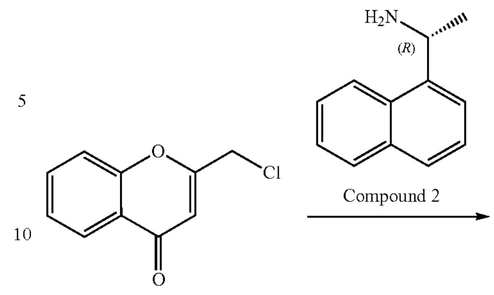

Compound 15

Compound 2

Compound 16

In one aspect, the invention provides a method or process for the manufacture of 2-methyl-5-((2R,4S)-2-((((R)-1-(naphthalen-1-yl)ethyl)amino)methyl) chroman-4-yl)benzoic acid (Compound A"), wherein converting 2-(hydroxymethyl)-4H-chromen-4-one (Compound 14) to 2-(chloromethyl)-4H-chromen-4-one (Compound 15), by reacting Compound 14 with one or more chlorinating agents (such as, but not limited to, thionyl chloride, one or more sulfonyl chlorides (such as, but not limited to, mesyl chloride, toluenesulfonyl chloride, trichloromethanesulfonic chloride, or a combination thereof), or a combination thereof), Compound 14

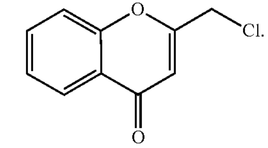

Compound 15

In one aspect, the invention provides a method or process for the manufacture of 2-methyl-5-((2R,4S)-2-((((R)-1-(naphthalen-1-yl)ethyl)amino)methyl) chroman-4-yl)benzoic acid (Compound A"), wherein 2-(hydroxymethyl)-4H-chromen-4-one (Compound 14) manufactured from methyl 4-oxo-4H-chromene-2-carboxylate (Compound 13) by reacting Compound 13 with one or more reducing agents (such as sodium borohydride, borane dimethyl sulfide (2M THF solution), lithium borohydride (LiBH4), lithium aluminum hydride (LiAlH4), or a combination thereof),

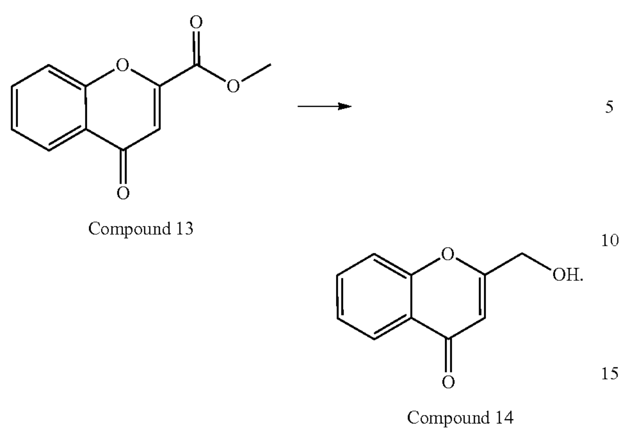
Compound 13

Compound 14

In one aspect, the invention provides for a method or process for the manufacture of 2-methyl-5-((2R,4S)-2-((((R)-1-(naphthalen-1-yl)ethyl)amino)methyl) chroman-4-yl)benzoic acid hydrochloride (Compound A) from (R)-4-oxochromane-2-carboxylic acid (Compound 18), the method or process comprising:

a) coupling (R)-4-oxochromane-2-carboxylic acid (Compound 18) with (R)-1-(naphthalen-1-yl)ethan-1-amine (Compound 2) in the presence of one or more coupling catalysts (such as, but not limited to, propylphosphonic anhydride (T3P) 1-Ethyl-3-(3-dimethylaminopropyl) carbodiimide (EDCI), 1-Ethyl-3-(3-dimethylaminopropyl)carbodiimide hydrochloride (EDCI-HCl), N,N'-Dicyclohexylcarbodiimide (DCC), N,N'-Diisopropylcarbodiimide (DIC), 1-[Bis (dimethylamino)methylene]-1H-1,2,3-triazolo[4,5-b] pyridinium 3-oxide hexafluorophosphate (HATU), 2-(1H-benzotriazol-1-yl)-1,1,3,3-tetramethyluronium hexafluorophosphate (HBTU), or a combination thereof), to obtain (R)—N-(1-(naphthalen-1-yl)ethyl)-4-oxo-4H-chromene-2-carboxamide (Compound 4),

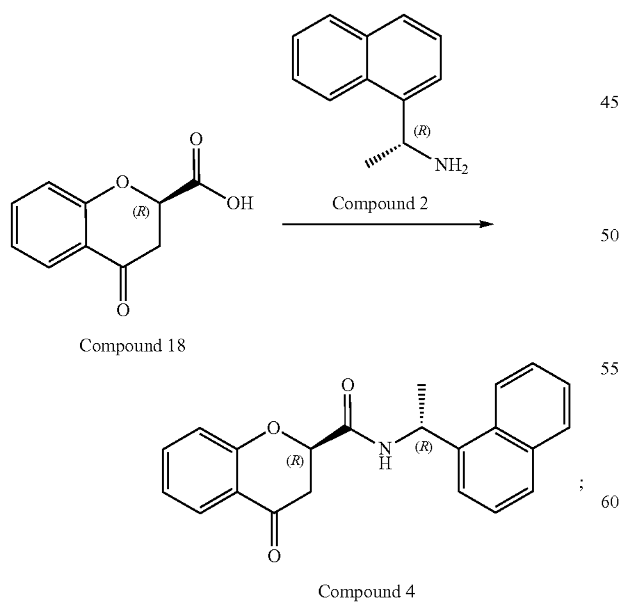
Compound 2

Compound 18

Compound 4 b) reacting Compound 4 with one or more glycols (such as, but not limited to, ethylene glycol, propylene glycol, or a combination thereof) in the presence of one or more catalysts (such as, but not limited to, p-toluenesulfonic acid (PTSA), methanesulfonic acid (MSA), trifluoroacetic acid (TFA), tosylic acid (TsOH), pyridinium p-toluenesulfonate (PPTS), orthophosphoric acid, or a combination thereof) in the presence of one or more nonpolar solvents (such as, but not limited to, toluene (methylbenzene), xylene, dioxane, benzene, dichloromethane (CH2Cl2), carbon tetrachloride (CCl4), trichloromethane (CHCl3), methyl tert-butyl ether (MTBE), or a combination thereof), to obtain (R)—N—((R)-1-(naphthalen-1-yl)ethyl)spiro[chromane-4,2'-[1,3]dioxolane]-2-carboxamide (Compound 5),

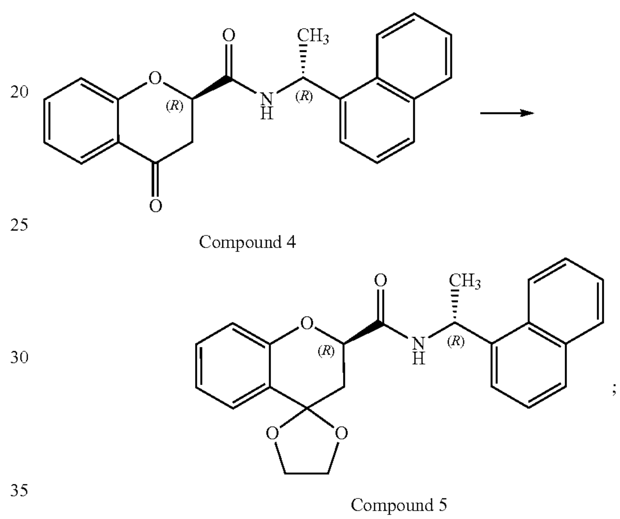
Compound 4

Compound 5 c) reducing the amide group of Compound 5 using one or more reducing agents (such as, but not limited to, Vitride, borane-dimethyl sulphide complex, (Zn(OAc) 2)/DEMS, or a combination thereof) to obtain (R)-1-(naphthalen-1-yl)-N—(((R)-spiro[chromane-4,2'-[1,3] dioxolan]-2-yl)methyl)ethan-1-amine (Compound 6),

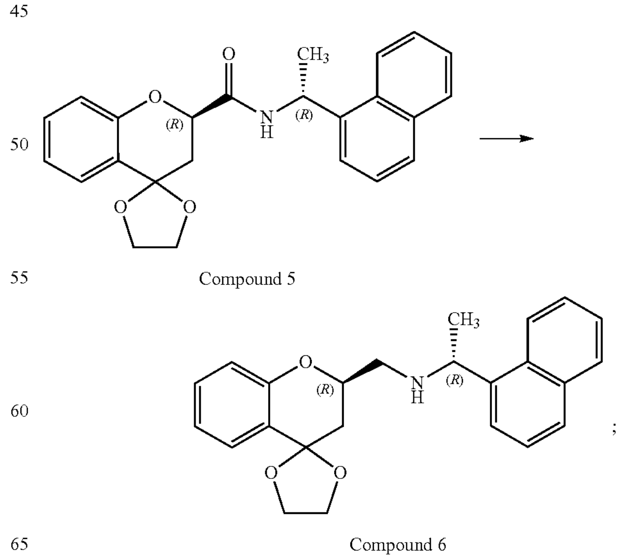
Compound 5

Compound 6 d) treating Compound 6 with aqueous acidic media to obtain (R)-2-((((R)-1-(naphthalen-1-yl)ethyl)amino) methyl)chroman-4-one hydrochloride (Compound 7),

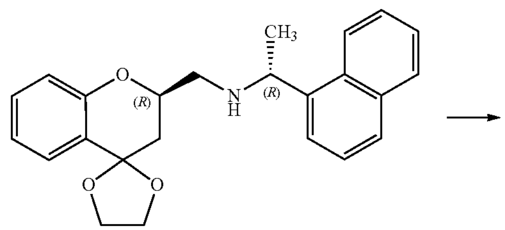

Compound 6

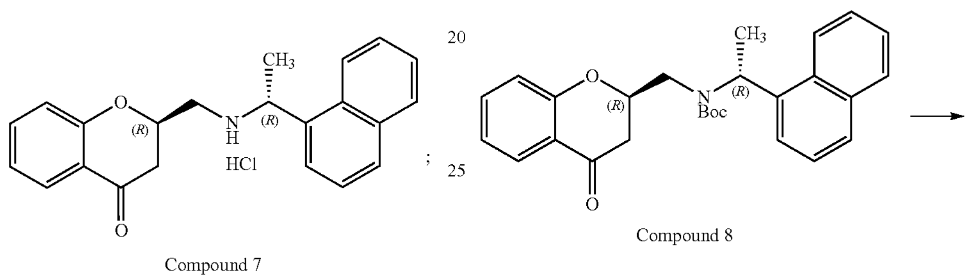

Compound 7

Compound 8 e) reacting Compound 7 with Boc anhydride (Di-tert-butyl dicarbonate) in the presence of one or more basic catalysts (such as, but not limited to, tripotassium phosphate, triethyl amine, pyridine, DMAP, DBU, DBN, sodium carbonate, sodium-bi-carbonate, sodium carbonate, potassium bi-carbonate, potassium carbonate, or a combination thereof), to obtain tert-butyl ((R)-1-(naphthalen-1-yl)ethyl)(((R)-4-oxochroman-2-yl)methyl) carbamate (Compound 8), Compound 7

Compound 8 f) reacting Compound 8 with one or more triflating agent (such as, but not limited to, N-phenyl-bis(trifluoromethanesulfonimide); trifluoromethanesulfonic anhydride; N-(4-tert-Butylphenyl)bis(trifluoromethanesulfonimide); Bis(trifluoromethanesulfonyl)aniline; Comin's reagent; N-(5-Chloro-2-pyridyl)bis(trifluoromethanesulfonimide); trifluoromethanesulfonyl chloride; 4-nitrophenyl trifluoromethanesulfonate; 1-(trifluoromethanesulfonyl)imidazole); or a combination thereof) to give (R)-2-(((tert-butoxycarbonyl)((R)-1-(naphthalen-1-yl)ethyl)amino)methyl)-2H-chromen-4-yl trifluoromethanesulfonate (Compound 9),

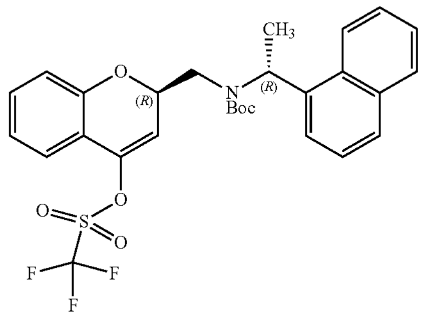

Compound 9 g) coupling Compound 9 with methyl 2-methyl-5-(4,4,5,5-tetramethyl-1,3,2-dioxaborolan-2-yl)benzoate in the presence of one or more palladium catalysts (such as, but not limited to, palladium-tetrakis(triphenylphosphine), palladium(II)bis(triphenylphosphine) dichloride, palladium(0) bis(dibenzylideneacetone), palladium(II)bis(triphenylphosphine) diacetate, [1,1'-bis (diphenylphosphino)ferrocene]dichloropalladium(II), or a combination thereof) to give methyl-5-((R)-2-(((tert-butoxycarbonyl)((R)-1-(naphthalen-1-yl)ethyl) amino)methyl)-2H-chromen-4-yl)-2-methylbenzoate (Compound 10),

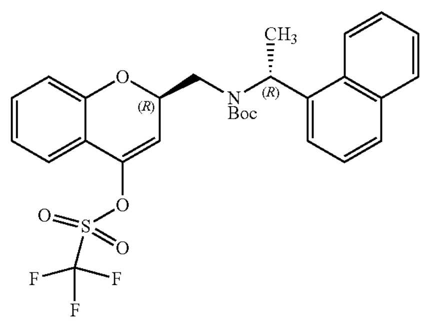

Compound 9

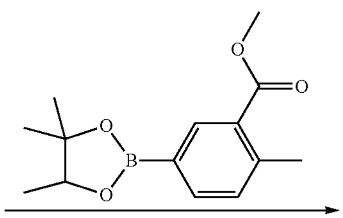

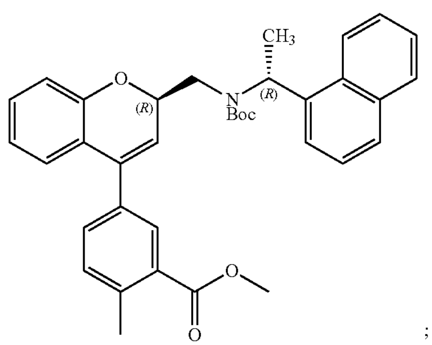

Compound 10

;

h) converting methyl-5-((R)-2-(((tert-butoxycarbonyl)((R)-1-(naphthalen-1-yl)ethyl)amino)methyl)-2H-chromen-4-yl)-2-methylbenzoate (Compound 10) to methyl 5-((2R)-2-(((tert-butoxycarbonyl)((R)-1-(naphthalen-1-yl)ethyl)amino)methyl) chroman-4-yl)-2-methylbenzoate (Compound 11), wherein the conversion is carried out through hydrogenation using palladium charcoal catalyst in methanolic ammonia under optimum hydrogen pressure not more than about 2.0 Kg/cm$^2$, or through treatment with ammonium formate in the presence of palladium charcoal catalyst optionally in the presence of one or more polar solvents, wherein the one or more polar solvents includes, but not limited to, methanol, ethanol, propanol, ethyl acetate, tetrahydrofuran, dioxane, or a combination thereof,

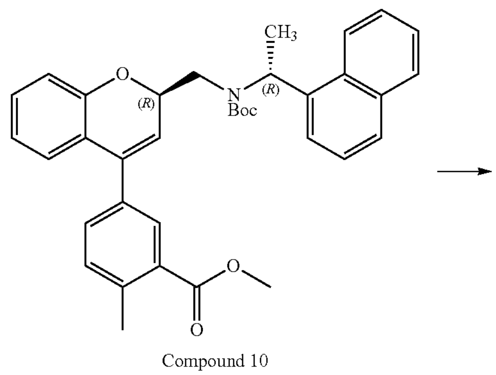

Compound 10

-continued

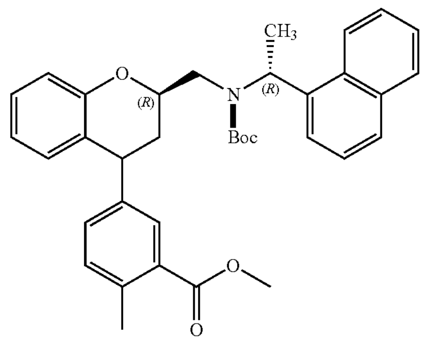

Compound 11

;

i) converting Compound 11 to methyl 2-methyl-5-((2R)-2-((((R)-1-(naphthalen-1-yl)ethyl)amino) methyl) chroman-4-yl)benzoate hydrochloride (Compound 12) through Boc-deprotection reaction using aqueous hydrochloric acid, trifluoroacetic acid or trimethyl silyl iodide in the presence of one or more polar solvents, wherein the one or more polar solvents includes, but not limited to, methanol, dichloromethane, ethanol, propanol, ethyl acetate, tetrahydrofuran, dioxane, or a combination thereof,

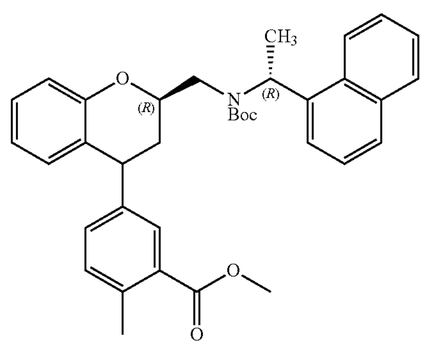
Compound 11

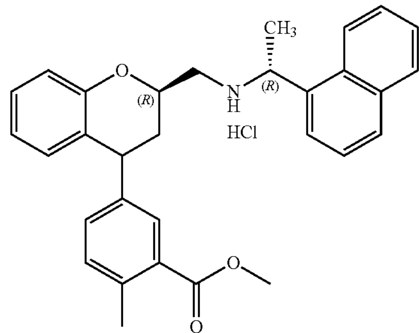
Compound 12 j) hydrolyzing the ester group of Compound 12 using one or more hydroxide bases (such as, but not limited to, sodium hydroxide, lithium hydroxide, potassium hydroxide, cesium hydroxide, lithium chloride, or a combination thereof) followed by aqueous reaction with the resultant carboxylate salt into the carboxylic acid, and isolation of the pure diastereoisomer by using recrystallization technique with a solvent mixture of one or more protic polar solvents and one or more aprotic polar solvents to give 2-methyl-5-((2R,4S)-2-((((R)-1-(naphthalen-1-yl)ethyl)amino)methyl) chroman-4-yl)benzoic acid (Compound-A") wherein the one or more protic polar solvents includes, but not limited to, ethanol, methanol, isopropanol, or a combination thereof, and the one or more aprotic polar solvents includes, but not limited to, dichloromethane, dimethylformamide, tetrahydrofuran, or a combination thereof,

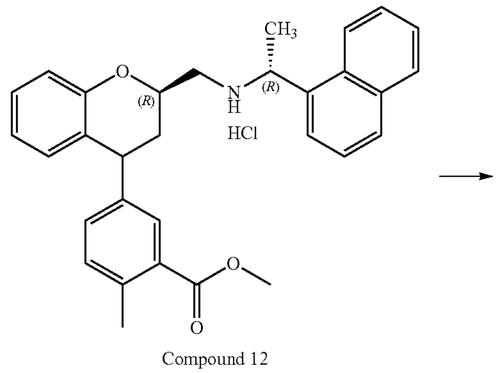
Compound 12

-continued

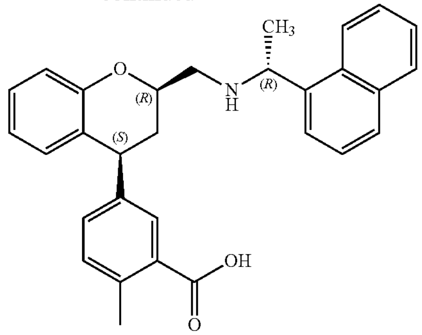
Compound A″ and k) converting Compound A" to its hydrochloride salt, 2-methyl-5-((2R,4S)-2-((((R)-1-(naphthalen-1-yl) ethyl)amino)methyl) chroman-4-yl)benzoic acid hydrochloride (Compound A) using hydrochloric acid in one or more protic polar solvents (such as, but not limited to, ethanol, methanol, isopropanol, or a combination thereof),

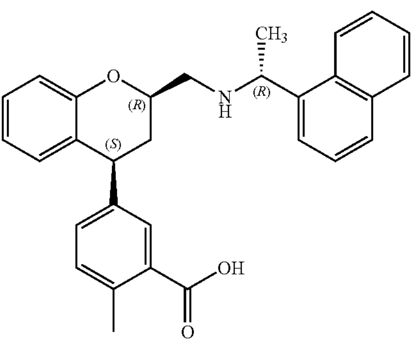
Compound A″

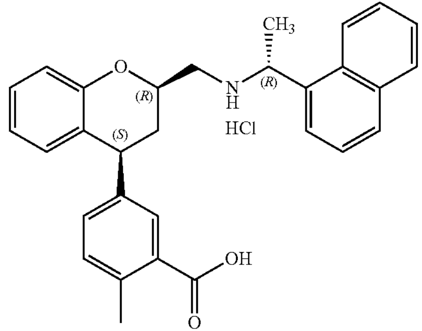
Compound A

In one aspect, the invention provides a method or process for the manufacture of 2-methyl-5-((2R,4S)-2-((((R)-1-(naphthalen-1-yl)ethyl)amino)methyl) chroman-4-yl)benzoic acid hydrochloride (Compound A), wherein (R)-4-oxochromane-2-carboxylic acid (Compound 18) is manufactured from methyl (R)-4-oxochromane-2-carboxylate (Compound 19) using base hydrolysis in one or more polar solvents (such as, but not limited to, water, tetrahydrofuran, dichloromethane (DCM), 2-methyltetrahydrofuran (2-Me-THF), toluene (methylbenzene), ethyl acetate, dimethylformamide (DMF), or a combination thereof) using one or more bases (such as, but not limited to, sodium hydroxide, potassium hydroxide, cesium hydroxide, or a combination thereof),

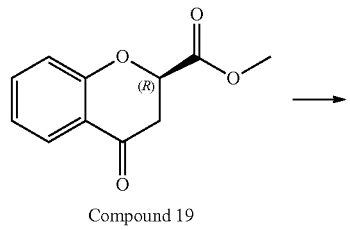
Compound 19

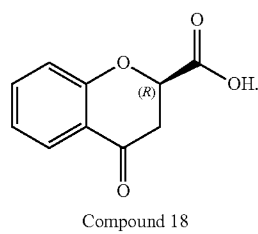
Compound 18

In one aspect, the invention provides for a method or process for the manufacture of 2-methyl-5-((2R,4S)-2-((((R)-1-(naphthalen-1-yl)ethyl)amino)methyl) chroman-4-yl)benzoic acid hydrochloride (Compound A), wherein methyl (R)-4-oxochromane-2-carboxylate (Compound 19) is manufactured from methyl 4-oxo-4H-chromene-2-carboxylate (Compound 13) via asymmetric hydrogenation using one or more optically active diphosphine ligands (such as, but not limited to, (R)-(+)-4,4'-Bis(diphenylphosphino)-3,3'-bi(1,2-methylenedioxybenzene) [(R)-SEGPHOS® ], 4,4'-Bis(diphenylphosphino)-3,3'-bi(1,2-methylenedioxybenzene) [SEGPHOS®], (R)-(+)-4,4'-Bis[di(3,5-xylyl) phosphino]-3,3'-bi(1,2-methylenedioxybenzene) [(R)-DM-SEGPHOS®], (R)-(−)-4,4'-Bis[di(3,5-di-tert-butyl-4-methoxyphenyl)phosphino]-3,3'-bi(1,2-methylenedioxybenzene) [((R)-DTBM-SEGPHOS®)], (R)-(+)-2,2'-Bis(diphenylphosphino)-1,1'-binaphthalene [(R)-BINAP], 2-Dicyclohexylphosphino-2',6'-dimethoxybiphenyl [s-Phos], 5-Bis(diphenylphosphino)-9,9-dimethylxanthene [Xantphos], (2R,3R)-(+)-Bis(diphenylphosphino)butane [R-Chiraphos], 4,4,4',4',6,6'-Hexamethyl-2,2'-spirobichroman-8,8'-diylbis(diphenylphosphane) [SPANphos], Bis(diphenylphosphinoethyl)phenylphosphine [Triphos], (2R,2'R,5R,5'R)-2,2',5,5'-Tetramethyl-1,1'-(o-phenylene) diphospholane [R,R-Me-DuPhos], or a combination thereof),

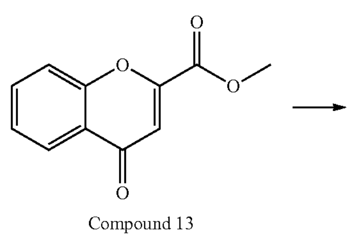
Compound 13

-continued

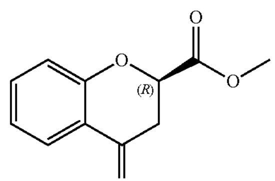
Compound 19

In one aspect, the invention provides for a method or process for the manufacture of 2-methyl-5-((2R,4S)-2-((((R)-1-(naphthalen-1-yl)ethyl)amino)methyl) chroman-4-yl)benzoic acid hydrochloride (Compound A), wherein (R)-4-oxochromane-2-carboxylic acid (Compound 18) is manufactured from (R)-chromane-2-carboxylic acid (Compound 17) by treating Compound 17 with, in the presence of one or more oxidizing agents (such as, but not limited to, KMnO4, MnO2, tert-butyl hydroperoxide-chromium(VI) oxide, potassium peroxomonosulfate, sodium bromate, FeCl3, TBAB-Copper dichloride, AIBN-Oxygen, NaClO2-N-Hydroxyphthalimide, or a combination thereof) in the presence of magnesium sulphate in one or more polar solvents (such as, but not limited to, tetrahydrofuran, dichloromethane (DCM), tedtrahydrofuran (THF), 2-methyltetrahydrofuran (2-Me-THF), toluene (methylbenzene), ethyl acetate, dimethylformamide (DMF), water, acetone, or combination thereof),

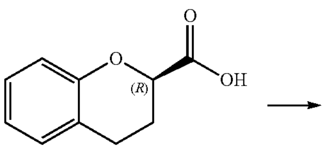
Compound 17

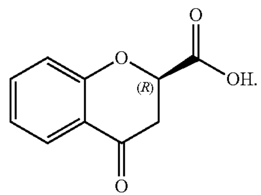
Compound 18

In one aspect, the invention provides for a method or process for the manufacture of 2-methyl-5-((2R,4S)-2-((((R)-1-(naphthalen-1-yl)ethyl)amino)methyl) chroman-4-yl)benzoic acid hydrochloride (Compound A) from tert-butyl ((R)-1-(naphthalen-1-yl)ethyl)(((R,E)-4-(2-tosylhydrazineylidene) chroman-2-yl)methyl)carbamate (Compound 20), wherein the method or process involving the steps of:

a) coupling Compound 20 with methyl 5-bromo-2-methylbenzoate in the presence of dicyclohexyl-[2-[2,4,6-tri(propan-2-yl)phenyl]phenyl]phosphane to obtain methyl 5-((R)-2-(((tert-butoxycarbonyl)((R)-1-(naphthalen-1-yl)ethyl)amino)methyl)-2H-chromen-4-yl)-2-methylbenzoate (Compound 10),

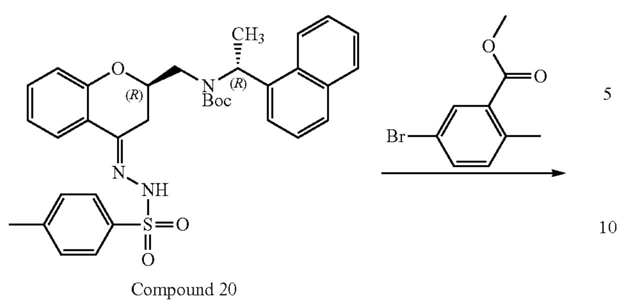

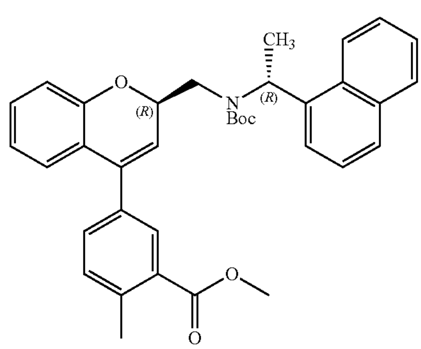

Compound 10 b) converting methyl-5-((R)-2-(((tert-butoxycarbonyl) ((R)-1-(naphthalen-1-yl)ethyl)amino)methyl)-2H-chromen-4-yl)-2-methylbenzoate (Compound 10) to methyl 5-((2R)-2-(((tert-butoxycarbonyl)((R)-1-(naphthalen-1-yl)ethyl)amino)methyl) chroman-4-yl)-2-methylbenzoate (Compound 11), wherein the conversion is carried out through hydrogenation using palladium charcoal catalyst in methanolic ammonia under optimum hydrogen pressure not more than 2.0 about Kg/cm$^2$, or through treatment with ammonium formate in the presence of palladium charcoal catalyst optionally in the presence of one or more polar solvents, wherein the one or more polar solvents includes, but not limited to, methanol, ethanol, propanol, ethyl acetate, tetrahydrofuran, dioxane, or a combination thereof,

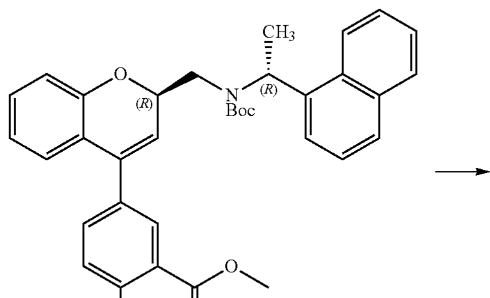

Compound 10

-continued

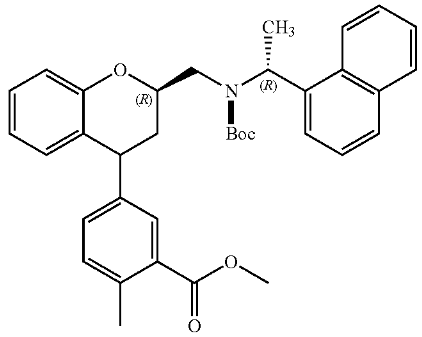

;

Compound 11 c) converting Compound 11 to methyl 2-methyl-5-((2R)-2-((((R)-1-(naphthalen-1-yl)ethyl)amino) methyl) chroman-4-yl)benzoate hydrochloride (Compound 12) through Boc-deprotection reaction using aqueous hydrochloric acid, trifluoroacetic acid or trimethyl silyl iodide in the presence of one or more polar solvents, wherein the one or more polar solvents includes, but not limited to, methanol, dichloromethane, ethanol, propanol, ethyl acetate, tetrahydrofuran, dioxane, or a combination thereof,

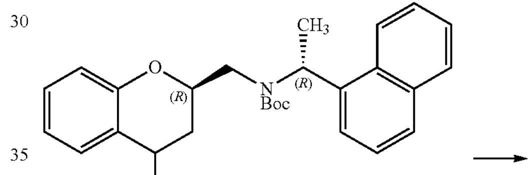

Compound 11

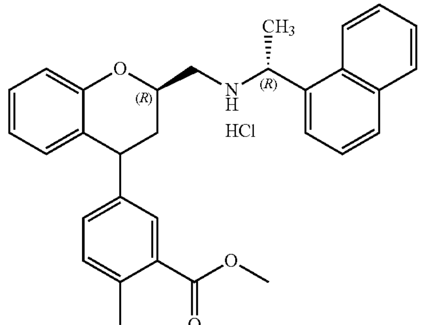

;

Compound 12 d) hydrolyzing the ester group of Compound 12 using one or more hydroxide bases (such as, but not limited to, sodium hydroxide, lithium hydroxide, potassium hydroxide, cesium hydroxide, lithium chloride, or a combination thereof) followed by aqueous reaction with the resultant carboxylate salt into the carboxylic acid, and isolation of the pure diastereoisomer by using recrystallization technique with a solvent mixture of one or more protic polar solvents and one or more aprotic polar solvents to give 2-methyl-5-((2R,4S)-2-((((R)-1-(naphthalen-1-yl)ethyl)amino)methyl) chroman-4-yl)benzoic acid (Compound A"), wherein the one or more protic polar solvents includes, but not limited to, ethanol, methanol, isopropanol, or a combination thereof, and the one or more aprotic polar solvents includes, but not limited to, dichloromethane, dimethylformamide, tetrahydrofuran, or a combination thereof,

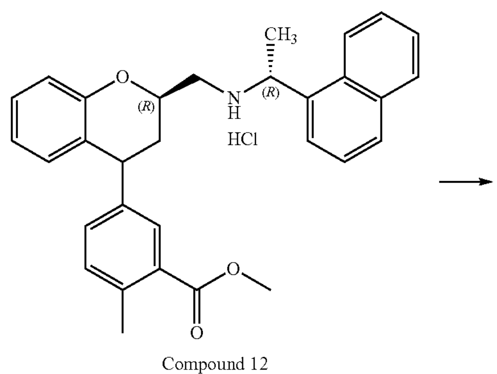

Compound 12

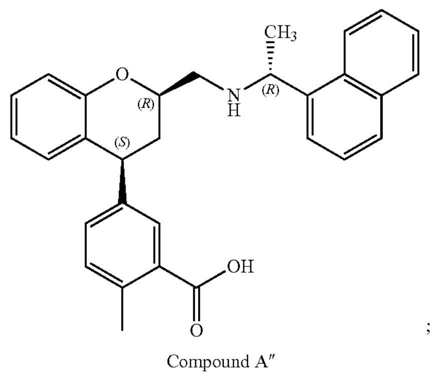

Compound A″ and e) converting Compound A" to its hydrochloride salt, 2-methyl-5-((2R,4S)-2-((((R)-1-(naphthalen-1-yl) ethyl)amino)methyl) chroman-4-yl)benzoic acid hydrochloride (Compound A) using hydrochloric acid in one or more protic polar solvents (such as, but not limited to, ethanol, methanol, isopropanol, or a combination thereof),

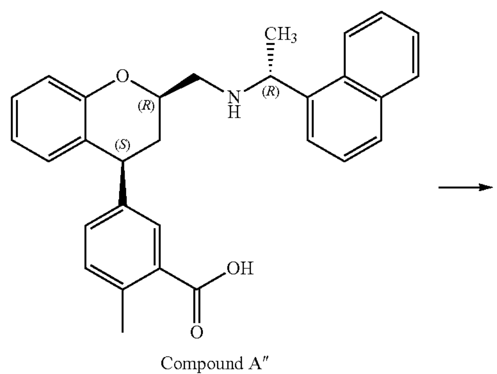

Compound A″

-continued

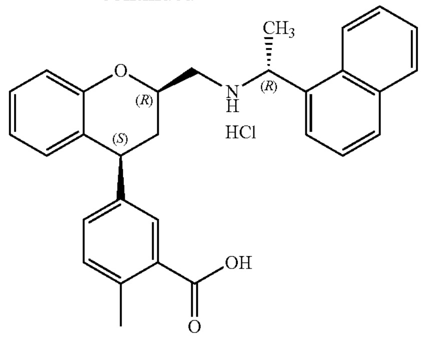

Compound A

In one aspect, the invention provides for a method or process for the manufacture of 2-methyl-5-((2R,4S)-2-((((R)-1-(naphthalen-1-yl)ethyl)amino)methyl) chroman-4-yl)benzoic acid hydrochloride (Compound A), wherein tert-butyl (E)-(1-(naphthalen-1-yl)ethyl)((4-(2-tosylhydrazineylidene)chroman-2-yl)methyl)carbamate (Compound 20) is manufactured from tert-butyl (1-(naphthalen-1-yl)ethyl)((4-oxochroman-2-yl)methyl)carbamate (Compound 8) by reacting Compound 8 with one or more sulfonohydrazides (such as, but not limited to, 4-methylbenzenesulfonohydrazide, 4-ethylbenzenesulfonohydrazide, thiophene-2-sulfonohydrazide, naphthalene-2-sulfonohydrazide, or a combination thereof),

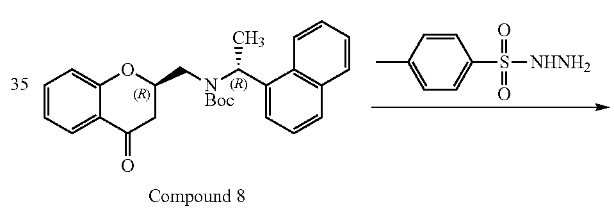

Compound 8

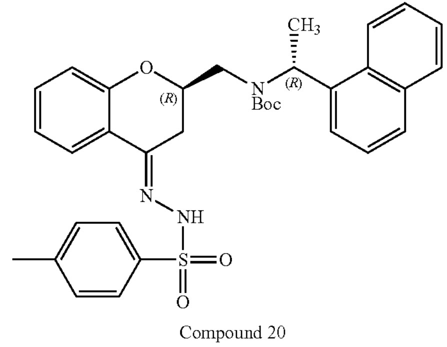

Compound 20

In one aspect, the invention provides a method or process for the manufacture of 2-methyl-5-((2R,4S)-2-((((R)-1-(naphthalen-1-yl)ethyl)amino)methyl) chroman-4-yl)benzoic acid hydrochloride (Compound A) from 4-oxo-4H-chromene-2-carboxylic acid (Compound 1), wherein the method involving the steps of:

a) reacting 4-oxo-4H-chromene-2-carboxylic acid (Compound 1) with (R)-1-(naphthalen-1-yl)ethan-1-amine (Compound 2) in the presence of one or more coupling catalysts (such as, but not limited to, propylphosphonic anhydride (T3P) 1-ethyl-3-(3-dimethylaminopropyl) carbodiimide (EDCI), 1-ethyl-3-(3-dimethylaminopropyl)carbodiimide hydrochloride (EDCI-HCl), N,N'-dicyclohexylcarbodiimide (DCC), N,N'-diisopropylcarbodiimide (DIC), 1-[bis(dimethylamino) methylene]-1H-1,2,3-triazolo[4,5-b]pyridinium 3-oxide hexafluorophosphate (HATU), 2-(1H-benzotriazol-1-yl)-1,1,3,3-tetramethyluronium hexafluorophosphate (HBTU), and a combination thereof), to obtain (R)—N-(1-(naphthalen-1-yl)ethyl)-4-oxo-4H-chromene-2-carboxamide (Compound 3),

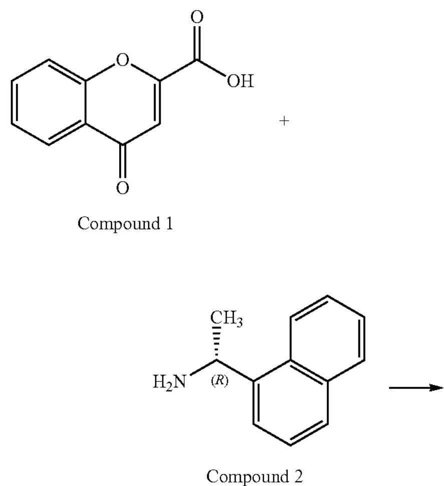

Compound 1

Compound 2

Compound 3 b) enantioselective reduction of the double bond of Compound 3 by asymmetric hydrogenation to obtain the optically active (R)—N—((R)-1-(naphthalen-1-yl) ethyl)-4-oxochromane-2-carboxamide (Compound 4) using one or more optically active diphosphine ligands (such as, but not limited to, (R)-(+)-4,4'-bis(diphenylphosphino)-3,3'-bi(1,2-methylenedioxybenzene) [(R)-SEGPHOS® ], 4,4'-bis(diphenylphosphino)-3,3'-bi(1,2-methylenedioxybenzene) [SEGPHOS®], (R)-(+)-4,4'-Bis[di(3,5-xylyl)phosphino]-3,3'-bi(1,2-methylenedioxybenzene) [(R)-DM-SEGPHOS®], (R)-(−)-4,4'-Bis[di(3,5-di-tert-butyl-4-methoxyphenyl) phosphino]-3,3'-bi(1,2-methylenedioxybenzene) [((R)-DTBM-SEGPHOS®)], (R)-(+)-2,2'-Bis (diphenylphosphino)-1,1'-binaphthalene [(R)-BINAP], 2-Dicyclohexylphosphino-2',6'-dimethoxybiphenyl [s-Phos], 5-Bis(diphenylphosphino)-9,9-dimethylxanthene [Xantphos], (2R,3R)-(+)-Bis(diphenylphosphino)butane [R-Chiraphos], 4,4,4',4',6,6'-Hexamethyl-2,2'-spirobichroman-8,8'-diylbis (diphenylphosphane) [SPANphos], Bis (diphenylphosphinoethyl)phenylphosphine [Triphos], (2R,2'R,5R,5'R)-2,2',5,5'-Tetramethyl-1,1'-(o-phenylene)diphospholane [R,R-Me-DuPhos], or a combination thereof),

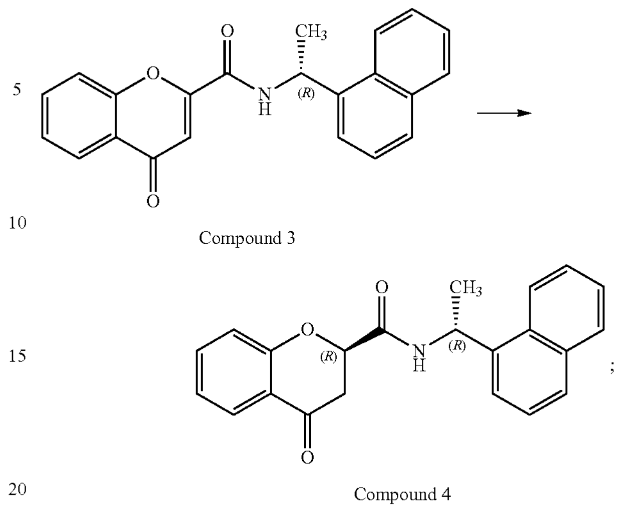

Compound 3

Compound 4 c) reacting Compound 4 with glycol (selected from ethylene glycol or propylene glycol) in the presence of one or more catalysts (such as, but not limited to, p-toluenesulfonic acid (PTSA), methanesulfonic acid (MSA), trifluoroacetic acid (TFA), tosylic acid (TsOH), pyridinium p-toluenesulfonate (PPTS), orthophosphoric acid, or a combination thereof) in the presence of one or more nonpolar solvents (such as, but not limited to, toluene (methylbenzene), xylene, dioxane, benzene, dichloromethane (CH2Cl2), carbon tetrachloride (CCl4), trichloromethane (CHCl3), methyl tert-butyl ether (MTBE), or a combination thereof), to obtain (R)—N—((R)-1-(naphthalen-1-yl)ethyl)spiro[chromane-4,2'-[1,3]dioxolane]-2-carboxamide (Compound 5),

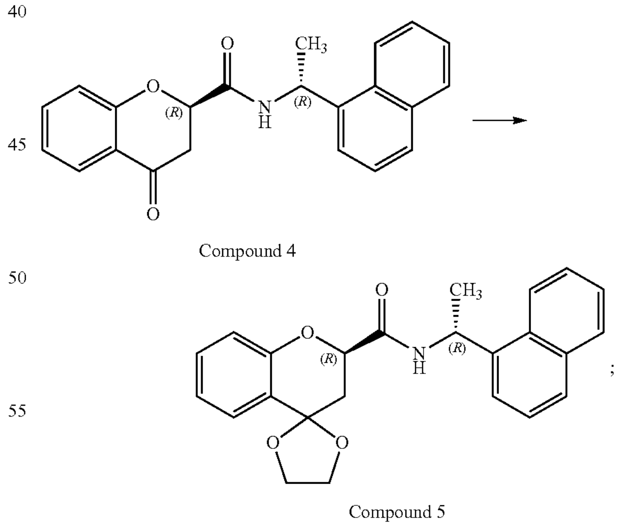

Compound 4

Compound 5 d) reducing the amide group of Compound 5 using one or more reducing agents (such as, but not limited to, Vitride, borane-dimethyl sulphide complex, (Zn(OAc) 2)/DEMS, or a combination thereof) to obtain (R)-1-(naphthalen-1-yl)-N—(((R)-spiro[chromane-4,2'-[1,3] dioxolan]-2-yl)methyl)ethan-1-amine (Compound 6),

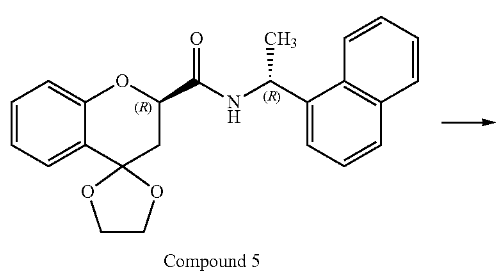
Compound 5

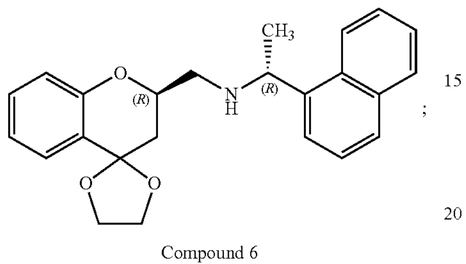
Compound 6 e) treating Compound 6 with aqueous hydrochloric acid to obtain (R)-2-((((R)-1-(naphthalen-1-yl)ethyl)amino) methyl)chroman-4-one hydrochloride (Compound 7),

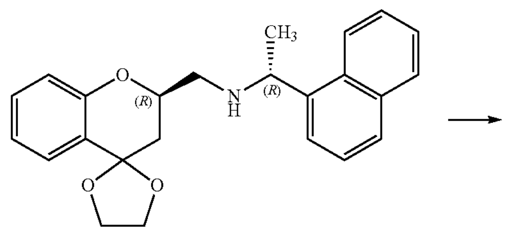
Compound 6

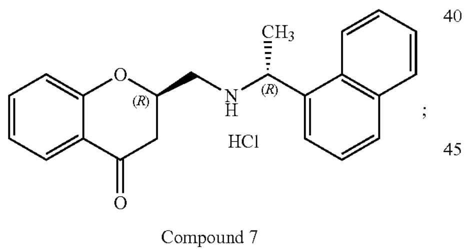
Compound 7 f) reacting Compound 7 with Boc anhydride (Di-tert-butyl dicarbonate) and tripotassium phosphate to obtain tert-butyl ((R)-1-(naphthalen-1-yl)ethyl)(((R)-4-oxochroman-2-yl)methyl) carbamate (Compound 8),

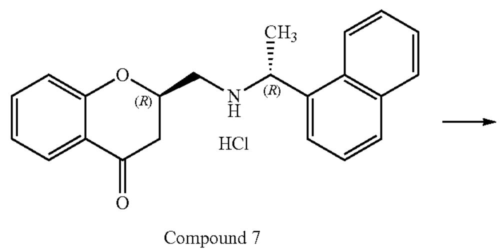
Compound 7

-continued

Compound 8 g) reacting (tert-butyl (1-(naphthalen-1-yl)ethyl)((4-oxochroman-2-yl)methyl)carbamate (Compound 8) with one or more sulfonohydrazides (such as 4-methylbenzenesulfonohydrazide, 4-ethylbenzenesulfonohydrazide, thiophene-2-sulfonohydrazide, naphthalene-2-sulfonohydrazide, or a combination thereof) to give tert-butyl (E)-(1-(naphthalen-1-yl)ethyl)((4-(2-tosylhydrazineylidene)chroman-2-yl)methyl)carbamate (Compound 20),

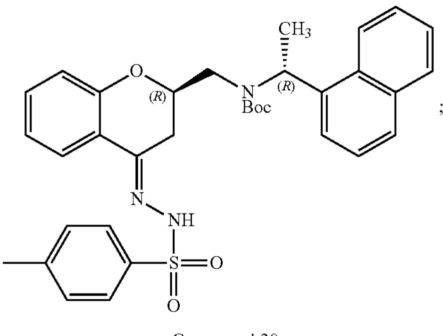
Compound 8

Compound 20 h) coupling tert-butyl (E)-(1-(naphthalen-1-yl)ethyl)((4-(2-tosylhydrazineylidene)chroman-2-yl)methyl)carbamate (Compound 20) with methyl 5-bromo-2-methylbenzoate in the presence of one or more triphosphine ligands (such as, but not limited to, dicyclohexyl-[2-[2,4,6-tri(propan-2-yl)phenyl]phenyl]phosphane or azodicarboxylic acid diethyl ester-triphenylphosphine, dicyclohexyl-[2-[2,4,6-tri(propan-2-yl)phenyl]phenyl] phosphane, or a combination thereof) to obtain methyl 5-((R)-2-(((tert-butoxycarbonyl)((R)-1-(naphthalen-1-yl)ethyl)amino)methyl)-2H-chromen-4-yl)-2-methylbenzoate (Compound 10),

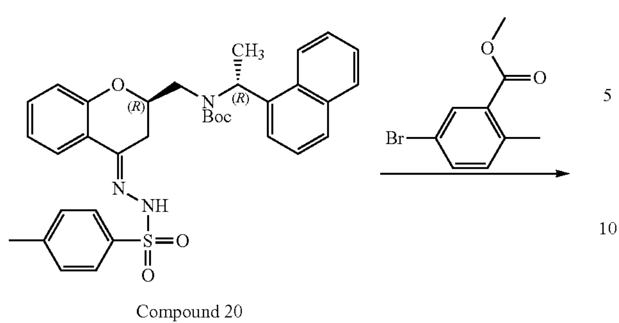

Compound 20

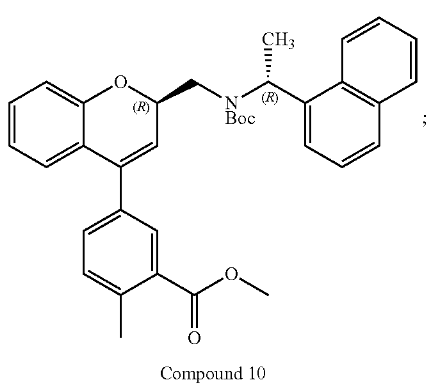

Compound 10 i) converting methyl-5-((R)-2-(((tert-butoxycarbonyl)((R)-1-(naphthalen-1-yl)ethyl)amino)methyl)-2H-chromen-4-yl)-2-methylbenzoate (Compound 10) to methyl 5-((2R)-2-(((tert-butoxycarbonyl)((R)-1-(naphthalen-1-yl)ethyl)amino)methyl) chroman-4-yl)-2-methylbenzoate (Compound 11), wherein the conversion is carried out through hydrogenation using palladium charcoal catalyst in methanolic ammonia under optimum hydrogen pressure not more than about 2.0 $Kg/cm^2$, or through treatment with ammonium formate in the presence of palladium charcoal catalyst optionally in the presence of one or more polar solvents, wherein the one or more polar solvents includes, but not limited to, methanol, ethanol, propanol, ethyl acetate, tetrahydrofuran, dioxane, or a combination thereof,

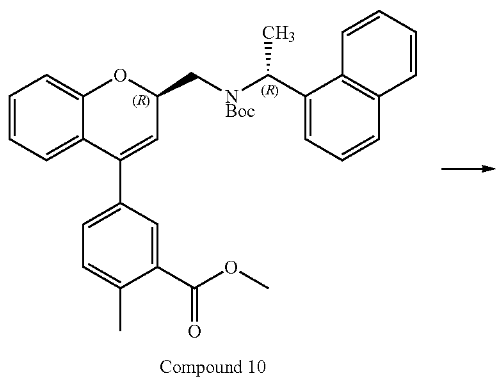

Compound 10

-continued

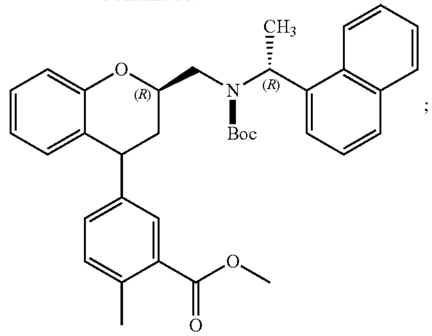

Compound 11 j) converting Compound 11 to methyl 2-methyl-5-((2R)-2-((((R)-1-(naphthalen-1-yl)ethyl)amino) methyl) chroman-4-yl)benzoate hydrochloride (Compound 12) through Boc-deprotection reaction using aqueous hydrochloric acid, trifluoroacetic acid or trimethyl silyl iodide in the presence of one or more polar solvents, wherein the one or more polar solvents includes, but not limited to, methanol, dichloromethane, ethanol, propanol, ethyl acetate, tetrahydrofuran, dioxane, or a combination thereof,

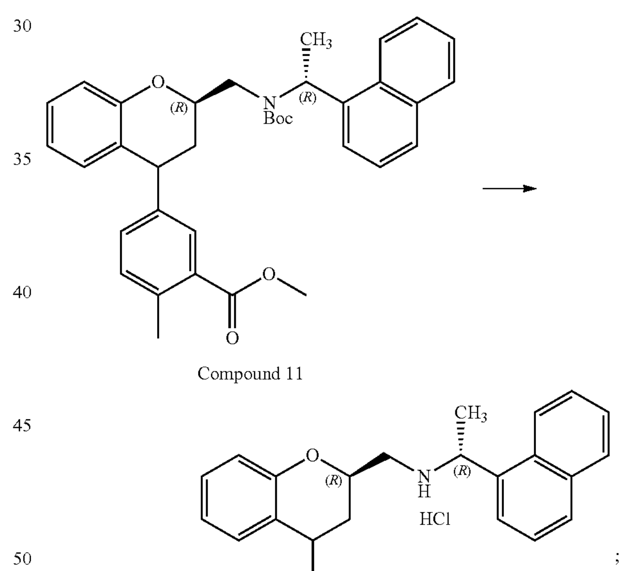

Compound 11

Compound 12 k) hydrolyzing the ester group of Compound 12 using one or more hydroxide bases (such as, but not limited to, sodium hydroxide, lithium hydroxide, potassium hydroxide, cesium hydroxide, lithium chloride, or a combination thereof) followed by aqueous reaction with the resultant carboxylate salt into the carboxylic acid, and isolation of the pure diastereoisomer by using recrystallization technique with a solvent mixture of one or more protic polar solvents and one or more aprotic polar solvents to give 2-methyl-5-((2R,4S)-2-((((R)-1-(naphthalen-1-yl)ethyl)amino)methyl) chroman-4-yl)benzoic acid (Compound-A") wherein the one or more protic polar solvents includes, but not limited to, ethanol, methanol, isopropanol, or a combination thereof, and the one or more aprotic polar solvents includes, but not limited to, dichloromethane, dimethylformamide, tetrahydrofuran, or a combination thereof,

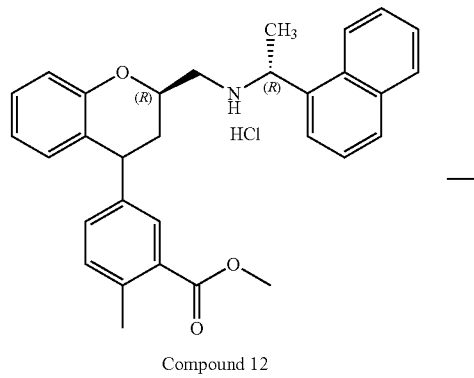

Compound 12

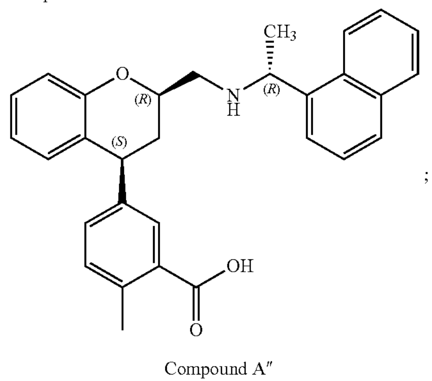

Compound A″ and l) converting Compound A" to its hydrochloride salt, 2-methyl-5-((2R,4S)-2-((((R)-1-(naphthalen-1-yl) ethyl)amino)methyl) chroman-4-yl)benzoic acid hydrochloride (Compound A) using hydrochloric acid in one or more protic polar solvents (such as, but not limited to, ethanol, methanol, isopropanol, or a combination thereof,

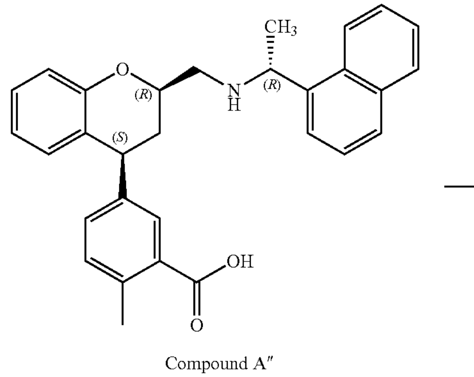

Compound A″

-continued

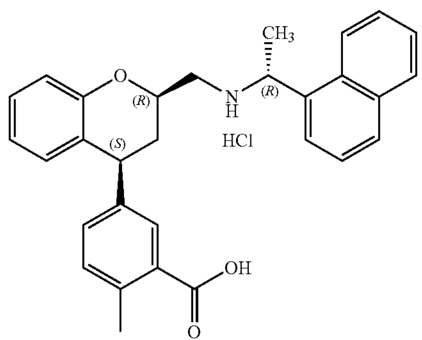

Compound A

In one aspect, the invention provides for a compound selected from (R)—N-(1-(naphthalen-1-yl)ethyl)-4-oxo-4H-chromene-2-carboxamide (Compound 3), (R)—N—((R)-1-(naphthalen-1-yl) ethyl)-4-oxochromane-2-carboxamide (Compound 4), (R)—N—((R)-1-(naphthalen-1-yl)ethyl) spiro[chromane-4,2'-[1,3]dioxolane]-2-carboxamide (Compound 5), (R)-1-(naphthalen-1-yl)-N—(((R)-spiro[chromane-4,2'-[1,3]dioxolan]-2-yl)methyl)ethan-1-amine (Compound 6), (R)-2-((((R)-1-(naphthalen-1-yl)ethyl) amino)methyl)chroman-4-one hydrochloride (Compound 7), (R)-2-((((R)-1-(naphthalen-1-yl)ethyl)amino)methyl) chroman-4-one (Compound 7"), and (R)-2-(((1-(naphthalen-1-yl)ethyl)amino)methyl)-4H-chromen-4-one (Compound 16), Compound 3

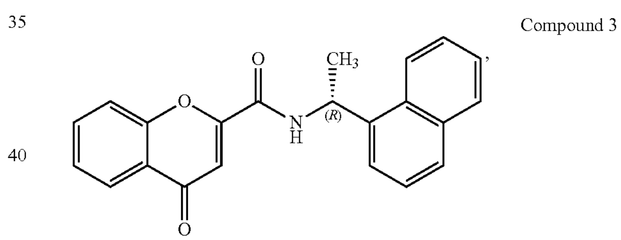

Compound 4

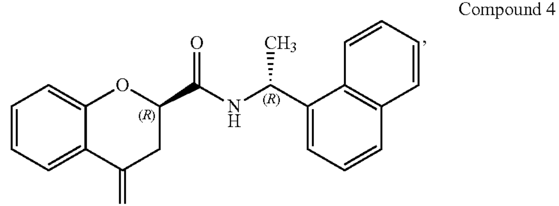

Compound 5

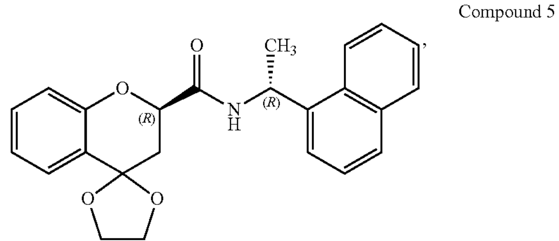

-continued

Compound 6

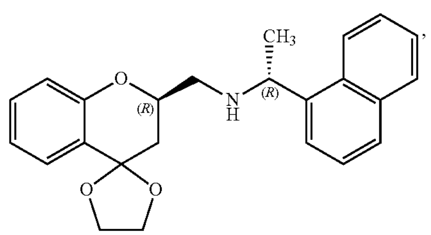

Compound 7

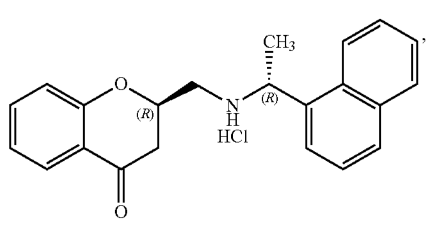

Compound 7"

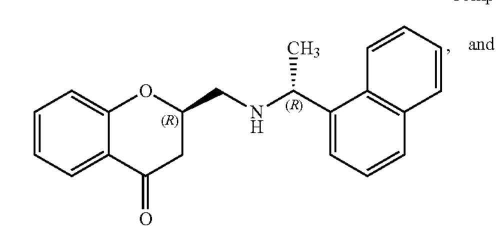

and

Compound 16

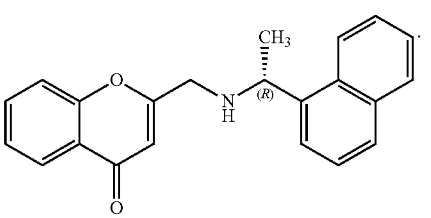

The invention is illustrated in more details by experimental methods and processes herein, but the invention should not be construed to be limited thereto.

EXAMPLES

The invention is further exemplified, but not limited by, the following examples that illustrate the preparation of Compounds 1 to 20 according to the invention.

Compounds of this invention can be made by the processes and methods depicted in the reaction schemes shown herein.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by processes and methods known to those skilled in the art following procedures set forth in references such as Fieser and Fieser's Reagents for Organic Synthesis, Volumes 1-22 (John Wiley & Sons, Inc. (2016)); Rodd's Chemistry of Carbon Compounds, Volumes 1-4 (Elsevier Science Publishers, (2008)); Organic Reactions, Volumes 1-100 (John Wiley & Sons, Inc. (1942-2019)), March's Advanced Organic Chemistry, (John Wiley & Sons, Inc., 8th Edition (2020)) and Comprehensive Organic Transformations, ed. Richard C. Larock, Ph.D. (John Wiley & Sons, Inc., 3rd Edition (2018)). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

In the reactions described hereinafter it may be necessary to protect reactive functional groups, for example, hydroxy groups, amino groups, imino groups, thio groups, carboxy groups, or a combination thereof, where these are desired in the final product, to avoid their unwanted participation in the reactions. Conventional protecting groups may be used in accordance with standard practice, for example, benzyl, p-methoxybenzyl, carboxybenzoyl (cbz), 2-mercaptoethanol, 1,2-ethanedithiol, 1,3-propanedithiol, trimethyl orthoformate, triethyl orthoformate, or any protecting group described in P. G. M. Wuts, Greene's Protective Groups in Organic Chemistry, 5th ed., John Wiley & Sons, Inc. (2014).

Synthesis of Representative Compounds of the Invention

Example 1

Step-1: (R)—N-(1-(naphthalen-1-yl)ethyl)-4-oxo-4H-chromene-2-carboxamide (Compound 3)

Compound 3

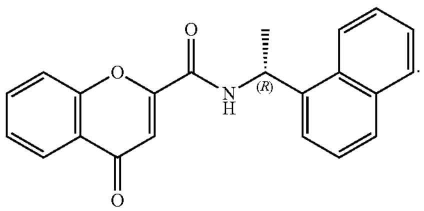

To a stirred solution of 4-oxo-4H-chromene-2-carboxylic acid (200 g, 1052 mmol), TEA (293 mL, 2104 mmol) in THF (6 v, Volume: 1200 mL) were added $T_3P$ coupling reagent (939 mL, 1578 mmol) at 5-10° C. under nitrogen atmosphere. In to this (R)-1-(naphthalen-1-yl)ethan-1-amine (198 g, 1157 mmol) was added at same temperature and the resulting mass was slowly warm to ambient temperature and stirred for 16 h. Reaction monitored by TLC and HPLC analysis. Up on completion, it was quenched with ice cold water (2 L, 10 v) and extracted with ethyl acetate (2 L, 10 v). Organic phase separated and aqueous phase back extracted with ethyl acetate (1 L, 5 v). Combined organic phase washed with water (0.4 L*2, 4 v) and brine solution (0.4 L, 2 v). It was concentrated to dryness, then crude solid was re-dissolved in ethanol (600 mL, 3 v) at 60-65° C. This was slowly cool to ambient temperature and stirred for 16 h. The mass was cooled to 0-5° C. and stirred for 30 min. The solid was filtered, washed with ice-cold ethanol (100 mL, 0.5 v) and dried in vacuum tray drier at 50-55° C. for 16 h to get off-white solid of (R)—N-(1-(naphthalen-1-yl)ethyl)-4-oxo-4H-chromene-2-carboxamide. Yield: 91% (327 g).

HPLC purity: 100%. Melting Point: 122-125° C. LC-MS: 344.34 (MH+). 1H NMR: (400 MHz, DMSO-d6) δ: 9.61 (d, J=8.0 Hz, 1H), 8.23-8.17 (m, 1H), 8.05 (dd, J=8.0, 1.6 Hz, 1H), 7.97 (dd, J=8.0, 1.6 Hz, 1H), 7.90-7.85 (m, 2H), 7.78 (dd, J=8.5, 1.0 Hz, 1H), 7.70 (dd, J=7.2, 1.1 Hz, 1H), 7.63-7.51 (m, 4H), 6.89 (s, 1H), 5.99 (p, J=7.1 Hz, 1H), 1.69 (d, J=6.9 Hz, 3H).

Step-2: (R)—N—((R)-1-(naphthalen-1-yl) ethyl)-4-oxochromane-2-carboxamide (Compound 4)

Compound 4

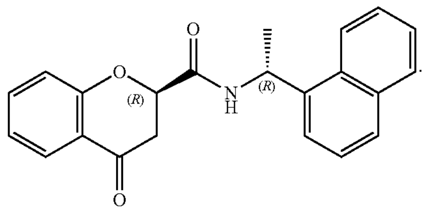

To a degassed solution of THF (750 mL, 5 v) was added Cu(OAc)2 (0.238 g, 1.310 mmol, 0.003 eq), PPh3 (0.378 g, 1.442 mmol, 0.0033 eq) and (R)-DM-SEGPHOS® ligand (1.042 g, 1.442 mmol, 0.0033 eq) at room temperature. The resulting mixture stirred at ambient temperature for 3 h. (Note: Light black grape colored solution formed). Then added Diethoxymethylsilane DEMS (280 mL, 1737 mmol, 4 eq) slowly and continued stirring for 1 h. (Note: An orange-colored solution formed at this stage). To the catalyst mixture (R)—N-(1-(naphthalen-1-yl)ethyl)-4-oxo-4H-chromene-2-carboxamide (150 g, 437 mmol, 1.0 eq) in THF (750 mL, 5.0 v) solution added at 25-30° C. and the resulting mixture stirred for 16 h. The progress of the reaction monitored by HPLC analysis. Upon completion of reaction, reaction mass slowly added to aqueous 10% sodium bicarbonate solution (25 v, 3.75 L) at 10±5° C. and the resulting mass was agitated at ambient temperature for 12 h. The product extracted in ethyl acetate (10 v, 1500 mL), and aqueous phase back extracted with additional quantity of ethyl acetate (5 v, 750 mL). The combined extractions washed with water (10 v, 1500 mL), followed half-saturated brine solution (5 v, 750 mL) and dried over anhydrous Na2SO4. It was filtered and concentrated to give white solid of crude (R)—N—((R)-1-(naphthalen-1-yl) ethyl)-4-oxochromane-2-carboxamide. The crude product was purified using ethyl acetate: n-hexanes mixture (8:1 ratio, 1200: 150 mL, 9 v). It was filtered and dried under vacuum at 40±5° C. to give pure (R)—N—((R)-1-(naphthalen-1-yl) ethyl)-4-oxochromane-2-carboxamide (140 g). Yield: 93%. Melting Point: 194-197° C. HPLC purity: 97.19% RR, other isomer SR 0.06% with 99.88% de. LC-MS: 346.34 (MH+). 1H NMR: (400 MHz, DMSO-d6) δ: 8.86 (d, J=7.9 Hz, 1H), 8.08 (dd, J=7.9, 1.6 Hz, 1H), 8.00-7.92 (m, 1H), 7.85 (d, J=8.1 Hz, 1H), 7.74 (dd, J=7.8, 1.8 Hz, 1H), 7.62-7.49 (m, 5H), 7.15 (dd, J=8.4, 1.0 Hz, 1H), 7.09 (ddd, J=8.0, 7.2, 1.1 Hz, 1H), 5.73 (p, J=7.0 Hz, 1H), 5.18 (dd, J=8.7, 5.0 Hz, 1H), 3.03-2.89 (m, 2H), 1.52 (d, J=6.9 Hz, 3H).

Step-3: (R)—N—((R)-1-(naphthalen-1-yl)ethyl) spiro[chromane-4,2'-[1,3]dioxolane]-2-carboxamide (Compound 5)

Compound 5

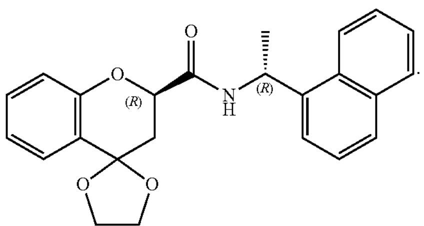

To a stirred solution of (R)—N—((R)-1-(naphthalen-1-yl)ethyl)-4-oxochromane-2-carboxamide (250 g, 724 mmol, 1 eq) in toluene (5000 mL, ~20 v) was added ethylene glycol (1009 mL, 18.1 mol, 25 eq), followed by p-toluene sulphonic acid monohydrate (13.7 g, 72.4 mmol, 0.1 eq) and resulting mixture was refluxed at 120±10° C. for 16 h. After 16 h HPLC showed starting material content 2.45%, additional quantity of PTSA (1.37 g, 72.4 mmol, 0.1 eq) and ethylene glycol (250 mL, 4.52 mol, 6.25 eq) was added and continued reaction for 5 h. Reaction progress was monitored by UPLC, upon completion, cool the mass to 25±5° C., then treated with water (80 mL, 10 v) and stirred for 30 min. Product extracted in ethylacetate (80 mL, 10 v) and aqueous phase back extracted with ethyacetate (40 mL, 5 v). Combined organic phase was dried over Na2SO4, filtered and concentrated to get (R)—N—((R)-1-(naphthalen-1-yl)ethyl) spiro[chromane-4,2'-[1,3]dioxolane]-2-carboxamide as an off-white solid. Impure compound as such used for next step. The purification procedure described herein can be used to obtain the pure compound.

Purification method: The crude product made slurry with ethyl acetate (3 v) at 65-70° C. for 30 min. It was slowly cool to ambient temperature and stirred for 16 h. Then cool the mass between 0-5° C. for 1 h, precipitated solids were collected by filtration and washed with ice-cold ethyl acetate (0.5 v). It was dried further in VTD at 50-55° C. for 16 h to get off-white solid with 71.5% yield and HPLC purity 98.65%. Yield: 93% (261 g). Melting Point: 198-202° C. LC-MS: 390.16 (MH+). 1H NMR: (400 MHz, DMSO-d6) δ 8.78 (d, J=8.0 Hz, 1H), 8.15 (d, J=8.3 Hz, 1H), 7.97 (dd, J=8.0, 1.6 Hz, 1H), 7.86 (d, J=8.0 Hz, 1H), 7.64-7.50 (m, 4H), 7.40 (dd, J=7.7, 1.7 Hz, 1H), 7.28 (ddd, J=8.7, 7.3, 1.7 Hz, 1H), 7.01-6.91 (m, 2H), 5.82 (p, J=7.1 Hz, 1H), 4.70 (dd, J=12.4, 2.4 Hz, 1H), 4.21 (qd, J=5.8, 2.3 Hz, 1H), 4.15-4.00 (m, 3H), 2.28 (dd, J=13.6, 2.5 Hz, 1H), 2.09 (dd, J=13.6, 12.5 Hz, 1H), 1.58 (d, J=6.9 Hz, 3H).

Step-4: (R)-1-(naphthalen-1-yl)-N—(((R)-spiro[chromane-4,2'-[1,3]dioxolan]-2-yl)methyl)ethan-1-amine (Compound 6)

Compound 6

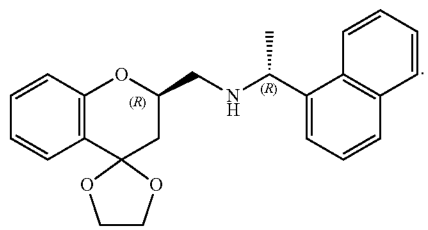

To a solution of (R)—N—((R)-1-(naphthalen-1-yl)ethyl) spiro[chromane-4,2' [1,3]dioxolane]-2-carboxamide (260 g, 668 mmol, 1.0 eq) in THF (1040 mL, 4.0 v) and toluene (2600 mL, 10 v) under nitrogen, was added a solution of vitride in toluene (562 mL, 70% w/w, 2003 mmol, 3.0 eq) over a period of 1 h at 5±5° C. It was brought to rt over 1 h and then heated to 85±5° C. for 6 h. Progress of the reaction was monitored by HPLC until the content of the intermediate (R)—N—((R)-1-(naphthalen-1-yl)ethyl)spiro[chromane-4,2' [1,3]dioxolane]-2-carboxamide is ≤1.0%. The reaction mass was cooled to 10±5° C., and excess vitride was quenched by adding ethyl acetate (520 mL, 1.0 v), followed by the addition of water (520 mL, 1 v) and the resulting mixture stirred for 15 min. Into this was added aqueous solution of NaOH (5N, 1300 mL, 5 v) and stirred for 15 min. Phases were separated, aqueous phase extracted once with ethyl acetate (2600 mL, 10 v) and the organic phases combined. It was washed with water (1300 mL, 5 v) and saturated solution of brine (1300 mL, 5 v) and concentrated under vacuum at 40±5° C. The material was re-dissolved in ethyl acetate (1300 mL, 10 v) at ambient temperature, then treated with charcoal (10%, 26 g) and Silia Met S-thiol (10%, 26 g) for 1 h. It was filtered through freshly prepared celite bed, washed with ethyl acetate (1300 mL, 5 v). Combined filtrate concentrated to dryness and re-dissolved the mass in ethanol (780 mL, 3 v) at 55±5° C., then cool to ambient temperature and continued stirring for 16 h. It was cool to 0±5° C., filtered and solid washed with ice-cold ethanol (260 mL, 1 v). The off-white solid dried in VTD at 45±50° C. for 12 h to get (R)-1-(naphthalen-1-yl)-N—(((R)-spiro[chromane-4,2'-[1,3]dioxolan]-2-yl)methyl) ethan-1-amine. Yield: 78% (196.1 g). Melting Point: 141-144° C. LC-MS: 376.2 (MH+). HPLC Purity: 97.95%. 1H NMR: (400 MHz, DMSO-d6) δ 8.30 (dd, J=7.8, 1.8 Hz, 1H), 7.96-7.90 (m, 1H), 7.80 (d, J=8.1 Hz, 1H), 7.73 (dd, J=7.2, 1.3 Hz, 1H), 7.52 (ddt, J=8.0, 6.8, 5.3 Hz, 3H), 7.36 (dd, J=7.7, 1.7 Hz, 1H), 7.22 (ddd, J=8.7, 7.2, 1.7 Hz, 1H), 6.90 (td, J=7.5, 1.2 Hz, 1H), 6.79 (dd, J=8.3, 1.1 Hz, 1H), 4.64 (dt, J=9.2, 4.4 Hz, 1H), 4.28 (dddd, J=12.0, 6.8, 5.2, 1.9 Hz, 1H), 4.21-4.15 (m, 1H), 4.10-3.97 (m, 3H), 2.80 (dt, J=12.0, 5.7 Hz, 1H), 2.65 (ddd, J=12.4, 7.8, 4.9 Hz, 1H), 2.42 (s, 1H), 2.20 (dd, J=13.6, 2.0 Hz, 1H), 1.78 (dd, J=13.7, 12.2 Hz, 1H), 1.42 (d, J=6.5 Hz, 3H).

Step-5: (R)-2-((((R)-1-(naphthalen-1-yl)ethyl) amino)methyl)chroman-4-one hydrochloride (Compound 7)

Compound 7

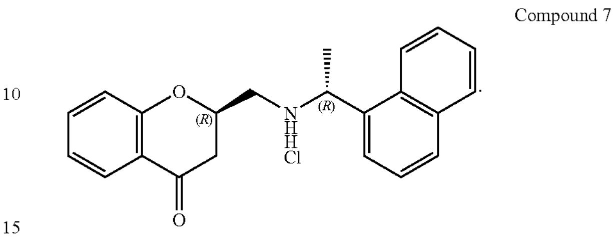

To a stirred solution of (R)-1-(naphthalen-1-yl)-N—(((R)-spiro[chromane-4,2'-[1,3]dioxolan]-2-yl)methyl)ethan-1-amine (272 g, 724 mmol, 1.0 eq) in acetone (2.6 L, ~4.8 v) was added aqueous 6N HCl solution (540 mL, ~2 v) and resulting mixture was heated between 70-80° C. for 4 h. Reaction was monitored by HPLC (Starting material absent). Up on completion, it was brought to RT over 1 h, and added water (540 mL, ~2 v), then cool the mass to 0±5° C. for 1 h. The solid thus precipitated was filtered, washed with water (1090 mL, 4 v) followed by ice-cold acetone (540 mL, 2.0 v, ~10° C.). It was dried at 45-50° C. in VTD for 16 h to get pure (R)-2-((((R)-1-(naphthalen-1-yl)ethyl)amino) methyl)chroman-4-one hydrochloride as white solid. Yield: 89% (236.1 g). Melting Point: 264-267° C. HPLC: Chemical purity: 99.92%, Chiral Purity: 100% de and ee. LC-MS: 332.40 (MH+ Free base). 1H NMR: (400 MHz, DMSO-d6) δ 10.50-10.26 (m, 1H), 10.00 (d, J=9.1 Hz, 1H), 8.33-8.28 (m, 1H), 8.14 (dd, J=7.3, 1.1 Hz, 1H), 8.05-7.98 (m, 2H), 7.76 (dd, J=7.8, 1.7 Hz, 1H), 7.69-7.59 (m, 4H), 7.14-7.07 (m, 2H), 5.50 (p, J=6.6 Hz, 1H), 5.10 (ddt, J=13.6, 8.2, 3.0 Hz, 1H), 3.43 (dd, J=13.1, 5.8 Hz, 1H), 3.29 (tt, J=8.5, 3.5 Hz, 1H), 2.93 (dd, J=17.0, 13.3 Hz, 1H), 2.77 (dd, J=17.0, 3.0 Hz, 1H), 1.77 (d, J=6.6 Hz, 3H).

Step-6: tert-butyl ((R)-1-(naphthalen-1-yl)ethyl) (((R)-4-oxochroman-2-yl)methyl) carbamate (Compound 8)

Compound 8

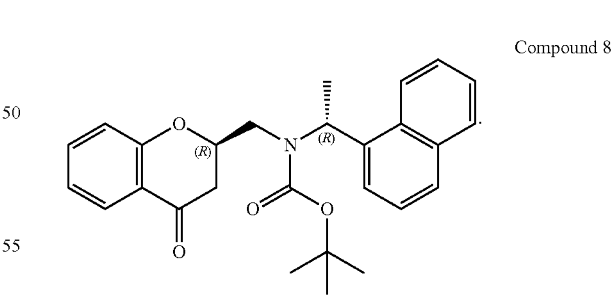

To a stirred solution of (R)-2-((((R)-1-(naphthalen-1-yl) ethyl)amino)methyl)chroman-4-one hydrochloride (235 g, 1.0 eq) in DCM (2.35 L, 10 v) was added triethylamine (267 mL, 1.92 mol, 3.0 eq) at 10-15° C., followed by di-tert-butyl dicarbonate (153.5 g, 1.92 mol, 1.1 eq) and the resulting mixture was heated between 40-45° C. for 6 h. Reaction progress was monitored by HPLC and TLC analysis. Up on completion, cool the mass to ambient temperature and diluted with water (1.15 L, 5 v). Separate the phases and aqueous phase back extracted with DCM (470 mL, 2 v). Organic phases were combined, washed with water (1.15 L, 5 v), brine solution (470 mL, 2 v), dried over Na2SO4 and filtered. The material was passed through silica bed and concentrated to get yellow oily liquid of tert-butyl ((R)-1-(naphthalen-1-yl)ethyl)(((R)-4-oxochroman-2-yl)methyl) carbamate. Yield: 92.5% (255 g). HPLC: Chiral Purity 100%. LC-MS: 454.11 (M+Na). 1H NMR: (400 MHz, DMSO-d6) δ: 8.10-8.00 (m, 1H), 7.97 (dd, J=7.9, 1.6 Hz, 1H), 7.90 (d, J=8.1 Hz, 1H), 7.69 (d, J=7.2 Hz, 1H), 7.60-7.50 (m, 4H), 7.37 (ddd, J=8.7, 7.2, 1.8 Hz, 1H), 6.92 (td, J=7.6, 1.0 Hz, 1H), 6.18 (d, J=8.3 Hz, 1H), 3.66 (tt, J=8.1, 4.9 Hz, 1H), 3.40-3.21 (m, 3H), 2.44 (d, J=14.4 Hz, 1H), 2.25 (dd, J=17.0, 3.2 Hz, 1H), 1.64 (d, J=6.8 Hz, 3H), 1.48 (d, J=12.2 Hz, 9H).

Step-7: (R)-2-(((tert-butoxycarbonyl)((R)-1-(naphthalen-1-yl)ethyl)amino)methyl)-2H-chromen-4-yl trifluoromethanesulfonate (Compound 9)

Compound 9

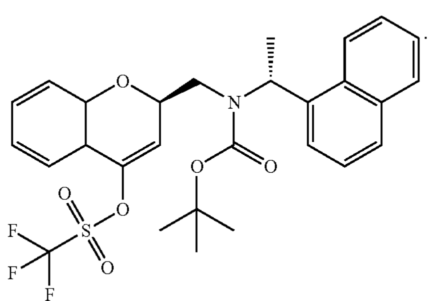

To a solution of tert-butyl ((R)-1-(naphthalen-1-yl)ethyl)(((R)-4-oxochroman-2-yl)methyl)carbamate (1.0 eq) in THF (7.0 v) was added HMPA (0.0015 v) under nitrogen. Potassium bis(trimethylsilyl)amide (KHMDS) solution (1M in THF) (1.5 eq) was added drop wise to the solution at −83±5° C. over a period of 1 h 30 min. The reaction mass was allowed to stir for 45 min at −83±5° C. A solution of N-phenyl-bis(trifluoromethanesulfonimide) (PhNTf2) (1.5 eq) in THF (4.0 v) was added drop wise at same temperature over a period of 3 h 10 min. this was stirred for further 30 min. The reaction was quenched using purified water (1.5 v) at −20±10° C. to get (R)-2-(((tert-butoxycarbonyl)((R)-1-(naphthalen-1-yl)ethyl)amino)methyl)-2H-chromen-4-yl trifluoromethanesulfonate and used as such for the next step.

In some embodiments, HMPA alternatives can be used in place of the HMPA solvent, which includes, but not limited to, DMPU, DMI, DMSO, DMF, NMP, DMA, or a combination thereof.

In some embodiments, an isolation procedure can comprise the following: Upon completion of reaction, the mass was quenched with purified water (1.5 v) at −20±10° C.

THF was concentrated and, then product extracted with n-hexanes (5 v×3 times), combined extraction washed with water (5 v), and concentrated to get (R)-2-(((tert-butoxycarbonyl)((R)-1-(naphthalen-1-yl)ethyl)amino)methyl)-2H-chromen-4-yl trifluoromethanesulfonate. Yield: 84%. Mass: 586.0 [M+Na]. 1H NMR (400 MHz, DMSO-d6) δ: 8.00 (dt, J=6.9, 3.5 Hz, 2H), 7.97-7.88 (m, 1H), 7.68 (s, 1H), 7.57 (ddd, J=8.7, 6.9, 3.0 Hz, 3H), 7.22 (t, J=7.7 Hz, 1H), 7.05 (dd, J=7.7, 1.6 Hz, 1H), 6.96 (td, J=7.6, 1.1 Hz, 1H), 6.45 (s, 1H), 6.09 (s, 1H), 5.30 (s, 1H), 3.95 (s, 1H), 1.63 (d, J=6.9 Hz, 3H), 1.39 (s, 9H), 1.24 (s, 2H).

Step-8: Methyl 5-((R)-2-(((tert-butoxycarbonyl)((R)-1-(naphthalen-1-yl) ethyl) amino) methyl)-2H-chromen-4-yl)-2-methylbenzoate (Compound 10)

Compound 10

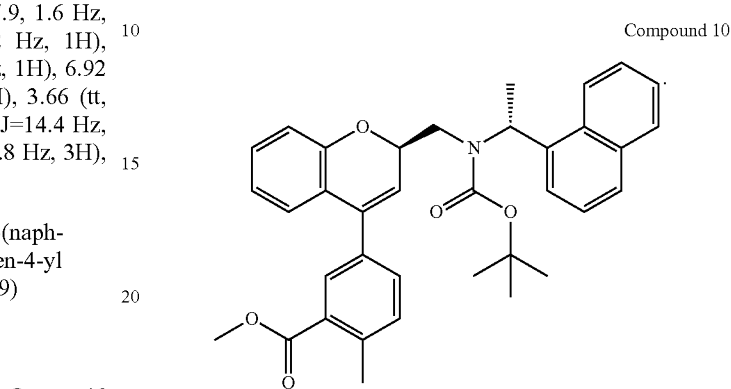

(R)-2-(((tert-butoxycarbonyl)((R)-1-(naphthalen-1-yl) ethyl)amino)methyl)-2H-chromen-4-yl trifluoromethanesulfonate in THF (1.0 eq) was added to the reactor under nitrogen. To the solution were added methyl 2-methyl-5-(4,4,5,5-tetramethyl-1,3,2-dioxaborolan-2-yl)benzoate (0.95 eq) and K3PO4 (1.5 eq). Pd(PPh3)4 (1.2 mol %) was added to the solution under nitrogen at ambient temperature. The reaction mixture was heated to reflux temperature for 12-18 h. The reaction mass cooled to ambient temperature and into that was added celite (1 w/w), n-heptane (3.0 v) and water (1.0 v). The reaction mass was filtered, layer separated and the aqueous phase was further extracted with MTBE (2.0 v).

To the combined organic phase were added activated Carbon (0.2 w/w), silica gel (1.0 w/w) and celite (1.0 w/w). The mixture was stirred for 3 h at ambient temperature. The mixture was then filtered and the resulting material evaporated under vacuum to ~2 v. Isopropyl alcohol (2.0 v) was added to the reaction mass and evaporated to ~2.0 v. This co-distillation process was repeated once again. The material was cooled to 5±5° C. and stirred for 4-8 h at the same temperature and filtered to give methyl5-((R)-2-(((tert-butoxycarbonyl)((R)-1-(naphthalen-1-yl)ethyl)amino) methyl)-2H-chromen-4-yl)-2-methylbenzoate as a wet cake.

The wet cake was stirred in isopropyl alcohol (2.0 v) and heated to 68±5° C. to give a clear solution. This was then cooled to 15±5° C. and stirred for 16 h at the same temperature. Solid precipitate was filtered and the solids washed with isopropyl alcohol (0.5 v). The solid was dried under vacuum at 40±5° C. until LOD ≤0.5%.

The solid was added to the reactor containing ethyl acetate (3.15 v). The resulting solution was filtered through micro porous filter. The ethyl acetate layer was washed with purified water (1.5 w/w) for a period of 10 min. The organic phase was separated and washed again with purified water (1.5 w/w). The organic layer was separated and evaporated under vacuum to ~1.5-2 v at 40±5° C. The residue was co-distilled with isopropyl alcohol (or ethanol) (1.57 v) twice to ~1.5-2 v. Purified water (3.0 w/w) was added to the solution. Isopropyl alcohol was removed by evaporation under vacuum to ~3.5-4 v at 40±5° C. Solid precipitated was filtered and washed with water (0.5 v). The solid thus obtained was dried under vacuum oven at 45±5° C. until LOD ≤0.5% to give methyl-5-((R)-2-(((tert-butoxycarbonyl)((R)-1-(naphthalen-1-yl)ethyl)amino)methyl)-2H-chromen-4-yl)-2-methylbenzoate. Yield: 56.81%. Mass: 586.44 (M+Na). 1H NMR (400 MHz, DMSO-d6) δ: 8.08 (d, J=8.0 Hz, 1H), 7.97 (dd, J=8.1, 1.4 Hz, 1H), 7.91 (d, J=8.2 Hz, 1H), 7.68 (d, J=7.2 Hz, 1H), 7.65-7.49 (m, 4H), 7.35 (d, J=7.9 Hz, 1H), 7.21 (s, 1H), 7.10-7.02 (m, 1H), 6.81-6.69 (m, 2H), 6.38 (bs, 1H), 6.11 (bs, 1H), 5.19 (bs, 1H), 3.85 (s, 3H), 3.75 (bs, 1H), 3.31 (m, 1H), 2.53 (s, 3H), 1.65 (d, J=6.8 Hz, 3H), 1.50 (bs, 1H), 1.32 (bs, 9H).

In some embodiments, an alternate procedure can comprise as follows: To the solution of (R)-2-(((tert-butoxycarbonyl)((R)-1-(naphthalen-1-yl)ethyl)amino)methyl)-2H-chromen-4-yl trifluoromethanesulfonate (110 g, 195 mmol) in a mixture of THF (volume: 500 ml, ratio: 2.000) and water (volume: 250 ml, ratio: 1.000) was added methyl 2-methyl-5-(4,4,5,5-tetramethyl-1,3,2-dioxaborolan-2-yl) benzoate (51.2 g, 185 mmol), potassium phosphate tribasic (91 g, 429 mmol) and Tetrakis (1.128 g, 0.976 mmol) sequentially under nitrogen. The mixture was heated to reflux for 18 h. Progress of the reaction was monitored by HPLC. After complete consumption of the starting materials, the mass was filtered through celite pad and concentrated under reduced pressure. The residue was diluted with water and product extracted with n-hexanes (5 v×3 time), combined extraction washed with water (5 v) and concentrated under reduced pressure. The residue was co-distilled with ethanol (2 v), then fresh ethanol (4 v) was added and the resulting mixture was warmed to get clear solution. It was cool to room temperature and stirred for 18 h. The mass was cool to 0±5° C. with stirring for 1 h, product thus crystallized was filtered, and solid washed with ice-cold ethanol (1 v). The solid thus obtained was dried under vacuum oven at 45±5° C. until LOD ≤0.5% to give methyl5-((R)-2-(((tert-butoxycarbonyl)((R)-1-(naphthalen-1-yl) ethyl)amino)methyl)-2H-chromen-4-yl)-2-methylbenzoate. Yield: 82%. Mass: 586.44 (M+Na). 1H NMR (400 MHz, DMSO-d6) δ: 8.08 (d, J=8.0 Hz, 1H), 7.97 (dd, J=8.1, 1.4 Hz, 1H), 7.91 (d, J=8.2 Hz, 1H), 7.68 (d, J=7.2 Hz, 1H), 7.65-7.49 (m, 4H), 7.35 (d, J=7.9 Hz, 1H), 7.21 (s, 1H), 7.10-7.02 (m, 1H), 6.81-6.69 (m, 2H), 6.38 (bs, 1H), 6.11 (bs, 1H), 5.19 (bs, 1H), 3.85 (s, 3H), 3.75 (bs, 1H), 3.31 (m, 1H), 2.53 (s, 3H), 1.65 (d, J=6.8 Hz, 3H), 1.50 (bs, 1H), 1.32 (bs, 9H).

Step-9: Methyl 5-((2R)-2-(((tert-butoxycarbonyl) ((R)-1-(naphthalen-1-yl)ethyl)amino) methyl) chroman-4-yl)-2-methylbenzoate (Compound 11)

Compound 11

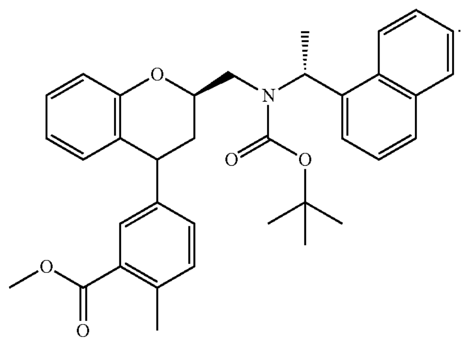

Ammonium formate (10.0 eq) was dissolved in methanol and, heated to 33-34° C. (6.0 v) giving a clear solution. Methyl-5-((R)-2-(((tert-butoxycarbonyl)((R)-1-(naphthalen-1-yl)ethyl)amino)methyl)-2H-chromen-4-yl)-2-methylbenzoate (1.0 eq) was dissolved in ethyl acetate (3.0 v) and heated to 33-34° C., and 5% Pd/C 50% wet (10% w/w g) was added. Ammonium formate solution was then added with an addition funnel over a period of 6 h to the suspension. The reaction mixture was heated at 33-34° C. for 2 h 30 min. The reaction mixture was cooled to 20° C. over a period of 4 h, and was allowed to stir for 9 hours at 20° C. Catalyst was filtered off through a GF/F glass microfiber filter and washed with methanol (1.0 v), then with ethyl acetate (2.0 v). The solution was successively concentrated at 250 mbar and diluted with ethyl acetate, in order to reach a 25/75 methanol/ethyl acetate molar ratio (NMR). To the white suspension thus obtained was added ethyl acetate (4.0 v) followed by water (8.0 v), allowing for facile separation of the two homogeneous layers. The organic layer was washed with the water (8.0 v), then successively concentrated at 250 mbar and diluted with methanol in order to remove ethyl acetate (NMR). Intermediate methyl 5-((2R)-2-(((tert-butoxycarbonyl)((R)-1-(naphthalen-1-yl)ethyl) amino) methyl) chroman-4-yl)-2-methylbenzoate was isolated as a methanol solution (~3.0 v) which was ready for use in the next step of the synthesis. Yield: 100%. Mass: 588.25 [M+Na]. 1H NMR (400 MHz, DMSO-d6) δ: 8.05 (dd, J=8.1, 1.5 Hz, 2H), 7.94 (d, J=8.2 Hz, 1H), 7.72 (d, J=7.1 Hz, 1H), 7.69-7.48 (m, 3H), 7.34 (d, J=2.0 Hz, 1H), 7.24 (d, J=7.9 Hz, 1H), 6.98 (dd, J=7.8, 2.0 Hz, 1H), 6.92 (t, J=7.3 Hz, 1H), 6.59 (td, J=7.5, 1.3 Hz, 1H), 6.33 (s, 1H), 6.27 (d, J=7.7 Hz, 1H), 6.14 (s, 1H), 3.83 (s, 3H), 3.21 (dd, J=14.4, 5.9 Hz, 2H), 2.48 (s, 3H), 1.66 (s, 3H), 1.48 (bs, 2H), 1.37 (bs, 9H), 1.24 (s, 2H).

In some embodiments, an alternate procedure can comprise as follows: in a hydrogenation reactor, methyl-5-((R)-2-(((tert-butoxycarbonyl)((R)-1-(naphthalen-1-yl)ethyl) amino)methyl)-2H-chromen-4-yl)-2-methylbenzoate (1.0 eq) was dissolved in ethyl acetate (4 v), followed by addition of methanol (7 v), ammonia 7N in methanol solution (2 v) and the resulting mixture stirred for 15-30 min. Then 5% Pd/C 50% wet (10% w/w) added and hydrogen gas supplied to reaction mass (pressure not more than 2.0 Kg/cm$^2$). The reaction mixture temperature maintained between 28-34° C. for 5-7 h. Upon completion of reaction by HPLC monitoring, catalyst was filtered off through a GF/F glass microfiber filter and washed with methanol (1.0 v), then with ethyl acetate (2.0 v). The solution was successively concentrated under reduced pressure and swapped with ethyl acetate (5 v). The concentrated mass obtained was dissolved in ethyl acetate (5 v). Intermediate methyl 5-((2R)-2-(((tert-butoxycarbonyl)((R)-1-(naphthalen-1-yl)ethyl)amino) methyl) chroman-4-yl)-2-methylbenzoate was isolated as a ethyl acetate solution (5 v) which was ready for use in the next step of the synthesis. Yield: 100%. Mass: 588.25 [M+Na]. 1H NMR (400 MHz, DMSO-d6) δ: 1H NMR (400 MHz, DMSO-d6) δ: 8.05 (dd, J=8.1, 1.5 Hz, 2H), 7.94 (d, J=8.2 Hz, 1H), 7.72 (d, J=7.1 Hz, 1H), 7.69-7.48 (m, 3H), 7.34 (d, J=2.0 Hz, 1H), 7.24 (d, J=7.9 Hz, 1H), 6.98 (dd, J=7.8, 2.0 Hz, 1H), 6.92 (t, J=7.3 Hz, 1H), 6.59 (td, J=7.5, 1.3 Hz, 1H), 6.33 (s, 1H), 6.27 (d, J=7.7 Hz, 1H), 6.14 (s, 1H), 3.83 (s, 3H), 3.21 (dd, J=14.4, 5.9 Hz, 2H), 2.48 (s, 3H), 1.66 (s, 3H), 1.48 (bs, 2H), 1.37 (bs, 9H), 1.24 (s, 2H).

Step-10: methyl 2-methyl-5-((2R)-2-((((R)-1-(naphthalen-1-yl)ethyl)amino) methyl) chroman-4-yl) benzoate hydrochloride (Compound 12)

Compound 12

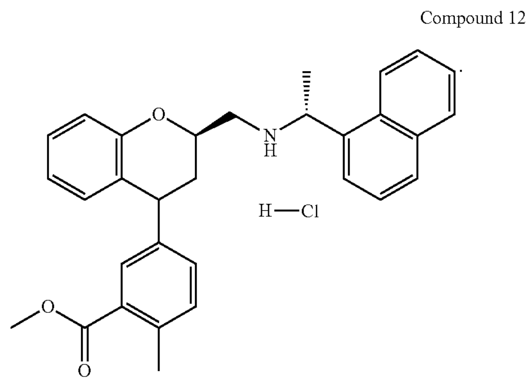

Methyl 5-((2R)-2-(((tert-butoxycarbonyl)((R)-1-(naphthalen-1-yl)ethyl)amino) methyl) chroman-4-yl)-2-methylbenzoate (300 g, 530 mmol, 1.0 eq) in methanol (1.2 L, 4.0 v) solution was heated to reflux (63° C.). Aqueous 6 N HCl (~352 mL, 2121 mmol, 4.0 eq) was added with a dropping funnel to the reaction mixture at 63° C. over a period of 2 h. The solution was allowed to stir at 63° C. for an additional one hour and cooled to 20° C. at −10° C./h rate and then allowed to stir at 20° C. for 7 h. The white suspension was filtered and the solid was washed first with methanol (225 mL, 0.75 v), then with water [2×300 mL (1 v)], affording methyl 2-methyl-5-((2R)-2-((((R)-1-(naphthalen-1-yl)ethyl) amino) methyl) chroman-4-yl)benzoate hydrochloride as a wet white hydrochloride salt. This product was ready for use in the next step of the synthesis. Yield: 98%. Mass: 466.12. 1H NMR (400 MHz, DMSO-d6) δ 8.33-8.26 (m, 1H), 7.96-7.90 (m, 1H), 7.79 (d, J=8.1 Hz, 1H), 7.72 (dd, J=7.2, 1.2 Hz, 1H), 7.63 (d, J=1.3 Hz, 1H), 7.56-7.47 (m, 3H), 7.29 (d, J=1.2 Hz, 2H), 7.07 (td, J=7.4, 1.4 Hz, 1H), 6.79 (dd, J=8.2, 1.2 Hz, 1H), 6.72 (td, J=7.5, 1.3 Hz, 1H), 6.53 (dt, J=7.7, 1.3 Hz, 1H), 4.68 (d, J=6.9 Hz, 1H), 4.27 (dt, J=15.3, 6.1 Hz, 2H), 3.79 (s, 3H), 2.78 (s, 1H), 2.70-2.59 (m, 1H), 2.49 (s, 3H), 2.42 (s, 1H), 2.25 (ddd, J=13.4, 5.8, 1.7 Hz, 1H), 1.77 (q, J=12.0 Hz, 1H), 1.42 (d, J=6.5 Hz, 3H).

In some embodiments, an alternate procedure can comprise as follows: methyl 5-((2R)-2-(((tert-butoxycarbonyl) ((R)-1-(naphthalen-1-yl)ethyl)amino) methyl) chroman-4-yl)-2-methylbenzoate (10 g, 17.66 mmol, 1.0 eq) in ethylacetate (60 mL, 6 v) solution was heated to reflux (63° C.). Con. HCl (6 mL, 4.0 eq, 0.6 v) was added with a dropping funnel to the reaction mixture at 63° C. and continued over a period of 2 h. Reaction progress was monitored by HPLC. The reaction mixture was allowed to cool to 25-30° C. It was neutralized with saturated aqueous sodium bicarbonate solution at 25-30° C. (pH adjusted to 7). The organic phase separated and washed with water (5 v) and concentrated to dryness. It was re-dissolved in methanol (20 v) at 60-65° C. for 30 min and allowed to stir at 25-3° C. for 16 h. Chiral pure product crystallized was collected by filtration and solid washed with ice-cold methanol (1 v). It was dried in vacuum, affording methyl 2-methyl-5-((2R)-2-((((R)-1-(naphthalen-1-yl)ethyl)amino) methyl) chroman-4-yl)benzoate hydrochloride as a wet white solid. Chiral Purity: 99.80% (RRS). Yield: 70.5% (5.8 g). Mass: 466.12. 1H NMR (400 MHz, DMSO-d6) δ 8.33-8.26 (m, 1H), 7.96-7.90 (m, 1H), 7.79 (d, J=8.1 Hz, 1H), 7.72 (dd, J=7.2, 1.2 Hz, 1H), 7.63 (d, J=1.3 Hz, 1H), 7.56-7.47 (m, 3H), 7.29 (d, J=1.2 Hz, 2H), 7.07 (td, J=7.4, 1.4 Hz, 1H), 6.79 (dd, J=8.2, 1.2 Hz, 1H), 6.72 (td, J=7.5, 1.3 Hz, 1H), 6.53 (dt, J=7.7, 1.3 Hz, 1H), 4.68 (d, J=6.9 Hz, 1H), 4.27 (dt, J=15.3, 6.1 Hz, 2H), 3.79 (s, 3H), 2.78 (s, 1H), 2.70-2.59 (m, 1H), 2.49 (s, 3H), 2.42 (s, 1H), 2.25 (ddd, J=13.4, 5.8, 1.7 Hz, 1H), 1.77 (q, J=12.0 Hz, 1H), 1.42 (d, J=6.5 Hz, 3H).

Step-11: 2-methyl-5-((2R,4S)-2-((((R)-1-(naphthalen-1-yl)ethyl)amino)methyl) chroman-4-yl)benzoic acid hydrochloride Salt (Compound A" and Compound A)

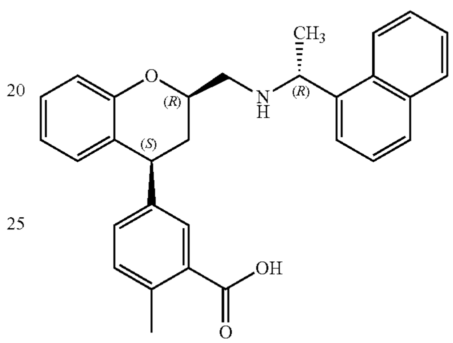

Compound A″

Compound A

Methyl-2-methyl-5-((2R,4S)-2-((((R)-1-(naphthalen-1-yl)ethyl)amino) methyl) chroman-4-yl)benzoate hydrochloride (260 g, 518 mmol, 1.0 eq) was dissolved in a mixture of methanol (1.48 L, 5.7 v) and tetrahydrofuran (1.48 L, 5.7 v). The solution was heated to 55° C., into that was added 10 N NaOH (~260 mL, 2589 mmol, 5.0 eq) over a period of 20 min. The clear solution was allowed to stir at 55° C. for 2 h (pH 10). The reaction mixture was cooled to 30° C. and diluted with water (1.82 L, 7.0 v). Aqueous HCl 2N (1062 mL, 2124 mmol, 4.1 eq.) was slowly added to adjust the pH to 6-7. The zwitterion was precipitated and the suspension was cooled to 20° C. and allowed to stir at this temperature for 30 min. The sandy solid was easily filtered, washed first with water [2×1300 mL (5 v)] and then with EtOH (520 mL, 2.0 v) followed by isopropyl alcohol (IPA) (260 mL, 1.0 v). The white solid was dried at 40° C. in vacuo for 20 h to afford 2-methyl-5-((2R,4S)-2-((((R)-1-(naphthalen-1-yl) ethyl)amino)methyl) chroman-4-yl)benzoic acid (Compound A") (crude, 225 g). Yield: 96.15%. Purity: 83.79: 15.57%

Purification: the crude 2-methyl-5-((2R,4S)-2-((((R)-1-(naphthalen-1-yl)ethyl)amino)methyl) chroman-4-yl)benzoic acid (225 g, 498 mmol, 1.0 eq) was suspended in a 5:1 ethanol/dichloromethane solvent mixture (5.4 L, 24.0 v). The suspension was heated to vigorous refluxing (60° C.) to complete dissolution of the material. The subsequent crystallization began before the end of the dissolution. The suspension was allowed to stir at 60° C. for 10 min and then was cooled to 20° C. at a −20° C./h rate, filtered, washed first with 5:1 ethanol/dichloromethane solvent mixture (2×675 mL, 3 v), then with ethanol (225 mL, 1 v). The white solid was dried at 40° C. in vacuo overnight to afford 2-methyl-5-((2R,4S)-2-((((R)-1-(naphthalen-1-yl)ethyl)amino) methyl) chroman-4-yl)benzoic acid (Compound A") as a white solid. Yield: 64.1% (150 g). Purity: 99.70:0.20%

Hydrochloride Salt Preparation: The diastereomerically pure 2-methyl-5-((2R,4S)-2-((((R)-1-(naphthalen-1-yl) ethyl)amino)methyl) chroman-4-yl)benzoic acid (150 g, 332 mmol, 1.0 eq) thus obtained was suspended in water (2.55 L, 17 v). After heating the reaction mass to 30° C., a solution of 2 N aqueous NaOH (~300 mL, 598 mmol, 1.8 eq) was added quickly, leading to complete dissolution of the compound. The solution was filtered through a GF/A glass microfiber filter in order to remove any solid impurity. Afterwards, 2 N aqueous HCl was added (665 mL, 1329 mmol, 4 eq) at the same temperature, inducing precipitation of a voluminous white solid difficult to stir. The reaction mass was allowed to stir at ambient temperature (22° C.) for 20 h. The resulting slurry was filtered, washed with water until the pH of the filtrate became 6 [1500 mL(10 v) then 3×600 mL(4 v)]. After 65 h at 40° C. in a drying oven, 2-methyl-5-((2R,4S)-2-((((R)-1-(naphthalen-1-yl)ethyl) amino)methyl) chroman-4-yl)benzoic acid Hydrochloride salt was obtained as a white solid in a quantitative yield. Yield: 89.53%. Purity: 99.63%. Mass: 452.18[MH+]. 1H NMR (DMSO-d6) δ: 12.76 (bs, 1H), 10.07 (bs, 1H), 9.64 (bs, 1H), 8.30 (d, J=8.4 Hz, 1H), 8.14-7.93 (m, 3H), 7.73-7.56 (m, 4H), 7.33-7.20 (m, 2H), 7.14 (t, J=7.6 Hz, 1H), 6.87 (dd, J=8.2, 1.0 Hz, 1H), 6.79 (td, J=7.6, 1.1 Hz, 1H), 6.57 (d, J=7.7 Hz, 1H), 5.48 (bs, 1H), 4.68 (m, 1H), 4.29 (dd, J=12.0, 5.7 Hz, 1H), 3.30 (d, J=8.6 Hz, 1H), 3.20 (d, J=12.8 Hz, 1H), 2.48 (s, 3H), 2.24 (dd, J=12.7, 5.3 Hz, 1H), 1.92 (q, J=12.1 Hz, 1H), 1.77 (d, J=6.6 Hz, 3H). IR (KBr, cm-1): 3057.55, 2956.04, 2876.08, 2767.21, 2681.29, 2499.80, 2481.85, 2298.48, 2202.11, 1711.42, 1595.25, 1579.33, 1517.30, 1497.94, 1483.60, 1451.74, 1400.13, 1379.30, 1362.67, 1300.55, 1279.31, 1238.73, 1217.88, 1187.99, 1175.75, 1118.41, 1089.60, 1072.72, 1020.79, 972.36, 928.79, 913.23, 892.94, 860.86, 797.19, 780.99, 745.77, 704.12, 667.76, 611.33, 571.04, 543.00, 528.59, 470.53, 435.58, 416.04, 401.77.

Example 2

Step-1: 2-(hydroxymethyl)-4H-chromen-4-one (Compound 14)

Compound 14

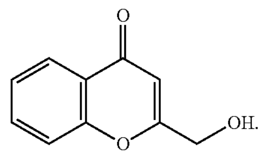

To a stirred solution of methyl 4-oxo-4H-chromene-2-carboxylate (0.5 g, 2.449 mmol) in methanol (10 v) was added slowly sodium borohydride (1.1 eq, 2.69 mmol, 0.102 g) between −20 to −25° C. under nitrogen atmosphere for 30 min. Upon completion, reaction mass diluted with water (10 v) and product extracted with ethyl acetate (10 v), washed with water (5 v) followed sat. brine solution (5 v). Organic phase dried over anhydrous sodium sulfate and evaporated to dryness gave crude compound. It was purified by column chromatography gave pure 2-(hydroxymethyl)-4H-chromen-4-one (0.26 g, 60.3%). GC-MS: 176.13 (M+). $^{1}$H NMR (400 MHz, DMSO-d6) δ 8.04 (dd, J=7.9, 1.7 Hz, 1H), 7.80 (ddd, J=8.7, 7.1, 1.7 Hz, 1H), 7.62 (dd, J=8.4, 1.0 Hz, 1H), 7.49 (ddd, J=8.1, 7.1, 1.1 Hz, 1H), 6.35 (s, 1H), 5.82 (t, J=6.1 Hz, 1H), 4.45 (dd, J=6.1, 1.0 Hz, 2H).

Step-2: 2-(chloromethyl)-4H-chromen-4-one (Compound 15)

Compound 15

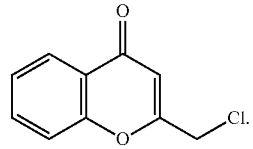

To a stirred solution of 2-(hydroxymethyl)-4H-chromen-4-one (0.5 g, 2.84 mmol) in anhydrous dichloromethane (10 v) at room temperature, 0.31 mL of thionyl chloride (4.26 mmol) was added to the solution, and reaction mixture was stirred at room temperature for 18 h. Upon completion of reaction, it was concentrated and swapped with dichloromethane (5 v). The concentrated mass was dissolved in anhydrous n-heptane, which was also evaporated again to give 2-(chloromethyl)-4H-chromen-4-one (0.5 g, 91%) which was further reacted without purification. GC-MS: 194.08, 196.08 (M+). 1H NMR (400 MHz, Chloroform-d) δ 8.26-8.17 (m, 1H), 7.72 (ddd, J=8.8, 7.2, 1.7 Hz, 1H), 7.51 (dd, J=8.5, 1.1 Hz, 1H), 7.44 (ddd, J=8.1, 7.1, 1.1 Hz, 1H), 6.46 (s, 1H), 4.45 (s, 2H).

Step-3: (R)-2-(((1-(naphthalen-1-yl)ethyl)amino) methyl)-4H-chromen-4-one (Compound 16)

Compound 16

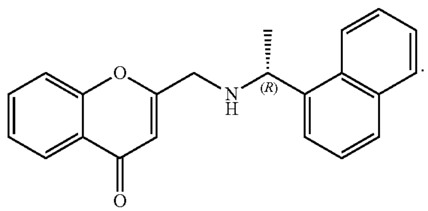

To a solution of (R)-1-(naphthalen-2-yl)ethan-1-amine (0.458 g, 2.67 mmol), potassium carbonate (0.852 g, 6.17 mmol), potassium iodide (0.341 g, 2.055 mmol) in anhydrous acetonitrile (4 mL, 10 v) was added 2-(chloromethyl)-4H-chromen-4-one (0.4 g, 2.055 mmol). The resulting mixture was stirred and refluxed for 12 h. Then it was cooled to room temperature and concentrated under vacuum. The residue was partitioned between EtOAc (10 v) and water (10 v). The organic phase was separated and the aqueous phase back extracted once with EtOAc (10 v). The organic phases were combined, washed with water, dried over anhydrous Na2SO4, filtered, and concentrated under vacuum. The residue was purified column chromatography to yield the (R)-2-(((1-(naphthalen-1-yl)ethyl)amino)methyl)-4H-chromen-4-one (0.5 g, 73.9%). LC-MS: 330.40 (MH+). 1H NMR (400 MHz, DMSO-d6) δ 8.28-8.19 (m, 1H), 8.00 (dd, J=7.9, 1.7 Hz, 1H), 7.97-7.88 (m, 1H), 7.83-7.71 (m, 3H), 7.55-7.41 (m, 5H), 6.39 (s, 1H), 4.69 (t, J=5.7 Hz, 1H), 3.68 (dd, J=16.4, 5.8 Hz, 1H), 3.57 (dd, J=16.4, 5.8 Hz, 1H), 3.15 (d, J=6.6 Hz, 1H), 1.44 (d, J=6.6 Hz, 3H).

Step-4: (R)-2-((((R)-1-(naphthalen-1-yl)ethyl) amino)methyl)chroman-4-one (Compound 7")

Compound 7″

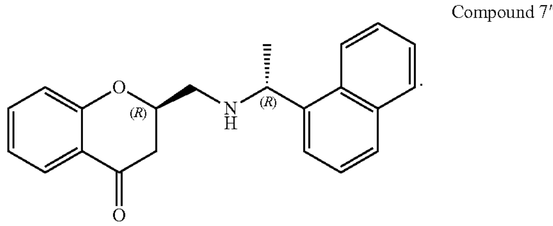

To a degassed solution of THF (2 mL, 5 v) was added Cu(OAc)2 (11 mg, 0.061 mmol, 0.03 eq) and (R)-DM-SEGPHOS® ligand (31 mg, 0.043 mmol, 0.035 eq) at room temperature. The resulting mixture stirred at ambient temperature for 3 h. (Note: Light black grape colored solution formed). Then added diethoxymethylsilane (DEMS) (0.785 mL, 4.90 mmol, 4 eq) slowly and continued stirring for 1 h. (Note: An orange colored solution formed at this stage). To the catalyst mixture (R)-2-(((1-(naphthalen-1-yl)ethyl) amino)methyl)-4H-chromen-4-one (0.4 g, 1.214 mmol, 1.0 eq) in THF (2 mL, 5 v) solution added at 25-30° C. and the resulting mixture stirred for 16 h. Upon completion of reaction, reaction mass slowly added to aqueous 10% sodium bicarbonate solution (25 v, 10 mL) at 10±5° C. and the resulting mass was agitated at ambient temperature for 12 h. The product extracted in ethyl acetate (60 v, 24 mL), and aqueous phase back extracted with additional quantity of ethyl acetate (10 v, 4 mL). The combined extractions washed with water (10 v, 4 mL), followed half-saturated brine solution (5 v, 2 mL) and dried over anhydrous Na2SO4. It was filtered and concentrated to give white solid of crude (R)-2-((((R)-1-(naphthalen-1-yl)ethyl)amino) methyl)chroman-4-one The crude product was purified using column chromatography to give pure (R)-2-((((R)-1-(naphthalen-1-yl)ethyl)amino)methyl)chroman-4-one (0.29 g, 71.4%). LC-MS: 332.3 (MH+). 1H NMR (400 MHz, DMSO-d6) δ 8.32-8.25 (m, 1H), 7.93 (dd, J=7.8, 1.8 Hz, 1H), 7.80 (d, J=8.1 Hz, 1H), 7.72 (ddd, J=7.2, 3.8, 1.4 Hz, 2H), 7.53 (ddddd, J=11.8, 10.5, 8.2, 4.7, 1.6 Hz, 4H), 7.09-6.99 (m, 2H), 5.77 (s, 1H), 4.72-4.56 (m, 2H), 2.90-2.66 (m, 4H), 1.41 (d, J=6.5 Hz, 3H).

Example 3

Step-1: (R)-4-oxochromane-2-carboxylic acid (Compound 18)

Compound 18

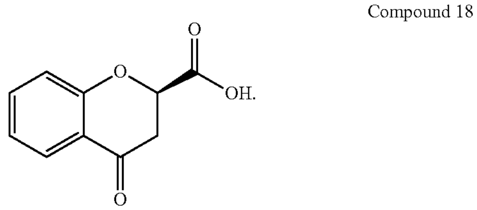 [SMILES: O=C1C[C@H](C(=O)O)Oc2ccccc21]

To a stirred solution of (R)-chromane-2-carboxylic acid (2.0 g, 11.22 mmol, 1.0 eq) in acetone (50 mL, 100 v) and purified water (20 mL, 20 v) was warmed to 42±5° C. Into this was added MgSO4 (4.05 g, 33.7 mmol) followed by KMnO4 (10.64 g, 67.3 mmol) in aliquots over a period of ~3 h. It was stirred for at least 18 h at ambient temperature. Upon completion, reaction mass cooled to 15±5° C. and stirred with saturated aqueous Na2SO3 solution (0.84 w/w) for 30 min. The product extracted with ethyl acetate (10 v×2 time), filtered through freshly prepared celite bed and concentrated under vacuum to get off-white solid of (R)-4-oxochromane-2-carboxylic acid (1.6 g, 74.2%). GC-MS: 192.13 (M+). 1H NMR (400 MHz, DMSO-d6) δ 13.36 (s, 1H), 7.74 (dd, J=7.8, 1.8 Hz, 1H), 7.60 (ddd, J=8.7, 7.2, 1.8 Hz, 1H), 7.15-7.05 (m, 2H), 5.33 (dd, J=7.5, 5.3 Hz, 1H), 3.11 (dd, J=17.0, 5.3 Hz, 1H), 2.98 (dd, J=17.0, 7.5 Hz, 1H).

Step-2: (R)—N—((R)-1-(naphthalen-1-yl)ethyl)-4-oxochromane-2-carboxamide (Compound 4)

Compound 4

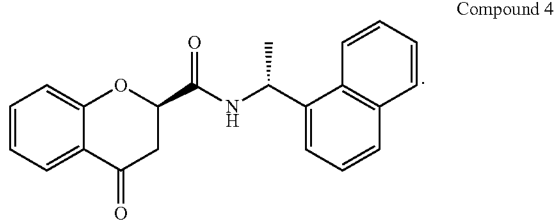 [SMILES: C[C@@H](NC(=O)[C@H]1CC(=O)c2ccccc2O1)c1cccc2ccccc12]

To a stirred solution of (R)-4-oxochromane-2-carboxylic acid (1 g, 5.025 mmol), TEA (1.09 mL, 7.807 mmol) in THF (6 v, 6 mL) were added T3P coupling reagent (3.72 mL, 6.246 mmol) at 5-10° C. under nitrogen atmosphere. In to this (R)-1-(naphthalen-1-yl)ethan-1-amine (0.891 g, 5.025 mmol) was added at same temperature and the resulting mass was slowly warm to ambient temperature and stirred for 16 h. Upon completion, it was diluted with ice-cold water (10 mL, 10 v) and product extracted with ethyl acetate (20 mL, 20 v). Organic phase separated and aqueous phase back extracted once with ethyl acetate (10 mL, 10 v). Combined organic phase washed with water (8 mL*2, 16 v) and brine solution (8 mL, 8 v). It was concentrated to dryness, then crude solid was re-dissolved in ethanol (3 mL, 3 v) at 60-65° C. This was slowly cool to ambient temperature and stirred for 2 h. The material was allowed cool to 0-5° C. and then stirred for 30 min. The solid product was filtered, washed with ice-cold ethanol (1 mL, 1 v) and dried in vacuum tray drier between 50-55° C. for 3 h to get off-white solid of (R)—N—((R)-1-(naphthalen-1-yl)ethyl)-4-oxochromane-2-carboxamide (1.65 g, 92%). LC-MS: 346.34 (MH+). 1H NMR (400 MHz, DMSO-d6) δ 8.86 (d, J=7.9 Hz, 1H), 8.16-8.05 (m, 1H), 7.96 (dd, J=7.2, 2.3 Hz, 1H), 7.85 (d, J=8.1 Hz, 1H), 7.73 (dd, J=7.8, 1.8 Hz, 1H), 7.67-7.48 (m, 5H), 7.19-7.01 (m, 2H), 5.75 (dp, J=14.4, 7.1 Hz, 1H), 5.17 (dd, J=8.7, 5.1 Hz, 1H), 3.04-2.87 (m, 2H), 1.53 (dd, J=12.9, 6.9 Hz, 3H).

Example 4

Step-1: methyl (R)-4-oxochromane-2-carboxylate (Compound 19)

Compound 19

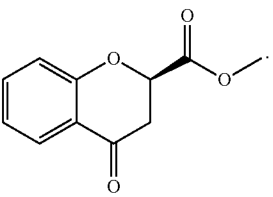

To a stirred mixture of Cu(OAc)2 (4.45 mg, 0.024 mmol) in THF (5 mL) added R-DM-SEGPHOS (19 mg, 0.027 mmol) and the resulting mixture stirred for 30-40 min at ambient temperature. Into this was added diethoxymethylsilane (1.569 mL, 9.80 mmol) at ambient temperature and stirred for additional 1 h. Then a solution of methyl 4-oxo-4H-chromene-2-carboxylate (0.5 g, 2.449 mmol) in THF (5 mL) was added to the catalyst mixture and continued stirring for 24 h. Upon completion, reaction mass was poured in to ice-cold water (10 mL) and product extracted with ethyl acetate (20 mL). Crude product was purified by column chromatography to get light yellow liquid of methyl (R)-4-oxochromane-2-carboxylate (430 mg, 85%). GC-MS: 206.11 (M+). 1H NMR (400 MHz, DMSO-d6) δ 7.75 (dd, J=7.8, 1.7 Hz, 1H), 7.61 (ddd, J=8.4, 7.2, 1.8 Hz, 1H), 7.15-7.08 (m, 2H), 5.47 (dd, J=8.1, 5.1 Hz, 1H), 3.70 (s, 3H), 3.16-2.98 (m, 2H).

Step-2: (R)-4-oxochromane-2-carboxylic acid (Compound 18)

Compound 18

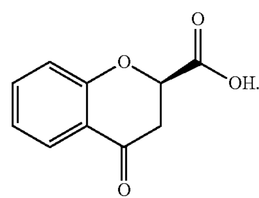

To a stirred solution of methyl (R)-4-oxochromane-2-carboxylate (1 g, 4.85 mmol) in THF (10 v) was added aqueous sodium hydroxide solution (5.203 mmol, 0.194 g in 2 mL water) and the resulting mixture stirred for 2 h. Upon completion, volatiles were removed by concentration and the mass obtained diluted with water 5 mL, then acidified carefully between 5-10° C. Precipitated products were collected by filtration and washed with water (2 mL) and dried under reduced pressure between 50-55° C. for 2 h, gave pure off-white solid of (R)-4-oxochromane-2-carboxylic acid (0.82 g, 88%). GC-MS: 192.13 (M+). 1H NMR (400 MHz, DMSO-d6) δ 13.36 (s, 1H), 7.74 (dd, J=7.8, 1.8 Hz, 1H), 7.60 (ddd, J=8.7, 7.2, 1.8 Hz, 1H), 7.15-7.05 (m, 2H), 5.33 (dd, J=7.5, 5.3 Hz, 1H), 3.11 (dd, J=17.0, 5.3 Hz, 1H), 2.98 (dd, J=17.0, 7.5 Hz, 1H).

Step-3: (R)—N—((R)-1-(naphthalen-1-yl)ethyl)-4-oxochromane-2-carboxamide (Compound 4)

Compound 4

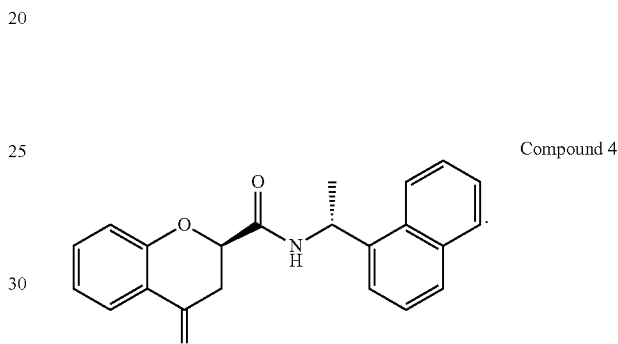

To a stirred solution of (R)-4-oxochromane-2-carboxylic acid (1 g, 5.025 mmol), TEA (1.09 mL, 7.807 mmol) in THF (6 v, 6 mL) were added T3P coupling reagent (3.72 mL, 6.246 mmol) at 5-10° C. under nitrogen atmosphere. Into this (R)-1-(naphthalen-1-yl)ethan-1-amine (0.891 g, 5.025 mmol) was added at same temperature and the resulting mass was slowly warm to ambient temperature and stirred for 16 h. Upon completion, it was diluted with ice-cold water (10 mL, 10 v) and product extracted with ethyl acetate (20 mL, 20 v). Organic phase separated and aqueous phase back extracted with ethyl acetate (10 mL, 10 v). Combined organic phase washed with water (8 mL*2, 16 v) and brine solution (8 mL, 8 v). It was concentrated to dryness, then crude solid was re-dissolved in ethanol (3 mL, 3 v) at 60-65° C. This was slowly cool to ambient temperature and stirred for 2 h. The mass was cooled to 0-5° C. and stirred for 30 min. Filtered the solid product, washed with ice-cold ethanol (1 mL, 1 v) and dried in vacuum tray drier at 50-55° C. for 3 h to get off-white solid of (R)—N—((R)-1-(naphthalen-1-yl)ethyl)-4-oxochromane-2-carboxamide (1.65 g, 92%). LC-MS: 346.34 (MH+). 1H NMR (400 MHz, DMSO-d6) δ 8.86 (d, J=7.9 Hz, 1H), 8.16-8.05 (m, 1H), 7.96 (dd, J=7.2, 2.3 Hz, 1H), 7.85 (d, J=8.1 Hz, 1H), 7.73 (dd, J=7.8, 1.8 Hz, 1H), 7.67-7.48 (m, 5H), 7.19-7.01 (m, 2H), 5.75 (dp, J=14.4, 7.1 Hz, 1H), 5.17 (dd, J=8.7, 5.1 Hz, 1H), 3.04-2.87 (m, 2H), 1.53 (dd, J=12.9, 6.9 Hz, 3H).

Example 5

Step 1: tert-butyl ((R)-1-(naphthalen-1-yl)ethyl)(((R,E)-4-(2-tosylhydrazineylidene)chroman-2-yl)methyl)carbamate (Compound 20)

Compound 20

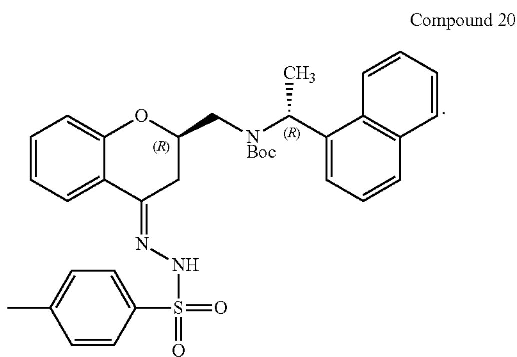

To a stirred solution of tert-butyl (1-(naphthalen-1-yl)ethyl)((4-oxochroman-2-yl)methyl)carbamate (1.2 g, 2.78 mmol) in ethanol (volume: 15 mL) was added 4-methylbenzenesulfonohydrazide (0.570 g, 3.06 mmol) and resulting mixture was heated between 85-90° C. for 10 h. Upon completion, reaction mass cool to 0-5° C. and precipitated product collected by filtration. It was suction dried to yield tert-butyl ((R)-1-(naphthalen-1-yl)ethyl)(((R,E)-4-(2-tosylhydrazineylidene)chroman-2-yl)methyl)carbamate (1.3 g, 2.168 mmol, 78% yield). LC-MS: 600.08 (MH+)

Step 2: methyl 5-((R)-2-(((tert-butoxycarbonyl)((R)-1-(naphthalen-1-yl)ethyl)amino)methyl)-2H-chromen-4-yl)-2-methylbenzoate (Compound 10)

Compound 10

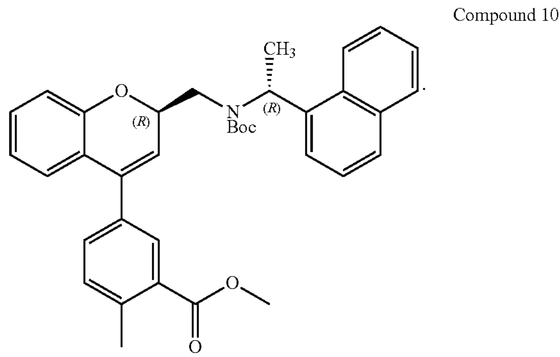

To a degassed solution of tert-butyl ((R)-1-(naphthalen-1-yl)ethyl)(((R,E)-4-(2-tosylhydrazineylidene)chroman-2-yl)methyl)carbamate (0.5 g, 0.834 mmol) in ethanol-toluene (volume: 10 mL, 1:1) mixture was added sequentially methyl 5-bromo-2-methylbenzoate (0.191 g, 0.834 mmol), dicyclohexyl-[2-[2,4,6-tri(propan-2-yl)phenyl]phenyl]phosphane (0.028 g, 0.058 mmol) and potassium carbonate (0.230 g, 1.667 mmol) between 25-30° C. The resulting mass degassed with nitrogen gas for additional 10 min period. In to this added catalyst Pd2(dba)3 (0.038 g, 0.042 mmol) and mass heated between 95-100° C. for 4 h. Upon completion, reaction mass diluted with water (10 mL) and extracted product with ethyl acetate. Organic layer dried over Na2SO4 and evaporated up to dryness to yield methyl 5-((R)-2-(((tert-butoxycarbonyl)((R)-1-(naphthalen-1-yl)ethyl)amino)methyl)-2H-chromen-4-yl)-2-methylbenzoate (400 mg, 0.710 mmol, 85% yield). LC-MS: 585.96 (M+Na). 1H NMR (400 MHz, DMSO-d6) δ: 8.08 (d, J=8.0 Hz, 1H), 7.97 (dd, J=8.1, 1.4 Hz, 1H), 7.91 (d, J=8.2 Hz, 1H), 7.68 (d, J=7.2 Hz, 1H), 7.65-7.49 (m, 4H), 7.35 (d, J=7.9 Hz, 1H), 7.21 (s, 1H), 7.10-7.02 (m, 1H), 6.81-6.69 (m, 2H), 6.38 (bs, 1H), 6.11 (bs, 1H), 5.19 (bs, 1H), 3.85 (s, 3H), 3.75 (bs, 1H), 3.31 (m, 1H), 2.53 (s, 3H), 1.65 (d, J=6.8 Hz, 3H), 1.50 (bs, 1H), 1.32 (bs, 9H).

In some aspects, this disclosure also provides for:

A1. A compound selected from (R)—N-(1-(naphthalen-1-yl)ethyl)-4-oxo-4H-chromene-2-carboxamide (Compound 3), (R)—N—((R)-1-(naphthalen-1-yl) ethyl)-4-oxochromane-2-carboxamide (Compound 4), (R)—N—((R)-1-(naphthalen-1-yl)ethyl)spiro[chromane-4,2'-[1,3]dioxolane]-2-carboxamide (Compound 5), (R)-1-(naphthalen-1-yl)-N—(((R)-spiro[chromane-4,2'-[1,3]dioxolan]-2-yl)methyl)ethan-1-amine (Compound 6), (R)-2-((((R)-1-(naphthalen-1-yl)ethyl)amino)methyl)chroman-4-one hydrochloride (Compound 7), (R)-2-((((R)-1-(naphthalen-1-yl)ethyl)amino)methyl)chroman-4-one (Compound 7"), and (R)-2-(((1-(naphthalen-1-yl)ethyl)amino)methyl)-4H-chromen-4-one (Compound 16), Compound 3

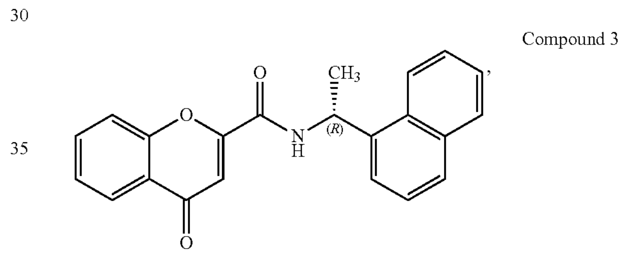

Compound 4

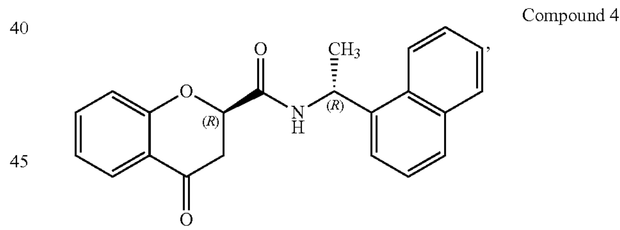

Compound 5

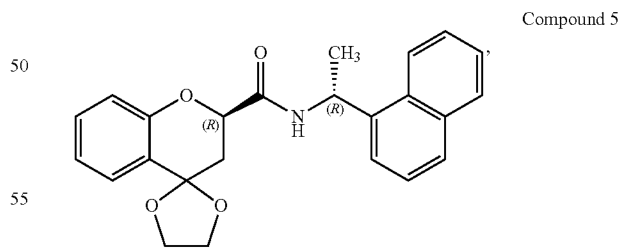

Compound 6

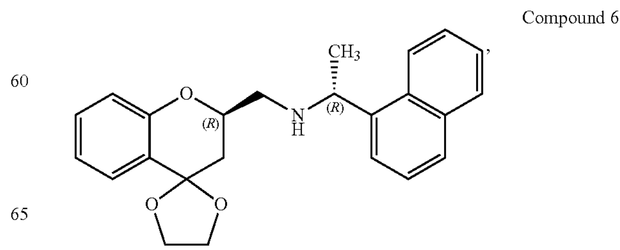

-continued

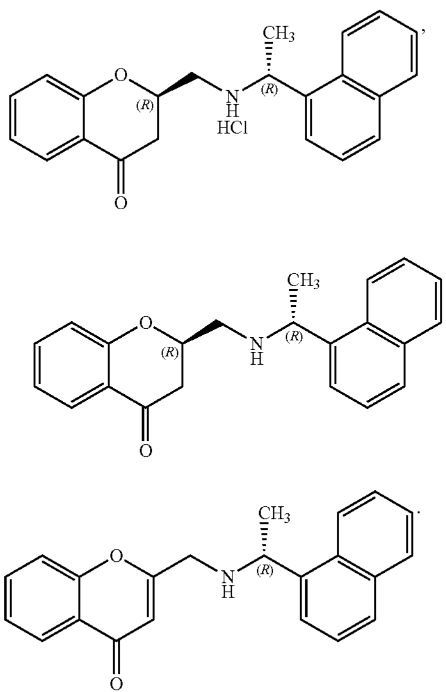

Compound 7

Compound 7'' and

Compound 16

A2. A method for the synthesis of tert-butyl ((R)-1-(naphthalen-1-yl)ethyl)(((R)-4-oxochroman-2-yl)methyl) carbamate (Compound 8) starting from 4-oxo-4H-chromene-2-carboxylic acid (Compound 1), the method comprising:

a) acid-amine coupling of Compound 1 with Compound 2 to obtain Compound 3 in the presence of propylphosphonic anhydride (T3P),

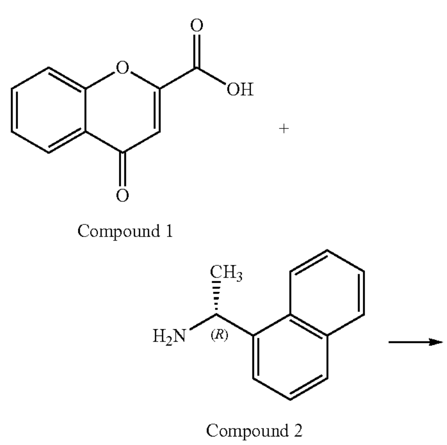

Compound 1

Compound 2

Compound 3 b) enantioselective reducing of the double bond of Compound 3 via asymmetric hydrogenation to obtain the optically active Compound 4,

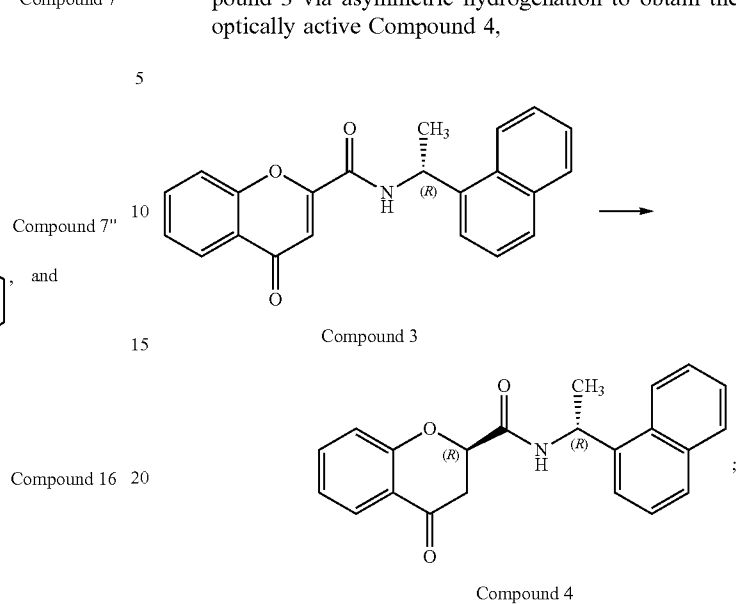

Compound 3

Compound 4 c) converting Compound 4 to obtain Compound 5 by reacting a glycol in PTSA and toluene,

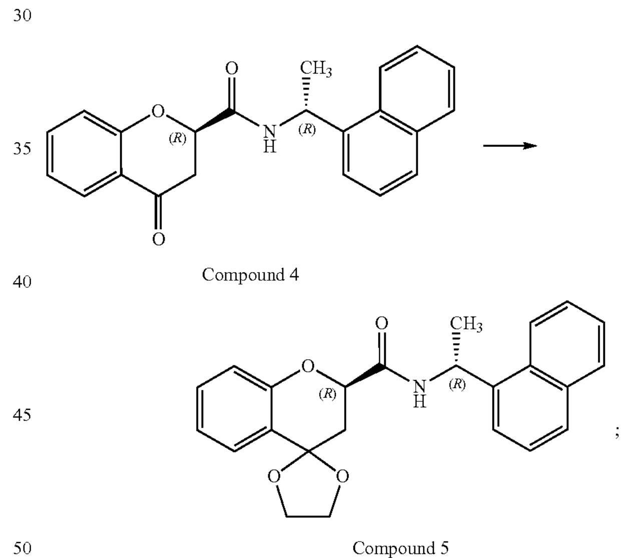

Compound 4

Compound 5 d) reducing the amide group of Compound 5 using Vitride to obtain Compound 6,

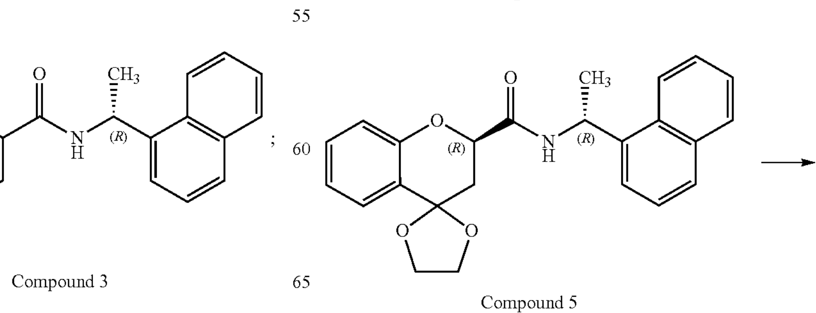

Compound 5

-continued

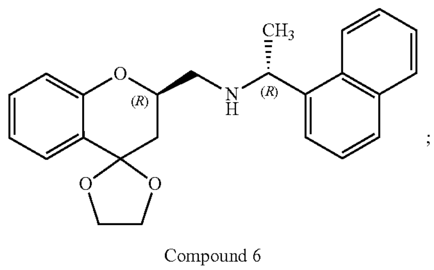

Compound 6 e) deprotecting Compound 6 using aqueous 6N HCl to obtain Compound 7,

Compound 6

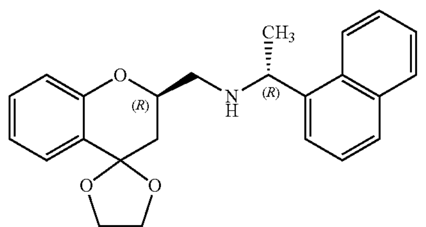

Compound 7

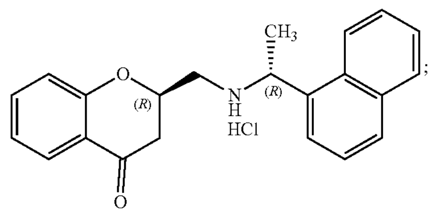

and f) protecting the free amino group of Compound 7 using Boc anhydride (Di-tert-butyl dicarbonate) and tripotassium phosphate to obtain Compound 8,

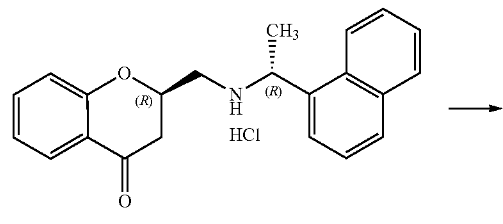

Compound 7

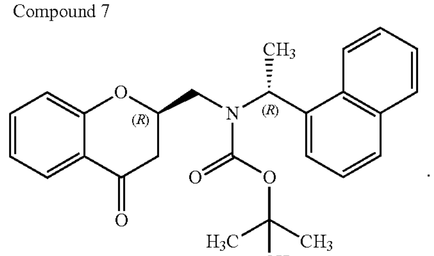

Compound 8

A3. The method of A2, wherein the synthesis produces 1 kg, 10 kg, or 100 kg of Compound 8.

A4. The method of A2, wherein in step (c), the glycol is ethylene glycol.

The inventions described and claimed herein have many attributes and embodiments including, but not limited to, those set forth or described or referenced in this Detailed Disclosure. It is not intended to be all-inclusive and the inventions described and claimed herein are not limited to or by the features or embodiments identified in this Detailed Disclosure, which is included for purposes of illustration only and not restriction. A person having ordinary skill in the art will readily recognize that many of the components and parameters may be varied or modified to a certain extent or substituted for known equivalents without departing from the scope of the invention. It should be appreciated that such modifications and equivalents are herein incorporated as if individually set forth. The invention also includes all of the steps, features, compositions and compounds referred to or indicated in this specification, individually or collectively, and any and all combinations of any two or more of said steps or features.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, and other referenced materials or documents. Reference to any applications, patents and publications in this specification is not, and should not be taken as, an acknowledgment or any form of suggestion that they constitute valid prior art or form part of the common general knowledge in any country in the world.

What is claimed is:

1. A method for the manufacture of 2-methyl-5-((2R,4S)-2-((((R)-1-(naphthalen-1-yl)ethyl)amino)methyl)chroman-4-yl)benzoic acid (Compound A") from methyl-5-((R)-2-(((tert-butoxycarbonyl)((R)-1-(naphthalen-1-yl)ethyl)amino)methyl)-2H-chromen-4-yl)-2-methylbenzoate (Compound 10), wherein the method comprising:

a. converting methyl-5-((R)-2-(((tert-butoxycarbonyl)((R)-1-(naphthalen-1-yl)ethyl)amino)methyl)-2H-chromen-4-yl)-2-methylbenzoate (Compound 10) to methyl 5-((2R)-2-(((tert-butoxycarbonyl)((R)-1-(naphthalen-1-yl)ethyl)amino)methyl)chroman-4-yl)-2-methylbenzoate (Compound 11), wherein the conversion is carried out through hydrogenation using palladium charcoal catalyst in methanolic ammonia under optimum hydrogen pressure not more than about 2.0 Kg/cm$^2$, or through treatment with ammonium formate in the presence of a palladium charcoal catalyst, in the presence of one or more polar solvents, wherein the one or more polar solvents is selected from methanol, ethanol, propanol, ethyl acetate, tetrahydrofuran, dioxane, and a combination thereof,

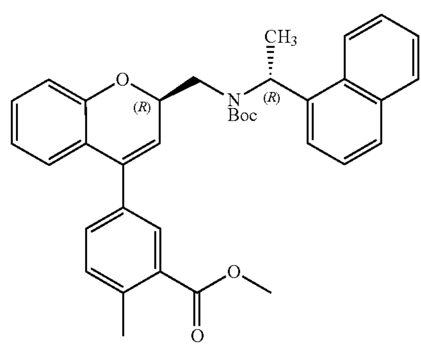

Compound 10

-continued

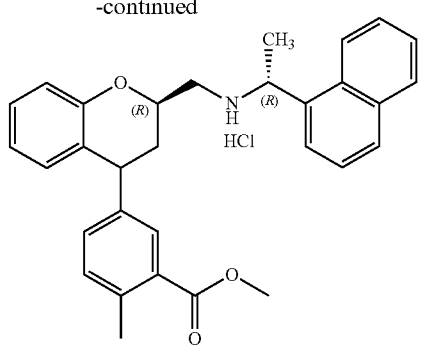

Compound 12

;

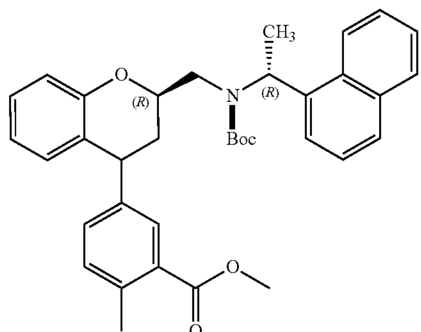

Compound 11

;

b. converting Compound 11 to methyl 2-methyl-5-((2R)-2-((((R)-1-(naphthalen-1-yl)ethyl)amino)methyl) chroman-4-yl)benzoate hydrochloride (Compound 12) through Boc-deprotection reaction using aqueous hydrochloric acid, trifluoroacetic acid or trimethyl silyl iodide in the presence of one or more polar solvents, wherein the one or more polar solvents is selected from methanol, dichloromethane, ethanol, propanol, ethyl acetate, tetrahydrofuran, dioxane, rand a combination thereof,

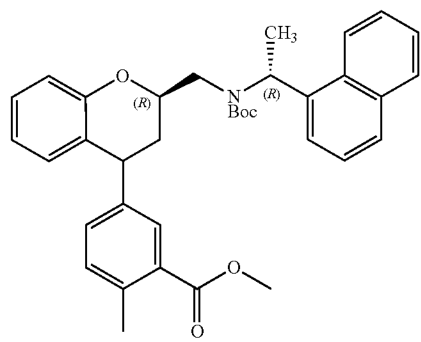

Compound 11 and c. hydrolyzing the ester group of Compound 12 using one or more hydroxide bases followed by aqueous reaction of the resultant carboxylate salt into the carboxylic acid to give 2-methyl-5-((2R,4S)-2-((((R)-1-(naphthalen-1-yl)ethyl)amino)methyl) chroman-4-yl)benzoic acid (Compound A"), wherein the one or more hydroxide bases is selected from sodium hydroxide, lithium hydroxide, potassium hydroxide, cesium hydroxide, lithium chloride, and a combination thereof,

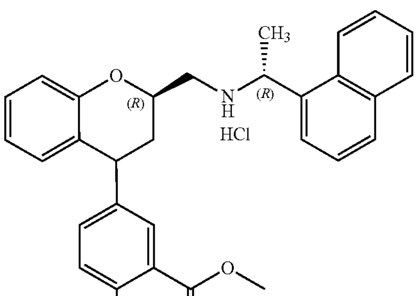

Compound 12

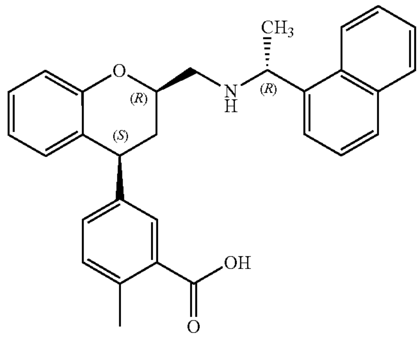

Compound A″

.

2. The method of claim 1, wherein step (c) further comprises isolating the pure diastereoisomer by using a recrystallization technique with a solvent mixture of one or more protic polar solvents and one or more aprotic polar solvents, wherein the one or more protic polar solvents is selected from ethanol, methanol, isopropanol, and a combination thereof, and the one or more aprotic polar solvents is selected from dichloromethane, dimethylformamide, tetrahydrofuran, and a combination thereof.

3. The method of claim 1, wherein methyl-5-((R)-2-(((tert-butoxycarbonyl) ((R)-1-(naphthalen-1-yl)ethyl) amino)methyl)-2H-chromen-4-yl)-2-methylbenzoate (Compound 10) is manufactured from (R)-2-(((tert-butoxycarbonyl) ((R)-1-(naphthalen-1-yl)ethyl)amino) methyl)-2H-chromen-4-yl trifluoromethanesulfonate (Compound 9), by reaction of Compound 9 with methyl 2-methyl-5-(4,4,5,5-tetramethyl-1,3,2-dioxaborolan-2-yl) benzoate in the presence of one or more palladium catalysts, wherein the one or more palladium catalysts is selected from palladium-tetrakis (triphenylphosphine), palladium(II)bis (triphenylphosphine) dichloride; palladium(0) bis(dibenzylideneacetone), palladium(II)bis(triphenylphosphine) diacetate, [1,1'-bis(diphenylphosphino)ferrocene]dichloropalladium(II)), and a combination thereof,

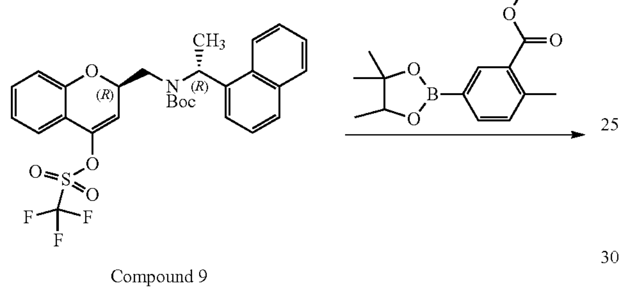

Compound 9

Compound 10

4. The method of claim 3, wherein (R)-2-(((tert-butoxycarbonyl) ((R)-1-(naphthalen-1-yl)ethyl)amino)methyl)-2H-chromen-4-yl trifluoromethanesulfonate (Compound 9) is manufactured from tert-butyl ((R)-1-(naphthalen-1-yl) ethyl)(((R)-4-oxochroman-2-yl)methyl) carbamate (Compound 8), by reaction of Compound 8 with one or more triflating agents, wherein the one or more triflating agents is selected from N-phenyl-bis(trifluoromethanesulfonimide), trifluoromethanesulfonic anhydride, N-(4-tert-Butylphenyl) bis(trifluoromethanesulfonimide), Bis(trifluoromethanesulfonyl)aniline, Comin's reagent, N-(5-Chloro-2-pyridyl) bis(trifluoromethanesulfonimide), trifluoromethanesulfonyl chloride, 4-nitrophenyl trifluoromethanesulfonate, 1-(trifluoromethanesulfonyl)imidazole)), and a combination thereof,

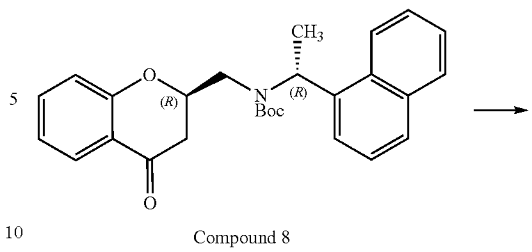

Compound 8

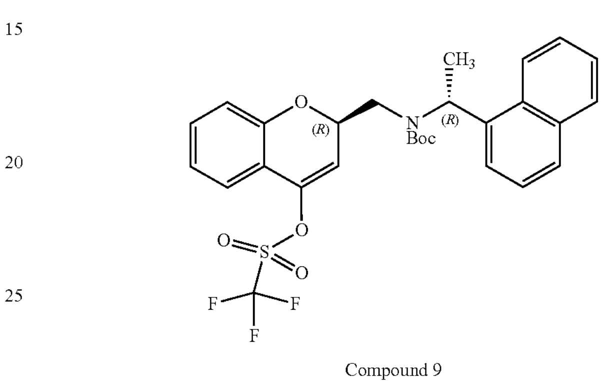

Compound 9

5. The method of claim 4, wherein tert-butyl ((R)-1-(naphthalen-1-yl)ethyl)(((R)-4-oxochroman-2-yl)methyl) carbamate (Compound 8) is manufactured from (R)-2-((((R)-1-(naphthalen-1-yl)ethyl)amino)methyl) chroman-4-one hydrochloride (Compound 7), by reacting Compound 7 with Boc anhydride (di-tert-butyl dicarbonate) and tripotassium phosphate,

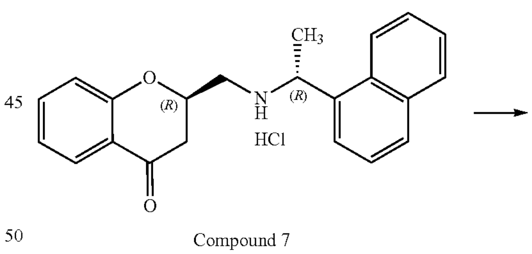

Compound 7

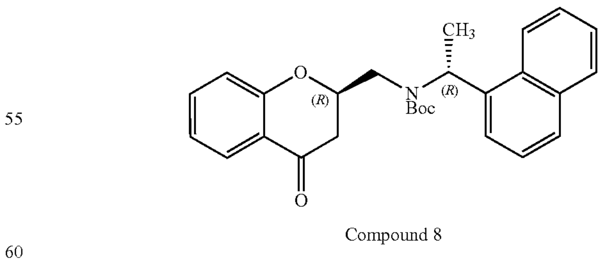

Compound 8

6. The method of claim 5, wherein (R)-2-((((R)-1-(naphthalen-1-yl)ethyl)amino)methyl) chroman-4-one hydrochloride (Compound 7) is manufactured from (R)-1-(naphthalen-1-yl)-N—(((R)-spiro[chromane-4,2'-[1,3]dioxolan]-2-yl)methyl)ethan-1-amine (Compound 6), by treatment of Compound 6 with aqueous hydrochloric acid,

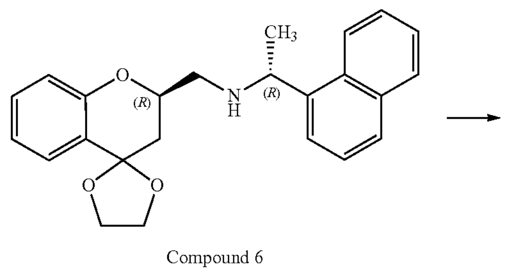

Compound 6

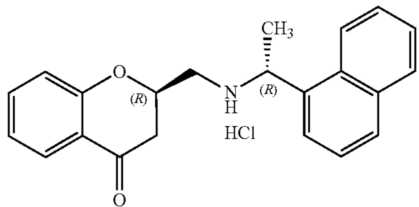

Compound 7

7. The method of claim 6, wherein (R)-1-(naphthalen-1-yl)-N—(((R)-spiro[chromane-4,2'-[1,3]dioxolan]-2-yl) methyl)ethan-1-amine (Compound 6) is manufactured from (R)—N—((R)-1-(naphthalen-1-yl)ethyl)spiro[chromane-4, 2'-[1,3]dioxolane]-2-carboxamide (Compound 5), by reducing the amide group of Compound 5 using one or more reducing agents, wherein the one or more reducing agents is selected from Vitride, borane-dimethyl sulphide complex, (Zn(OAc)2)/DEMS, and a combination thereof,

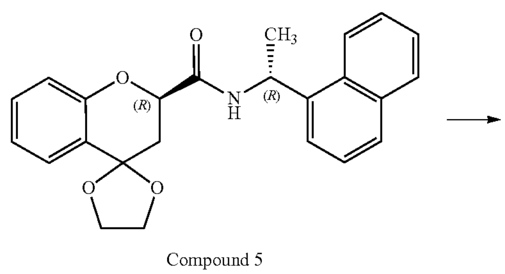

Compound 5

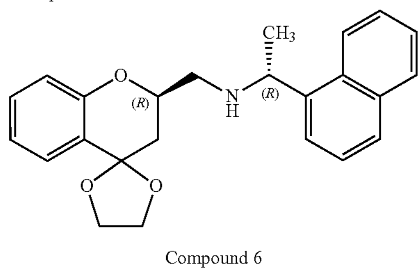

Compound 6

8. The method of claim 7, wherein (R)—N—((R)-1-(naphthalen-1-yl)ethyl)spiro[chromane-4,2'-[1,3]dioxolane]-2-carboxamide (Compound 5) is manufactured from (R)—N—((R)-1-(naphthalen-1-yl) ethyl)-4-oxochromane-2-carboxamide (Compound 4), by reacting Compound 4 with one or more glycols in the presence of one or more catalysts in the presence of a nonpolar solvent, wherein the one or more glycols is selected from ethylene glycol, propylene glycol, and a combination thereof, and wherein the one or more catalysts is selected from p-toluenesulfonic acid (PTSA), methanesulfonic acid (MSA), trifluoroacetic acid (TFA), tosylic acid (TsOH), pyridinium p-toluenesulfonate (PPTS), orthophosphoric acid, and a combination thereof,

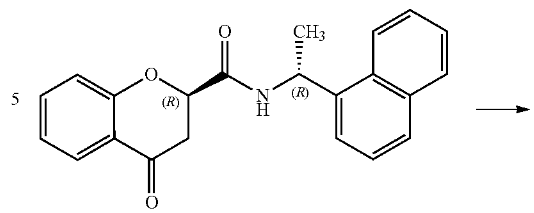

Compound 4

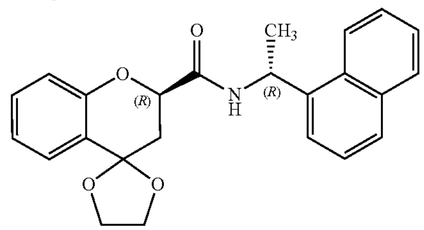

Compound 5

9. The method of claim 8, wherein (R)—N—((R)-1-(naphthalen-1-yl) ethyl)-4-oxochromane-2-carboxamide (Compound 4) is manufactured from (R)—N-(1-(naphthalen-1-yl)ethyl)-4-oxo-4H-chromene-2-carboxamide (Compound 3), by enantioselectively reducing the double bond of Compound 3 via asymmetric hydrogenation using one or more optically active diphosphine ligands, wherein the one or more optically active diphosphine ligands is selected from (R)-(+)-4,4'-Bis(diphenylphosphino)-3,3'-bi(1,2-methylenedioxybenzene), 4,4'-Bis(diphenylphosphino)-3,3'-bi(1,2-methylenedioxybenzene), (R)-(+)-4,4'-Bis[di(3,5-xylyl) phosphino]-3,3'-bi(1,2-methylenedioxybenzene), (R)-(−)-4,4'-Bis[di(3,5-di-tert-butyl-4-methoxyphenyl)phosphino]-3,3'-bi(1,2-methylenedioxybenzene), (R)-(+)-2,2'-Bis (diphenylphosphino)-1,1'-binaphthalene [(R)-BINAP], 2-Dicyclohexylphosphino-2',6'-dimethoxybiphenyl [s-Phos], 5-Bis(diphenylphosphino)-9,9-dimethylxanthene [Xantphos], (2R,3R)-(+)-Bis(diphenylphosphino)butane [R-Chiraphos], 4,4,4',4',6,6'-Hexamethyl-2,2'-spirobichroman-8,8'-diylbis(diphenylphosphane) [SPANphos], Bis(diphenylphosphinoethyl)phenylphosphine [Triphos], (2R,2'R, 5R,5'R)-2,2',5,5'-Tetramethyl-1,1'-(o-phenylene) diphospholane [R,R-Me-DuPhos], and a combination thereof, Compound 3

Compound 4

10. The method of claim 9, wherein (R)—N-(1-(naphthalen-1-yl)ethyl)-4-oxo-4H-chromene-2-carboxamide (Compound 3) is manufactured from 4-oxo-4H-chromene-2-carboxylic acid (Compound 1) by reaction with (R)-1-(naphthalen-1-yl)ethan-1-amine (Compound 2) in the presence of one or more amide coupling catalysts, wherein the one or more amide coupling catalysts is selected from propylphosphonic anhydride (T3P) 1-Ethyl-3-(3-dimethylaminopropyl)carbodiimide (EDCI), 1-Ethyl-3-(3-dimethylaminopropyl)carbodiimide hydrochloride (EDCI-HCl), N,N'-Dicyclohexylcarbodiimide (DCC), N,N'-Diisopropylcarbodiimide (DIC), 1-[Bis(dimethylamino)methylene]-1H-1,2,3-triazolo[4,5-b]pyridinium 3-oxide hexafluorophosphate (HATU), 2-(1H-benzotriazol-1-yl)-1,1,3,3-tetramethyluronium hexafluorophosphate (HBTU), and a combination thereof,

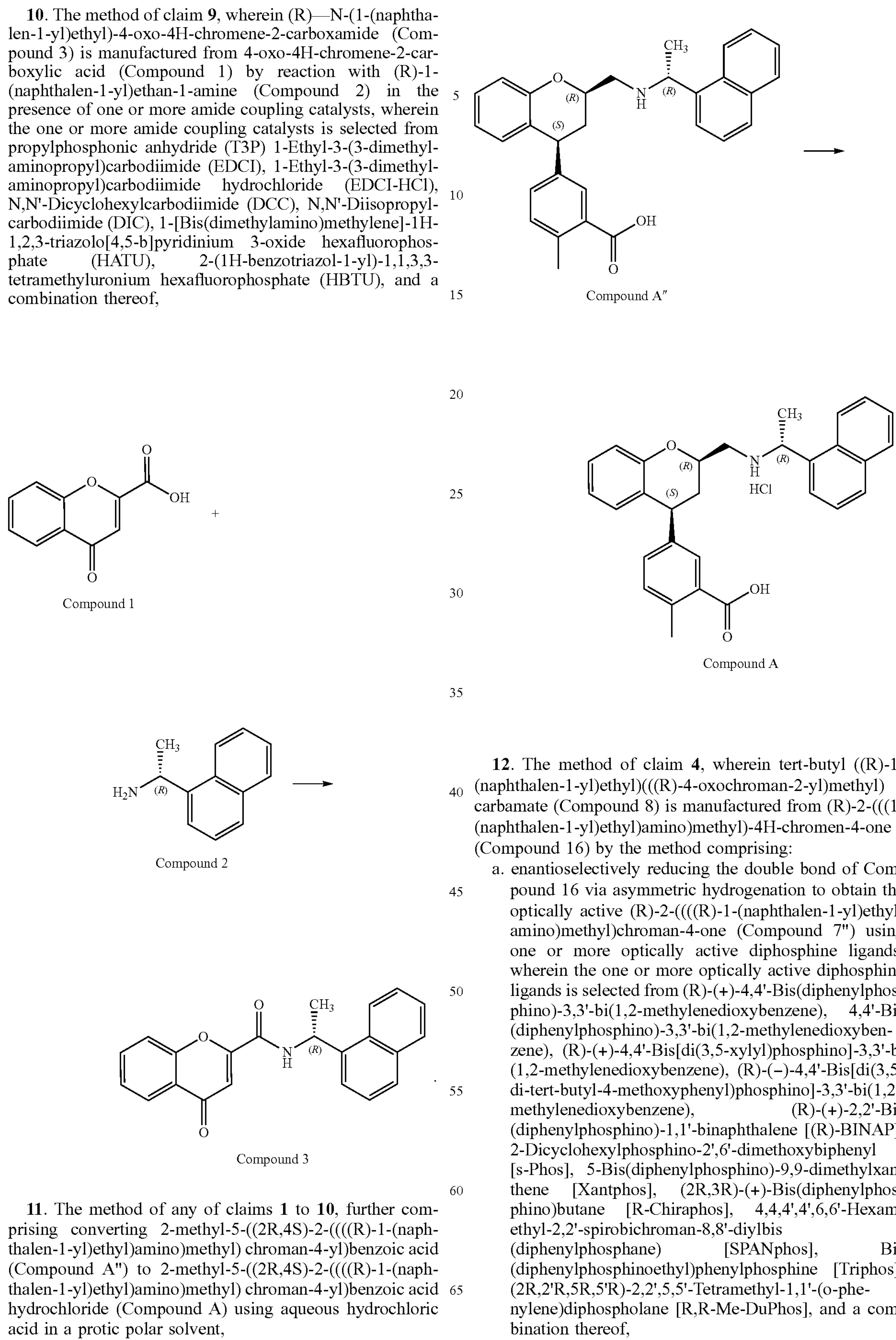

Compound 1

Compound 2

Compound 3

11. The method of any of claims 1 to 10, further comprising converting 2-methyl-5-((2R,4S)-2-((((R)-1-(naphthalen-1-yl)ethyl)amino)methyl) chroman-4-yl)benzoic acid (Compound A") to 2-methyl-5-((2R,4S)-2-((((R)-1-(naphthalen-1-yl)ethyl)amino)methyl) chroman-4-yl)benzoic acid hydrochloride (Compound A) using aqueous hydrochloric acid in a protic polar solvent, Compound A″

Compound A

12. The method of claim 4, wherein tert-butyl ((R)-1-(naphthalen-1-yl)ethyl)(((R)-4-oxochroman-2-yl)methyl) carbamate (Compound 8) is manufactured from (R)-2-(((1-(naphthalen-1-yl)ethyl)amino)methyl)-4H-chromen-4-one (Compound 16) by the method comprising:

a. enantioselectively reducing the double bond of Compound 16 via asymmetric hydrogenation to obtain the optically active (R)-2-((((R)-1-(naphthalen-1-yl)ethyl) amino)methyl)chroman-4-one (Compound 7") using one or more optically active diphosphine ligands, wherein the one or more optically active diphosphine ligands is selected from (R)-(+)-4,4'-Bis(diphenylphosphino)-3,3'-bi(1,2-methylenedioxybenzene), 4,4'-Bis (diphenylphosphino)-3,3'-bi(1,2-methylenedioxybenzene), (R)-(+)-4,4'-Bis[di(3,5-xylyl)phosphino]-3,3'-bi (1,2-methylenedioxybenzene), (R)-(−)-4,4'-Bis[di(3,5-di-tert-butyl-4-methoxyphenyl)phosphino]-3,3'-bi(1,2-methylenedioxybenzene), (R)-(+)-2,2'-Bis (diphenylphosphino)-1,1'-binaphthalene [(R)-BINAP], 2-Dicyclohexylphosphino-2',6'-dimethoxybiphenyl [s-Phos], 5-Bis(diphenylphosphino)-9,9-dimethylxanthene [Xantphos], (2R,3R)-(+)-Bis(diphenylphosphino)butane [R-Chiraphos], 4,4,4',4',6,6'-Hexamethyl-2,2'-spirobichroman-8,8'-diylbis (diphenylphosphane) [SPANphos], Bis (diphenylphosphinoethyl)phenylphosphine [Triphos], (2R,2'R,5R,5'R)-2,2',5,5'-Tetramethyl-1,1'-(o-phenylene)diphospholane [R,R-Me-DuPhos], and a combination thereof,

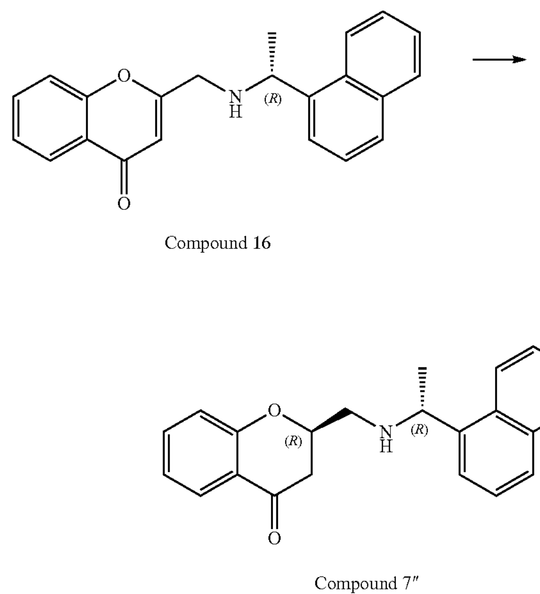

Compound 16

Compound 7″ and b. reacting Compound 7" with Boc anhydride (di-tert-butyl dicarbonate) in the presence of one or more basic catalysts to obtain Compound 8, wherein the one or more basic catalysts is selected from tripotassium phosphate, triethyl amine, pyridine, DMAP, DBU, DBN, sodium carbonate, sodium-bi-carbonate, sodium carbonate, potassium bi-carbonate, potassium carbonate, and a combination thereof,

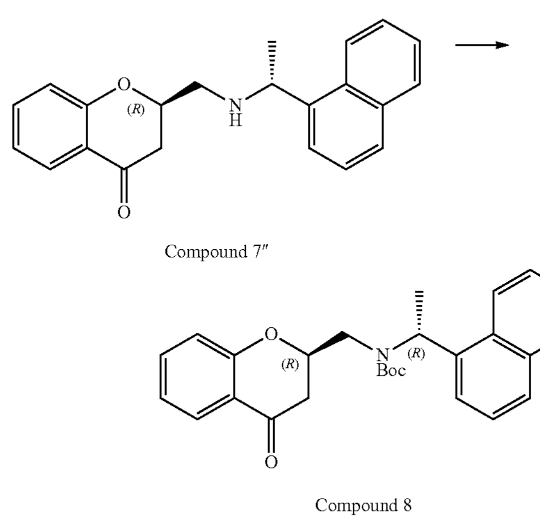

Compound 7″

Compound 8

13. The method of claim 12, wherein (R)-2-(((1-(naphthalen-1-yl)ethyl)amino)methyl)-4H-chromen-4-one (Compound 16) is manufactured from 2-(chloromethyl)-4H-chromen-4-one (Compound 15) by coupling Compound 15 with (R)-1-(naphthalen-2-yl)ethan-1-amine (Compound 2) in the presence of potassium carbonate, potassium iodide or a mixture thereof,

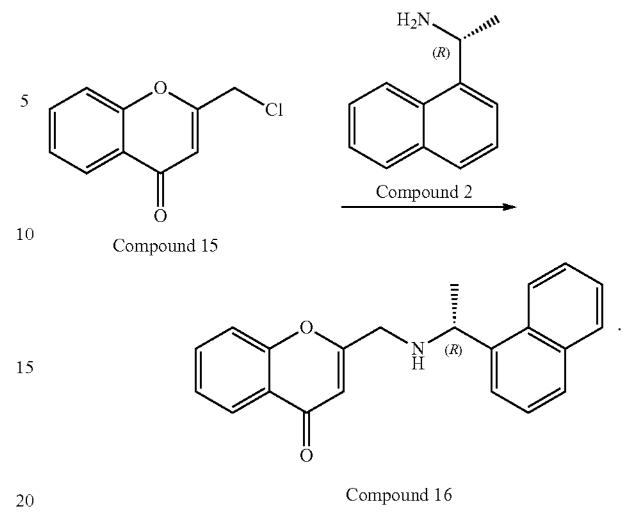

Compound 15

Compound 2

Compound 16

14. The method of claim 13, wherein 2-(chloromethyl)-4H-chromen-4-one (Compound 15) is manufactured by reacting 2-(hydroxymethyl)-4H-chromen-4-one (Compound 14) with thionyl chloride, one or more sulfonyl chlorides, or a combination thereof, wherein the one or more sulfonyl chlorides is selected from mesyl chloride, tosyl chloride, and a combination thereof,

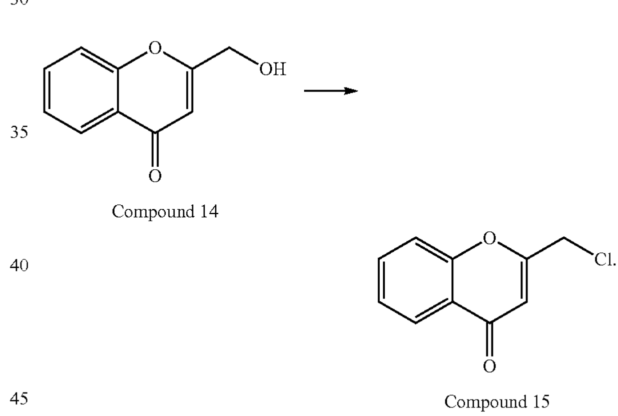

Compound 14

Compound 15

15. The method of claim 14, wherein 2-(hydroxymethyl)-4H-chromen-4-one (Compound 14) is manufactured from methyl 4-oxo-4H-chromene-2-carboxylate (Compound 13) by reacting Compound 13 with one or more reducing agents, wherein the one or more reducing agents is selected from sodium borohydride, borane dimethyl sulfide (THF solution), lithium borohydride (LiBH4), lithium aluminum hydride (LiAlH4), and a combination thereof,

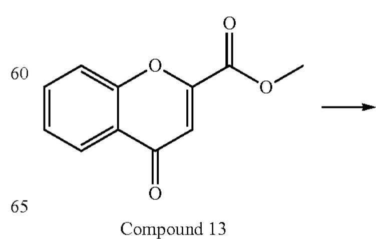

Compound 13

-continued
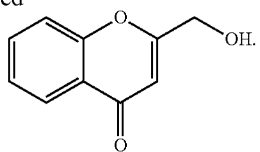
Compound 14
* * * * *